United States Patent
Yaffe et al.

(10) Patent No.: US 9,610,332 B2
(45) Date of Patent: Apr. 4, 2017

(54) COMPOSITIONS AND METHODS FOR MODULATING BRD4 BIOACTIVITY

(71) Applicant: Massachusetts Institute of Technology, Cambridge, MA (US)

(72) Inventors: Michael B. Yaffe, West Roxbury, MA (US); Scott R. Floyd, West Roxbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 527 days.

(21) Appl. No.: 13/945,674

(22) Filed: Jul. 18, 2013

(65) Prior Publication Data

US 2014/0044770 A1 Feb. 13, 2014

Related U.S. Application Data

(60) Provisional application No. 61/672,964, filed on Jul. 18, 2012.

(51) Int. Cl.
| | |
|---|---|
| *A61K 31/7088* | (2006.01) |
| *A61K 38/17* | (2006.01) |
| *A61K 38/46* | (2006.01) |
| *A61K 31/5517* | (2006.01) |
| *C12Q 1/68* | (2006.01) |
| *G01N 33/573* | (2006.01) |

(52) U.S. Cl.
CPC ........ *A61K 38/465* (2013.01); *A61K 31/5517* (2013.01); *A61K 38/1709* (2013.01); *C12Q 1/6886* (2013.01); *G01N 33/573* (2013.01)

(58) Field of Classification Search
CPC ................ A61K 31/7088; A61K 38/17; A61K 38/1709; A61K 2121/00
USPC ............ 514/12, 44; 530/350, 358; 536/23.1, 536/23.4, 23.5
See application file for complete search history.

(56) References Cited

FOREIGN PATENT DOCUMENTS

| EP | 2239264 | 10/2010 |
|---|---|---|
| WO | 2011143669 | 11/2011 |
| WO | 2013030150 | 3/2013 |

OTHER PUBLICATIONS

Bartek and Lukas, Curr. Op. Cell Biol. 13:738-747, 2001.*
Ottinger et al, J. Virol. 80(21):10772-10786, 2006.*
Xu et al, Human Gene Therapy 10:2941-2952, 1999.*
Broaddus et al, J. Neurosur. 91:997-1004, 1999.*
Strausberg et al, GenBank AAH35266, 2005.*
Wu et al, J. Biol. Chem. 282(18):13141-1345, 2007.*
Floyd et al, Nature 498:246-250, 2013.*
Yan et al, J. Biol. Chem. 286(31):27663-27675, 2011; available online Jun. 7, 2011.*
Bartkova, et al., "DNA damage response as a candidate anti-cancer barrier in early human tumorigenesis", Nature, 434:864-70 (2005).
Bartkova, et al., "Oncogene-induced senescence is part of the tumorigenesis barrier imposed by DNA damage checkpoints", Nature, 444:633-7 (2006).
Busby, et al., "The radiosensitizing agent 7-hydroxystaurosporine (UCN-01) inhibits the DNA damage checkpoint kinase hChk1", Cancer Res, 60:2108-12 (2000).
Carey and Smale, "Micrococcal Nuclease-Southern Blot Assay: I. MNase and Restriction Digestions", CSH Protoc., pdb.prot4890 (2007).
Carpenter, et al., "CellProfiler: image analysis software for identifying and quantifying cell phenotypes", Genome Biol, 7(10):R100 (2006).
Carpenter, et al., "Systematic genome-wide screens of gene function", Nat Rev Genet, 5:11-22 (2004).
Chowdhury, et al., "gamma-H2AX dephosphorylation by protein phosphatase 2A facilitates DNA double-strand break repair", Mol Cell, 20:801-9 (2005).
Cowell, et al., et al., "gammaH2AX foci form preferentially in euchromatin after ionising-radiation", PLoS ONE, 2:e1057 (2007).
Das, et al., "CBP/p300-mediated acetylation of histone H3 on lysine 56", Nature, 459:113-7 (2009).
Dey, et al., "A bromodomain protein, MCAP, associates with mitotic chromosomes and affects G(2)-to-M transition", Mol. Cell. Biol., 20:6537-49 (2000).
Dey, et al., "The double bromodomain protein Brd4 binds to acetylated chromatin during interphase and mitosis", PNAS,, 100:8758-63 (2003).
Di Micco, et al., "Interplay between oncogene-induced DNA damage response and heterochromatin in senescence and cancer", Nature Cell Biol,.13(3):292-302 (2011).
Di Micco, et al., "Oncogene-induced senescence is a DNA damage response triggered by DNA hyper-replication", Nature, 444:638-42 (2006).
Engleson, et al., "Midline carcinoma with t(15;19) and BRD4-NUT fusion oncogene in a 30-year-old female with response to docetaxel and radiotherapy", BMC Cancer, 6:69 (2006).
Filippakopoulos, et al., "Selective inhibition of BET bromodomains", Nature, 468:1067-73 (2010).
Florence and Faller, "You bet-cha: a novel family of transcriptional regulators", Front. Biosci. 6:D1008-18 (2001).
Floyd, et al., "The bromodomain protein Brd4 insulates chromatin from DNA damage signaling", Nature, 498(7453):246-50 (2013).
French, et al., "BRD-NUT oncoproteins: a family of closely related nuclear proteins that block epithelial differentiation and maintain the growth of carcinoma cells", Oncogene, 27:2237-42 (2008).

(Continued)

Primary Examiner — Kevin Hill
(74) Attorney, Agent, or Firm — Pabst Patent Group LLP

(57) ABSTRACT

Compositions and methods for increasing or decreasing DNA repair are provided. Composition includes a Brd4 polypeptide, fragment, fusion, or variant thereof. The fusion protein can include a protein transduction, a targeting domain, or a combination thereof to enhance delivery of the fusion protein to the interior of a particular target cell, such as a cancer cell. Inhibitory nucleic acids that target a Brd4 mRNA and antibodies that target a Brd4 polypeptide are also disclosed. The inhibitory nucleic acid or antibody can target a sequence or epitope on Brd4 isoform B that is absent on Brd4 isoform A and Brd4 isoform C. Methods for increasing or decreasing the sensitivity of cells to a DNA damaging agent, methods of treating cancer, and methods of determining cells' sensitivity to a DNA damaging agent are also disclosed.

30 Claims, 21 Drawing Sheets

(56) References Cited

OTHER PUBLICATIONS

French, et al., "BRD4-NUT fusion oncogene: a novel mechanism in aggressive carcinoma", Cancer Res., 63(2): 304-7 (2003).
French, et al., "BRD4 bromodomain gene rearrangement in aggressive carcinoma with translocation t(15;19)", J. Clin. Path., 159(6):1987-92 (2001).
French, et al., "Demystified molecular pathology of NUT midline casrcinomas", J. Clin. Path., 63:492-6 (2010).
French, et al., "Midline carcinoma of children and young adults with NUT rearrangement", Clin. Oncol., 22:4135-9 (2004).
GenBank Accession No. AY166680.1, "*Homo sapiens* BRD4-NUT fusion oncoprotein (BRD4-NUT fusion) mRNA, complete cds", 3 pages, First available 01-20-003, accessed Nov. 11, 2013.
GenBank Accession No. BC035266, "*Homo sapiens* bromodomain containing 4, mRNA (cDNA clone MGC:42948 Image:4837491), complete cds", 3 pages, First available Sep. 23, 2002, accessed Nov. 11, 2013.
GenBank Accession No. NM 014299.2, "*Homo sapiens* bromodomain containing 4 (BRD4), transcript variant short, mRNA", 7 pages, First available Aug. 18, 2006, accessed Nov. 11, 2013.
GenBank Accession No. NM 058243, "*Home sapiens* bromodomain containing 4 (BRD4), transcript variant long, mRNA", 8 pages, First available Mar. 26, 2002, accessed Nov. 11, 2013.
Goodarzi, et al., "ATM signaling facilitates repair of DNA double-strand breaks associated with heterochromatin", Molecular Cell, 31:167-77 (2008).
Hargreaves, et al., "Control of inducible gene expression by signal-dependent transcriptional elongation", Cell, 138:129-45 (2009).
Harper, et al., "The DNA damage response: ten years after", Mol. Cell, 28:739-45 (2007).
Helleday, et al., "DNA repair pathways as targets for cancer therapy", Nature Rev Cancer, 8(3):193-204 (2008).
Jackson, et al., "The DNA-damage response in human biology and disease", Nature, 461:1071-8 (2009).
Jang, et al., "The bromodomain protein Brd4 is a positive regulatory component of P-TEFb and stimulates RNA polymerase II-dependent transcription", Molecular Cell, 19:523-34 (2005).
Jones, et al., "Scoring diverse cellular morphologies in image-based screens with iterative feedback and machine learning", PNAS, 106:1826-31 (2009).
Kruhlak, "Changes in chromatin structure and mobility in living cells at sites of DNA double-strand breaks", J Cell Biol.,, 172:823-34 (2006).
Lamprecht, et al., "CellProfiler: free, versatile software for automated biological image analysis", Biotechniques, 42:71-5 (2007).
Lee, et al., "A cooperative activation loop among SWI/SNF, gamma-H2AX and H3 acetylation for DNA double-strand break repair", EMBO J., 29:1434-45 (2010).
Lee, et al., "Histone acetyltransferase complexes: one size doesn't fit all", Nat. Rev. Mol. Cell Biol., 8:284-95 (2007).
Margueron, et al., "Chromatin structure and the inheritance of epigenetic information", Nat. Rev. Genet., 11:285-96 (2010).
Mertens, et al., "Successful treatment of a child with t(15;19)-positive tumor", Pediatr Blood Cancer, 49:1015-7 (2007).
Mertz, et al., "Targeting MYC dependence in cancer by inhibiting BET broomodomains", PNAS, 108(40)16669-74 (2011).
Misteli, et al., "The emerging role of nuclear architecture in DNA repair and genome maintenance", Nat. Rev. Mol. Cell Biol., 10:243-54 (2009).
Moffat, et al., "A lentiviral RNAi library for human and mouse genes applied to an arrayed viral high-content screen", Cell, 124:1283 (2006).
Moynahan, et al., "BRCA2 is required for homology-directed repair of chromosomal breaks", Molecular Cell, 7:263-72 (2001).
Murga, et al., "Global chromatin compaction limits the strength of the DNA damage response", J Cell Biol., 178:1101-8 (2007).
Nussenzweig, et al., "Hypersensitivity of Ku80-deficient cell lines and mice to DNA damage: the effects of ionizing radiation on growth, survival, and development", PNAS, 94:13588 (1997).
Root, et al., "Genome-scale loss-of-function screening with a lentiviral RNAi library", Nat Methods, 3:715-9 (2006).
Santis, et al., "Successful radical treatment of midline carcinoma with t(15;19) diagnosed by endobronchial ultrasound-derived transbronchial needle aspiration", Grin Oncol., 29 (12):e327-9. (2011).
Schwartz, et al., "Differentiation of NUT midline carcinoma by epigenomic reprogramming", Cancer Res., 71:2686-96 (2011).
Smyth, "Linear models and empirical bayes methods for assessing differential expression in microarray experiments", Stat. Appl. Genet. Mol. Biol., 3 Article 3 (2004).
Stavenhagen, et al., "Fc optimization of therapeutic antibodies enhances their ability to kill tumor cells in vitro and controls tumor expansion in vivo via low-affinity activating Fcgamma receptors", Cancer Res., 57(18):8882-90 (2007).
Tjeertes, et al., "Screen for DNA-damage-responsive histone modifications identifies H3K9Ac and H3K56Ac in human cells", EMBO J., 28(13):1878-89 (2009).
Van Attikum, et al., "Crosstalk between histone modifications during the DNA damage response", Trends Cell Biol., 19:207-17 (2009).
Venkitaraman, "Cancer susceptibility and the functions of BRCA1 and BRCA2", Cell, 108:171-82 (2002).
Vollmuth, et al., "Structures of the dual bromodomains of the P-TEFb-activating activating protein Brd4 at atomic resolution", J Biol Chem, 284:36547-56 (2009).
Yang, et al., "Recruitment of P-TEFb for stimulation of transcriptional elongation by the bromodomain protein Brd4", Molecular Cell, 19:535-45 (2005).
Zeng and Zhou, "Bromodomain: an acetyl-lysine binding domain", FEBS Lett., 513:124-8 (2002).
Ziv, et al., "Chromatin relaxation in response to DNA double-strand breaks is modulated by a novel ATM- and KAP-1 dependent pathway", Nature, 8:870-6 (2006).
Alsarraj and Hunter. "Bromodomain-containing protein 4: A dynamic regulator of breast cancer metastasis through modulation of the extracellular matrix", Intl. J Breast Cancer 2012:article ID 670622, pp. 1-7 (2012).
Alsarraj, et al., "Deletion of the proline-rich region of the murine metastasis suscrptibility gene Brd4 promotes Epithelial-to-mesenchymal transition- and stem cell-like conversion", Cancer Res., 71 (8):3121-31 (2011).
BRD4 (bromodomain containing 4), Atlas of genetics and cytogenetics in oncology and haematology, http://atlatgeneticsoncology.org/Genes/BRD4ID837ch19p13., retrieved from the Internet Feb. 23, 2012.
Crawford, et al., "Bromodomain 4 activation predicts breast cancer survival", PNAS, 105(176380-5 (2008).
Huen and Chen, et al., "The DNA damage response pathways: at the crossroad of protein modifications", Cell Res., 18:8-16 (2008).
Rossetto, et al., "Epigenetic modifications in double-strand break DNA damage signaling and repair", Clin Cancer Res., 16(18):4543-52 (2010).
Wang, et al., "The bromodomain protein BRD4 associated with acetylated chromatin is important for maintenance of higher-order chromatin structure", J Bioc CheM., 287 (14):10738-52 (2012).

* cited by examiner

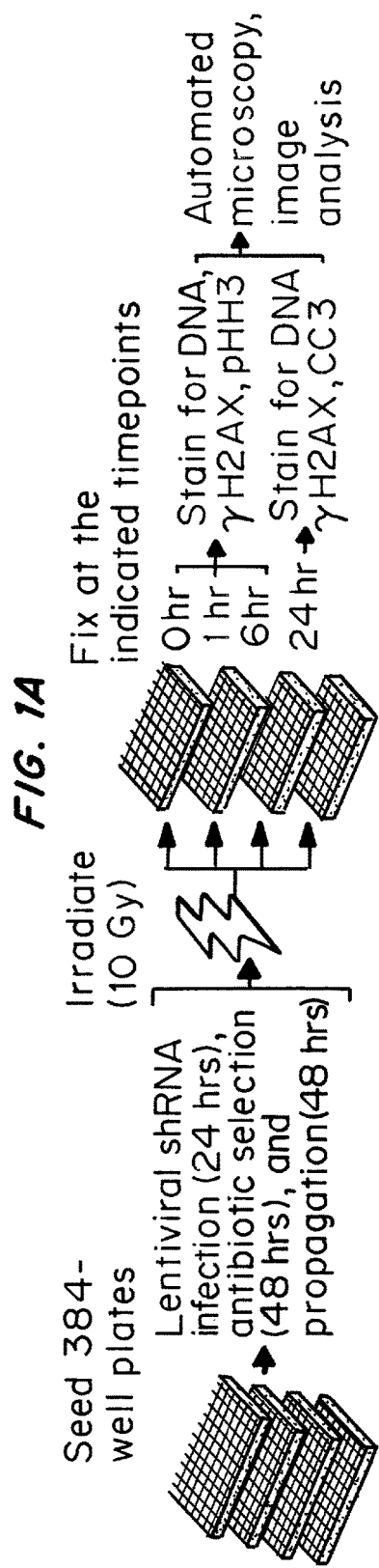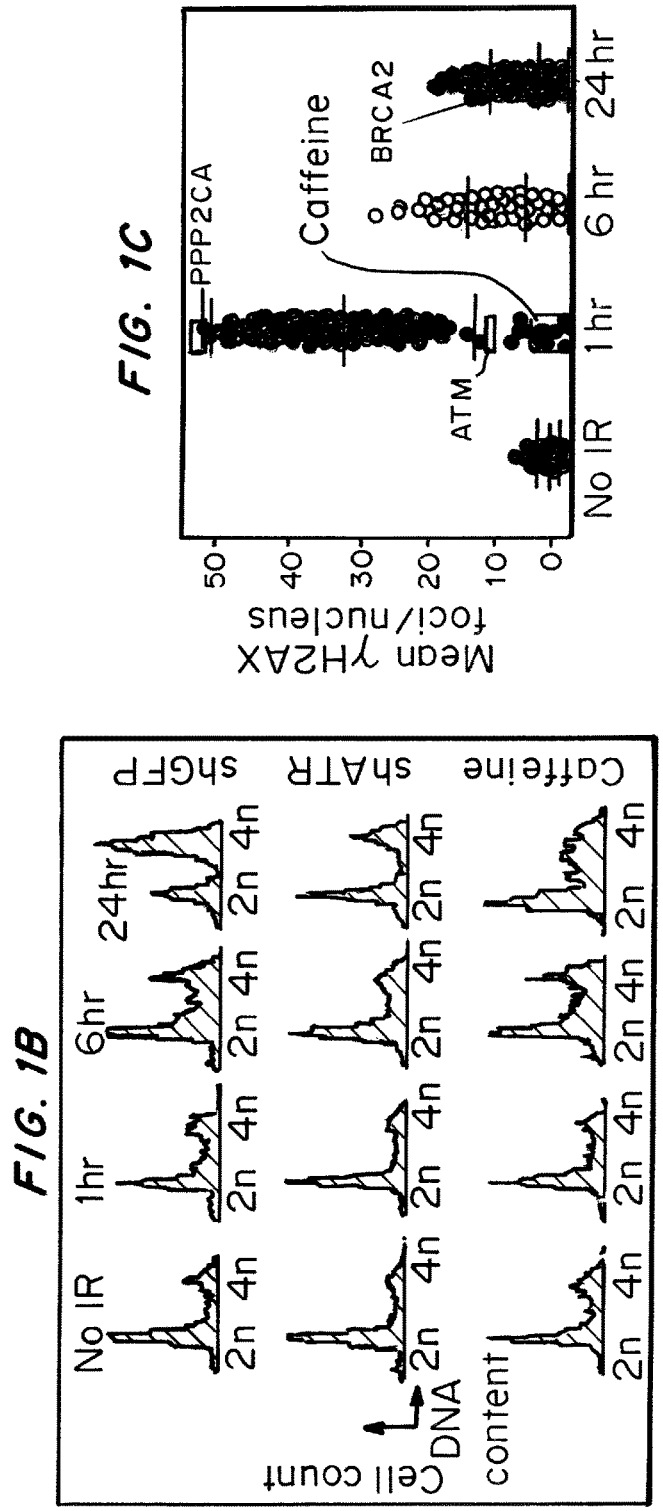

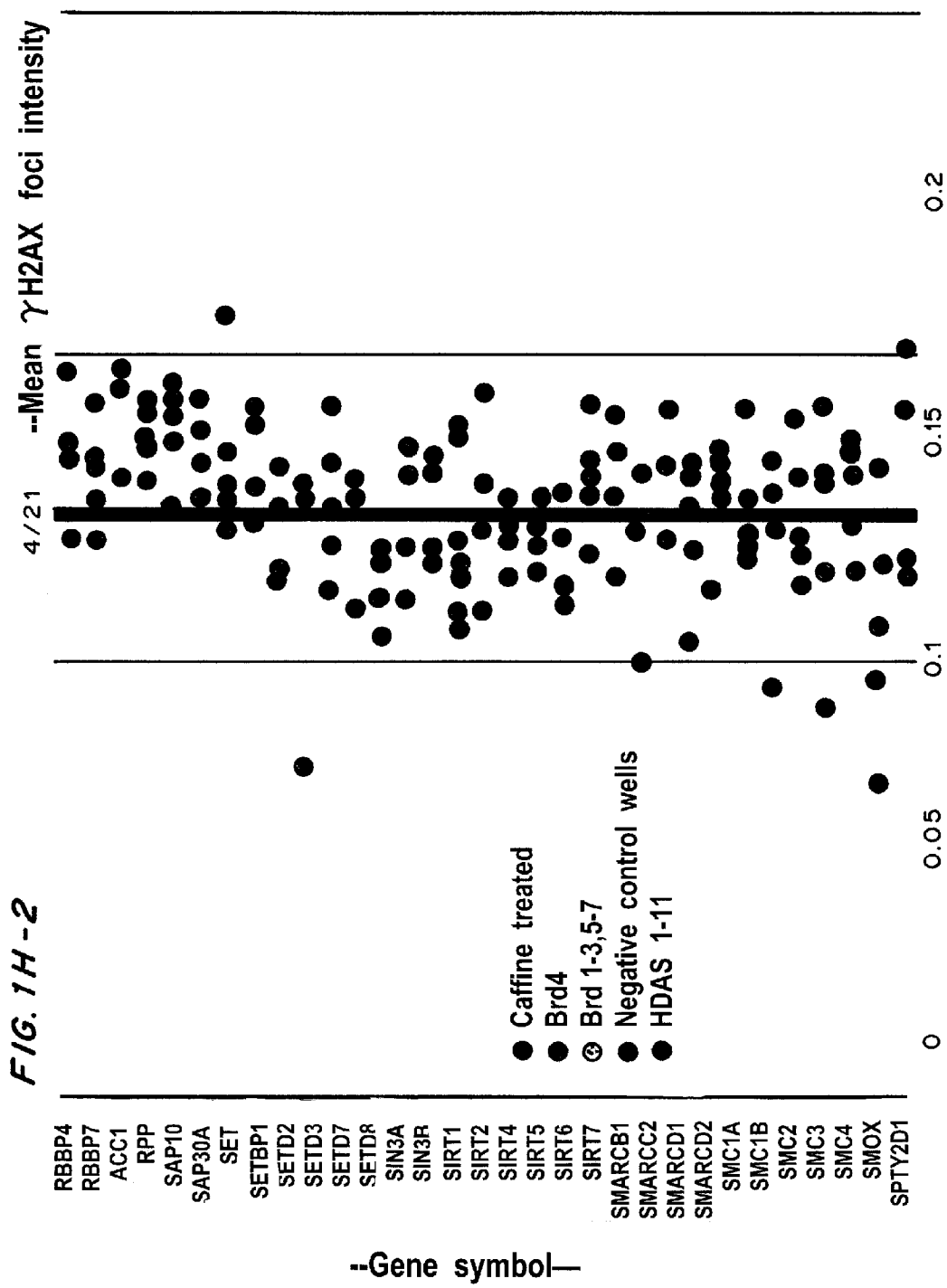

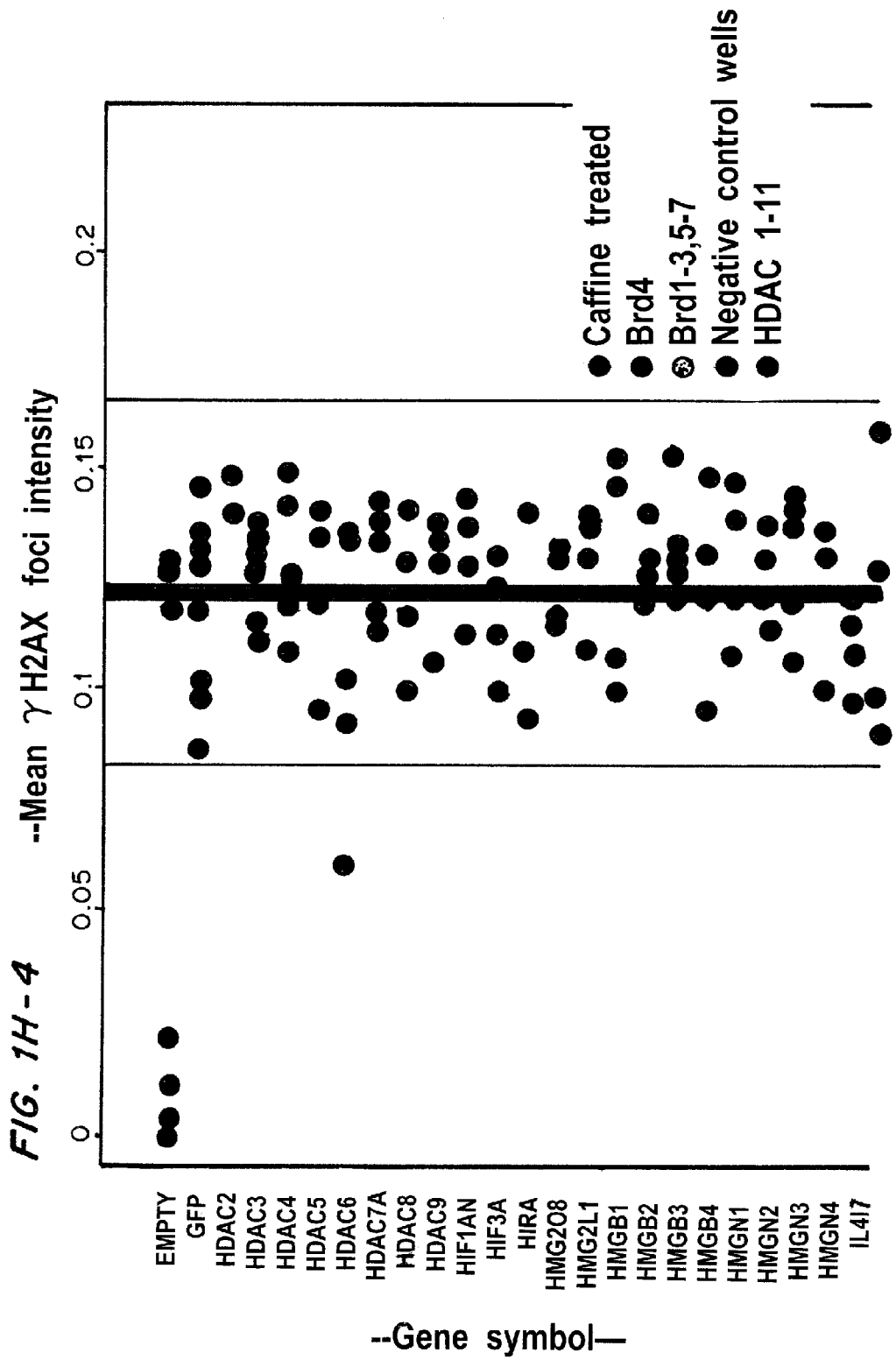

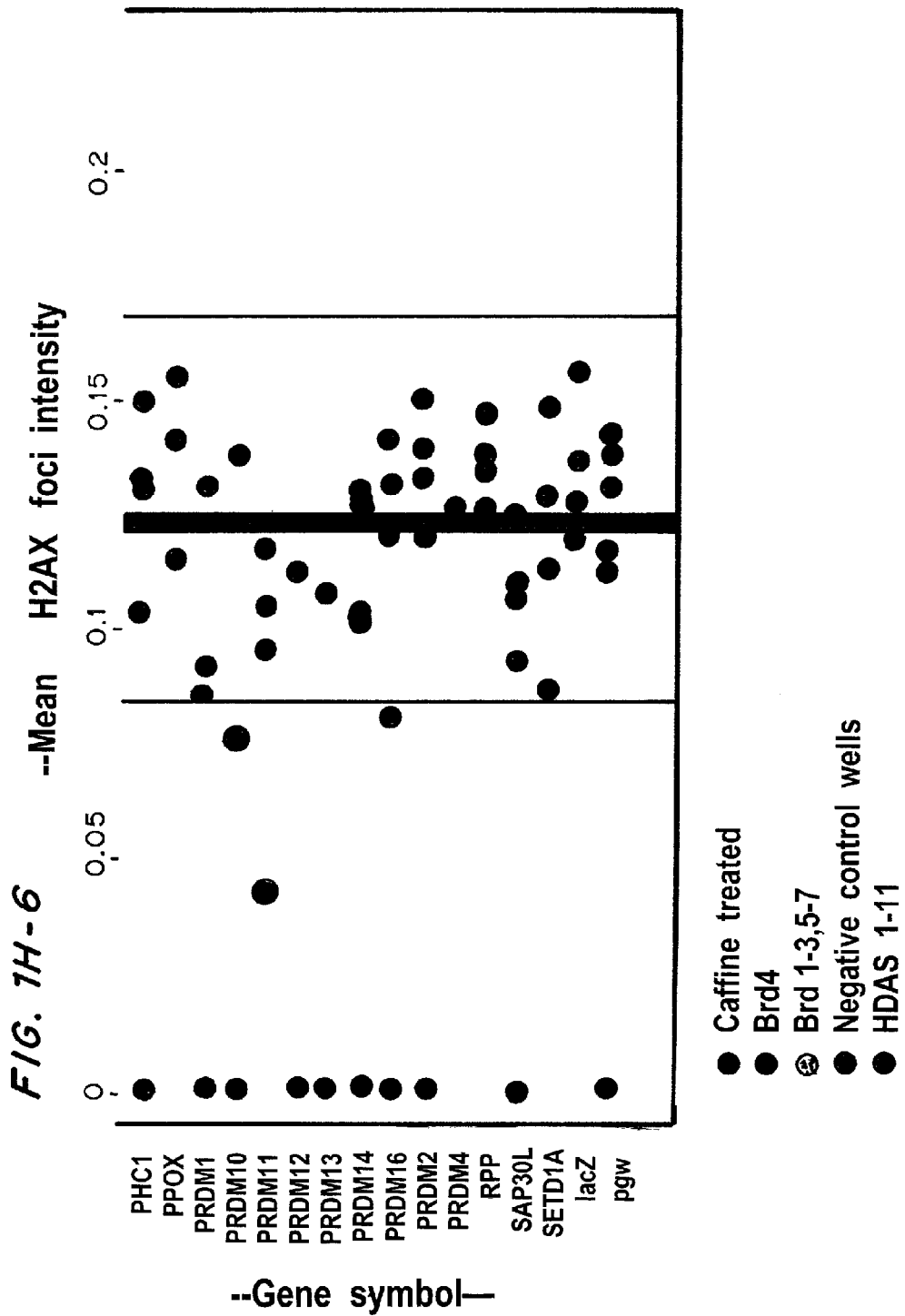

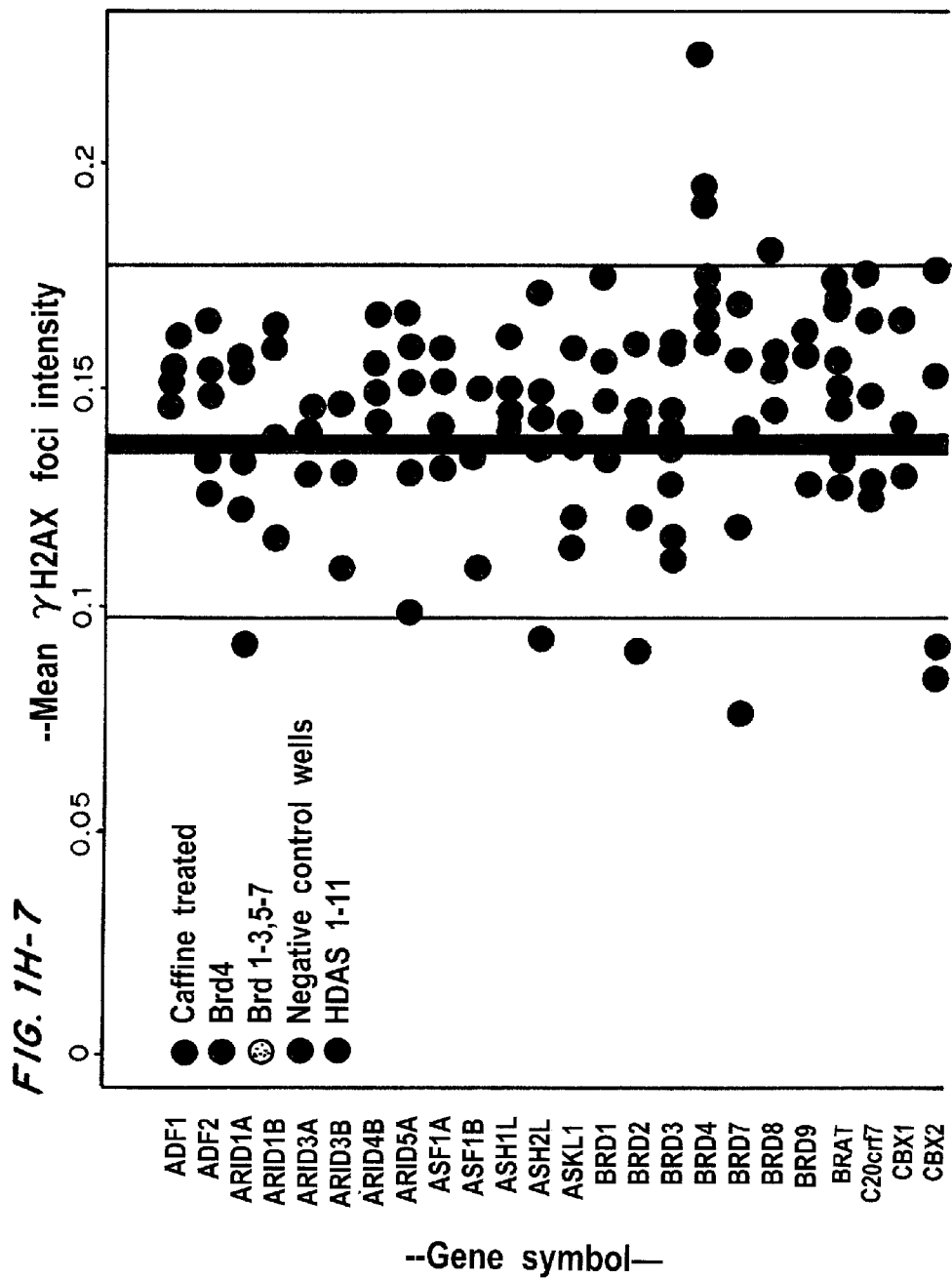

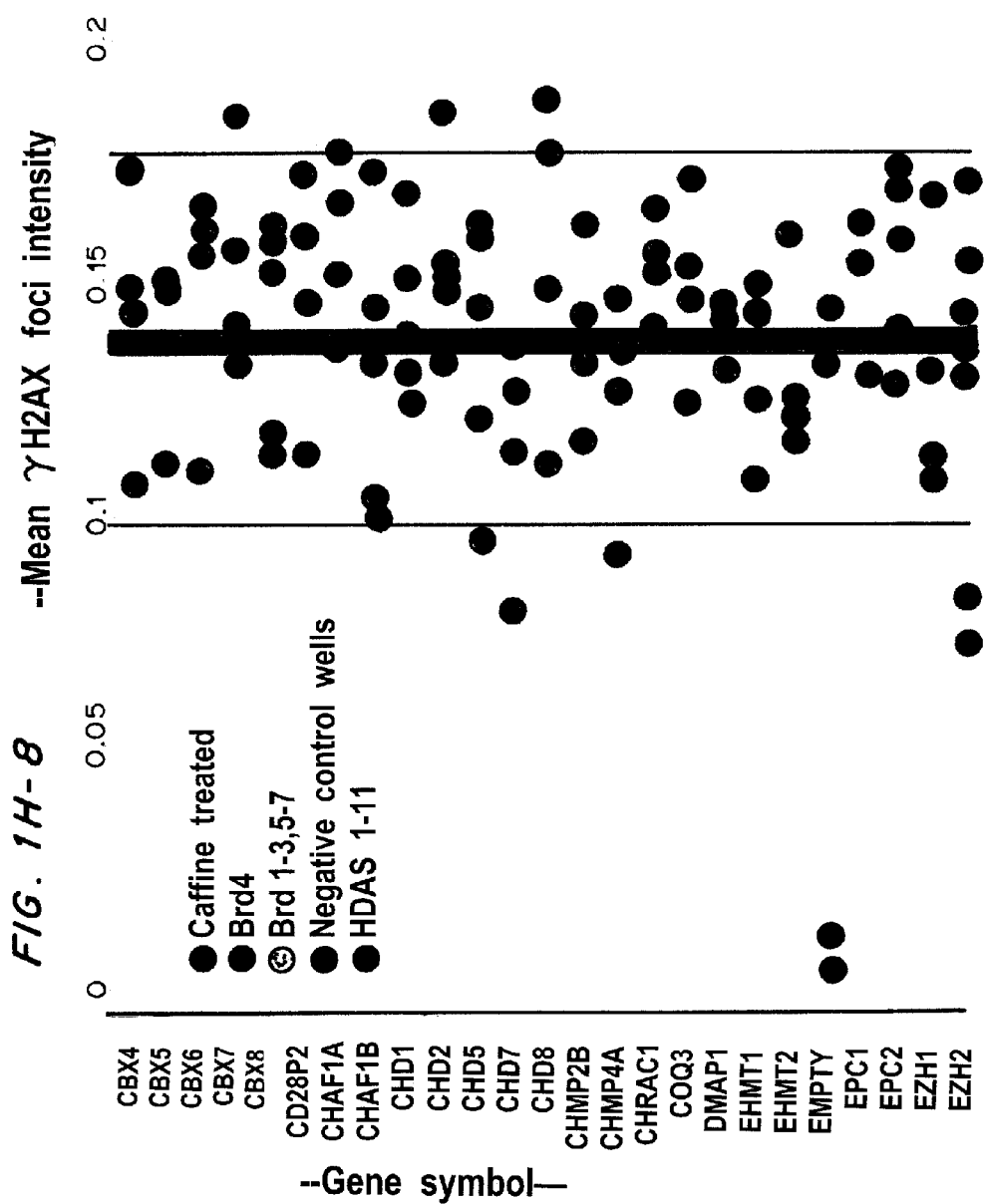

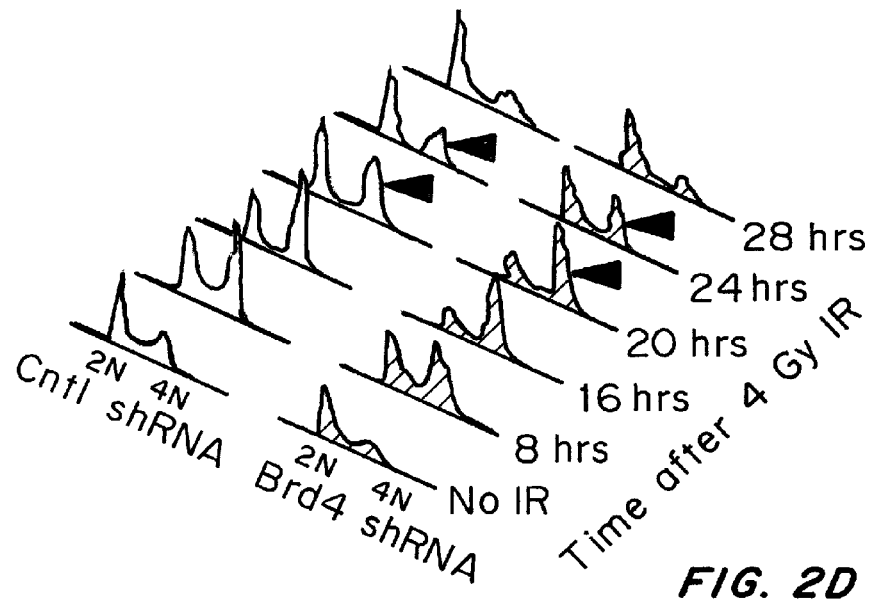
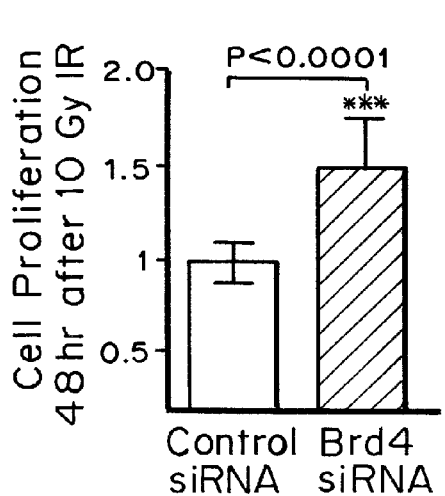
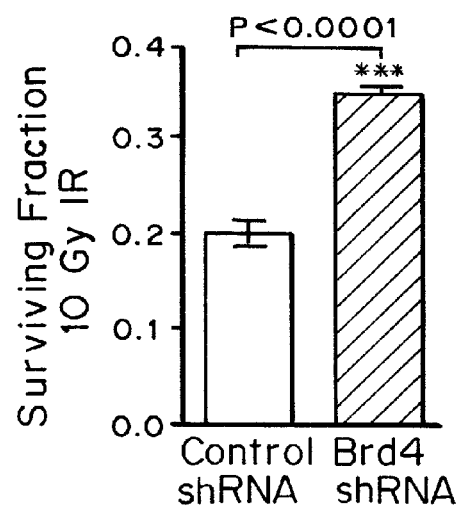
FIG. 2D
FIG. 2E
FIG. 2F

FIG. 6A-2

```
PDE4B
ZDHHC11
C5orf54
BRD4
GPRC5B
SRRT
SDPR
DNA2
CHEK2
ZFHX4
CNTN1
ECM1
CEP110
ATHL1
RDH11
C6orf26
MAP1A
```

```
CLC2
SPANXA1
SPANXB1
SPANXB2
SPANXC
SPANXF1
PSG4
SLC35F5
LOC441B01
KIAA0415
FGF5
KIAA1609
LEPR
HSD17B14
PTX3
DLGAP4
IL32
BAMBI
SEPP1
HIST1H3H
GLS
```

COMPOSITIONS AND METHODS FOR MODULATING BRD4 BIOACTIVITY

CROSS-REFERENCE TO RELATED APPLICATIONS

This application claims benefit of and priority to U.S. Provisional Application No. 61/672,964, filed Jul. 18, 2012, which is herein incorporated by reference in its entirety.

STATEMENT REGARDING FEDERALLY SPONSORED RESEARCH OR DEVELOPMENT

This invention was made with government support under Grant No. NS063917 awarded by the National Institutes of Health. The government has certain rights in the invention.

REFERENCE TO SEQUENCE LISTING

The Sequence Listing submitted Oct. 23, 2013 as a text file named "MIT 15011_2_ST25 created on Sep. 20, 2016 and having a size of 41,715 bytes is hereby incorporated by reference pursuant to 37 C.F.R. §1.52(e)(5).

FIELD OF THE INVENTION

The application is generally related to compositions and methods for modulating cellular responses to DNA damage.

BACKGROUND OF THE INVENTION

Treating cancer can be difficult in part because tumor cells can hijack normal cellular processes to resist treatment. For example, tumor cells can survive DNA damage that is induced by chemotherapeutic treatments by using normal cellular DNA repair pathways. Inhibitors of specific DNA repair pathways have been suggested as potential cancer treatments that could be used in combination with DNA-damaging chemotherapeutic therapies (Helleday, T., et al., *Nature Reviews Cancer*, 8, 193-204 (2008)). Unfortunately, the mechanisms underlying DNA repair pathways have not been fully elucidated.

The detection and repair of damaged DNA takes place in the context of chromatin. A variety of histone modifications including phosphorylation, acetylation, sumolation, and ubiquitylation are involved in the signaling events that trigger and transduce the DNA damage response (DDR) (T. Misteli, et al., *Nat. Rev. Mol. Cell Biol.*, 10:243 (2009); H. van Attikum, et al., *Trends Cell Biol.*, 19:207 (2009); J. W. Harper, et al., *Mol. Cell*, 28:739 (2007)). The DDR blocks cell cycle progression, recruits factors involved in DNA repair, and optionally triggers programs that control senescence or programmed cell death (S. P. Jackson, et al., *Nature*, 461:1071 (2009)). Although alterations in chromatin structure are known to be important for the initiation and propagation of the DNA damage response, the molecular details of these alterations are unclear. For example, histone acetylation is known to regulate chromatin dynamics (K. K. Lee, et al., *Nat. Rev. Mol. Cell Biol.*, 8:284 (2007); R. Margueron, et al., *Nat. Rev. Genet.*, 11:285 (2010)), but the mechanistic role of histone acetylation in the DDR is poorly understood (H. van Attikum, et al., *Trends Cell Biol.*, 19:207 (2009); C. Das, et al., *Nature*, 459:113 (2009); J. Tjeertes, et al., *EMBO J.*, 12 (2009)).

Therefore, it is an objection of the invention to provide compositions and methods for treating cancer by modulating the DDR in target cells, preferably cancer or precancerous cells.

It is also an object of the invention to provide compositions and methods for sensitizing tumor cells to DNA damaging agents such as ionizing radiation.

It is also an object of the invention to provide compositions and methods for protecting healthy cells from DNA damaging agents.

It is a further object of the invention to provide methods of determining whether cells will be sensitive to DNA damaging agents.

It is another object of the invention to provide methods for identifying agents that interfere with the DRR in specific cells or tissues.

SUMMARY OF THE INVENTION

Compositions and methods for modulating the bioactivity of Brd4 protein, specifically Brd4 isoform B, are provided. It has been discovered that Brd4 isoform B is a check point regulator of the DNA repair response (DRR). The methods and compositions described herein modulate Brd4 isoform B bioactivity to increase or promote DNA damage repair in cells or to inhibit or reduce DNA damage repair in cells. For example, increasing intracellular Brd4 isoform B bioactivity decreases the DRR, resulting in reduced DNA repair. Decreasing intracellular bioactivity of Brd4 isoform B increases the DRR, resulting in increased DNA damage repair.

The compositions and methods are useful for promoting or enhancing the death of specifically targeted cells, such as tumor cells, by up-regulating Brd4 bioactivity in the targeted cells. Other disclosed compositions and methods are useful for enhancing or promoting the ability of specifically targeted cells to repair DNA damage, for example, DNA damage resulting from chemotherapeutic agents by down-regulating Brd4 bioactivity in the targeted cells. It has been discovered that the Bromodomain containing protein Brd4, particularly Brd4 isoform B, specifically silences the DNA damage response at sites of DNA damage. Brd4 functions to limit the extent of signals that are sent from sites of DNA damage.

Exemplary agents or compositions for modulating Brd4 bioactivity include Brd4 polypeptides, fragments, fusion proteins thereof or variant proteins thereof. The fusion proteins can include a protein transduction domain, a targeting domain, or a combination thereof to enhance transport of the fusion protein across lipid membranes, for example across the plasma membrane or organelle membrane of a cell. In some embodiments the fusion protein maintains or mimics the endogenous activity of an endogenous Brd4 polypeptide, for example Brd4 isoform B.

In some embodiments, the fusion protein competes with endogenous Brd4 for targets of Brd4 in the DNA damage repair response mediated signal transduction pathway. In some embodiments, the agents competitively inhibit endogenous Brd4 by binding to Brd4 or targets of Brd4 without propagating DNA damage repair response mediated signal transduction.

Other exemplary agents and compositions include inhibitory nucleic acids that specifically inhibit expression of nucleic acids that encode Brd4 isoform B protein or a precursor thereof. Nucleic acids that encode B4d4 isoform B or a precursor thereof include mRNA and genomic DNA. In some embodiments the inhibitory nucleic acid specifically binds to a portion of Brd4 isoform B mRNA that is absent on Brd4 isoform A mRNA and Brd4 isoform C mRNA and inhibits the translation of the Brd4 isoform B mRNA.

Additional agents and compositions include an antibody or antigen binding fragment thereof that specifically binds an epitope on Brd4 isoform A, Brd4 isoform B, Brd4 isoform C, or a combination thereof. Typically, the antibody or antigen binding fragment thereof binds to an epitope on Brd4 isoform B that is masked or absent on Brd4 isoform A and Brd4 isoform C. Binding of the antibody to Brd4 isoform B inhibits or reduces the bioactivity of Brd4 isoform B and increases DNA damage repair response mediated signal transduction.

Small molecules that specifically reduce the bioavailability of Brd4 isoform A, Brd4 isoform B, Brd4 isoform C, or a combination thereof, such as (+)JQ1, are disclosed. Methods of identifying additional small molecules that increase or decrease the bioavailability of one or more Brd4 isoforms are also disclosed. The small molecules may be useful for inhibiting or promoting DNA damage repair response mediated signal transduction, respectively.

Methods to increase the sensitivity of tumor cells to DNA damaging agents such as ionizing radiation and chemotherapy include administering an agent to the cells in an amount effective to inhibit or reduce DNA damage repair response mediated signal transduction.

Methods for enhancing DNA damage signaling, prolonging cell cycle arrest after DNA damage, increasing DNA damage repair, and increasing cell survival after genotoxic stress can be achieved by down-regulating intracellular Brd4 bioactivity, preferably Brd4 isoform B bioactivity. Down-regulating Brd4 bioactivity includes decreasing or reducing the bioavailability of one or more isoforms of Brd4, particularly Brd4 isoform B. For example, compounds that inhibit Brd4 binding to other proteins or nucleic acids or sequester Brd4 can serve as a DNA damage protective agents.

Methods of treating cancer include increasing the sensitivity of cancer cells to a DNA damaging agent by contacting the cancer cells with an effective amount of an agent or compound that increases the bioavailability of one or more Brd4 isoforms, preferably Brd4 isoform B, to decrease DNA damage repair in the cancer cells following treatment of the cancer cells with the agent or compound in combination or alternation with the DNA damaging agent. The agent or compound is administered in an effective amount to decrease a DNA damage response, for example, reduce $\gamma$H2AX foci number, reduce $\gamma$H2AX foci size, reduce $\gamma$H2AX foci intensity, reduce $\gamma$H2AX-mediated signaling, reduce G2/M growth arrest, decrease cell survival, or decrease proliferation. In some embodiments, the compounds are administered in combination with the cancer therapy, for example, in a coating on brachytherapy beads, to increase efficacy of the radiation at the site of implantation, allowing a lower dosage or shorter radioactive half-life to be used while minimizing toxicity of the radiation.

The bioavailability of Brd4 isoform B can be increased by increasing the level of a Brd4 mRNA or Brd4 polypeptide, fragment, fusion or variant thereof in the cell. In some embodiments, the bioavailability of Brd4 isoform B is increased by decreasing the bioavailability of Brd4 isoform A mRNA or polypeptide, Brd4 isoform C mRNA or polypeptide, or combinations thereof.

The ratio of intracellular Brd4 protein isoforms can be adjusted to increase DNA repair or to inhibit DNA repair as needed in the targeted cell. For example, the ratio of Brd4 isoform B to other Brd4 isoforms is typically adjusted to be greater than 1.0 when inhibition of DNA repair is desired in the target cell. The ratio of Brd4 isoform B compared to other isoforms of Brd4 is less than 1.0 when enhancing or promoting DNA repair is desired.

Methods of protecting cells from DNA damage or enhancing the survivability of cells exposed to a DNA damaging agent include contacting the cells with an effective amount of a compound that decreases the bioavailability of one or more Brd4 isoforms. Typically, the cells are healthy, non-tumor or non-cancerous cells. In some embodiments, the compound is administered in an effective amount to increase DNA damage response in the cell, for example, to increase $\gamma$H2AX foci number, increase $\gamma$H2AX foci size, increase $\gamma$H2AX foci intensity, increase $\gamma$H2AX-mediated signaling, increase G2/M growth arrest, increase cell survival, or increase proliferation. The bioactivity of one, two, or all three isoforms of Brd4 are decreased to enhance DNA repair. In certain embodiments, the bioactivity of Brd4 isoform B alone or in combination with at least one other Brd4 isoform is decreased. These compounds can be administered into normal tissue in the area adjacent to that being treated for cancer, to enhance survival of the normal healthy cells. This may be by injection or sustained release depo or microparticles.

Assaying the levels of Brd4 isoform B expression in cancer cells obtained from a patient can be used to determine which patients will have a good response to radiation treatment (the current standard of care), or to other DNA damaging agents for treating their cancer. For example, an equal or elevated level of Brd4 isoform B polypeptide in the cancer cells relative to a control is indicative that the cancer cells are sensitive to a DNA damaging agent and the patient will likely have a good response to radiation treatment. A reduced level of Brd4 isoform B polypeptide in the sample relative to the control is indicative that the cancer cells are insensitive to the DNA damaging agent and the patient will likely not have a good response to radiation treatment. The level of Brd4 isoform B polypeptide can be determined by analyzing protein isolated from target cells, for example by immunoassay, radioassay, western blot, ELISA, protein staining, or mass spectrometry, or by staining the cells for Brd4 isoform B polypeptide expression. Also provided are kits that include reagents used to determine if cells are sensitive to a DNA damaging agent.

Compounds which inhibit Brd4 isoform B polypeptide expression or activity can also be used to limit overproliferation of normal cells, for example, overproliferation of fibroblasts leading to scar formation and overproliferation of endothelial cells leading to restenosis, since proliferating cells have an increase in DNA repair and inhibition of DNA repair should reduce overproliferation. The compound can be administered in an implant or coating thereon, with sustained or controlled release following implantation. Preferred examples include vascular stents or grafts. The compounds can also be used as a wound dressing to decrease scarring.

BRIEF DESCRIPTION OF THE DRAWINGS

FIG. 1A is a diagram exemplifying a high throughput time-dependent multiplex image-based screen for identifying modulators of the DDR. Six images per well were obtained by automated microscopy, cells were identified by custom image analysis software, and examined for DNA content (Hoechst stain), early DDR signaling ($\gamma$H2AX antibodies), mitotic entry (phospho-histone H3, (pHH3) antibodies) and apoptosis (cleaved caspase 3 (CC3) antibodies). FIG. 1B are histograms showing the results of cell cycle analysis. DNA content measured by the quantitative microscopy algorithm were used to generate cell cycle profiles, shown following treatment with either caffeine or the indicated negative (GFP) and positive (ATR) control shRNAs. FIG. 1C is a dot plot showing mean number of γH2AX foci number per nucleus as function of time.

FIG. 2D are histograms showing the DNA content of control and Brd4 shRNA treated U2OS cells exposed to 4 Gy ionizing radiation. Arrowheads indicate prolonged G2 arrest at 20-24 hours after IR in Brd4 knockdown cells. FIG. 2E is a bar graph showing cell proliferation of control and Brd4 siRNA knockdown cells 48 hours after exposure to 10 Gy ionizing radiation (IR) (* $p<0.0001$). Cell proliferation after IR was normalized to unirradiated cells and is shown relative to control. FIG. 2F is a bar graph showing surviving fraction of control and Brd4 shRNA knockdown cells in a colony formation assay 2 weeks after exposure to 10 Gy IR (* $p<0.0001$). Error bars in (2E) and (2F) show standard deviation of three independent experiments. P-values were calculated using the two-tailed student's t test.

DETAILED DESCRIPTION OF THE INVENTION

Figure 1D:
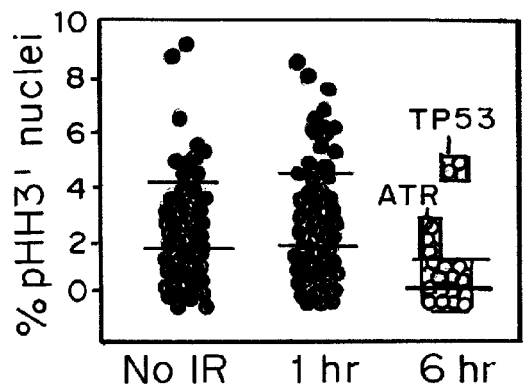
FIG. 1D is a dot plot showing the percentage of pHH3-positive nuclei as a function of time.
Figure 1E:
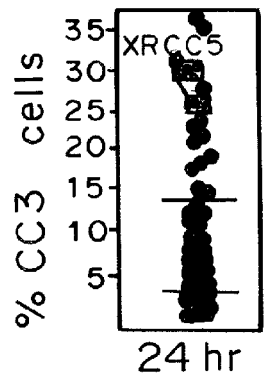
FIG. 1E is a dot plot showing the percentage of CC3-positive cells as a function of time. Thick bars represent mean values and thin bars represent S.D. of the mean. Effects of specific positive control target gene knockdowns (ATM, ATR, PP2CA, BRCA2, TP52, XRCC5) and caffeine are indicated.
Figure 1F:
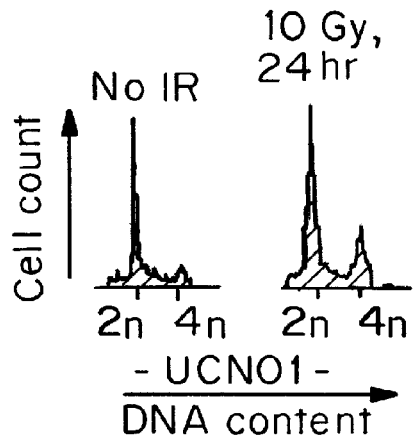
FIG. 1F is a histogram showing cell count of control (No IR) and irradiated (10 Gy) U2OS cells as function of DNA content following exposure to 36 nM UCN01, a potent inhibitor of the cell cycle checkpoint kinases Chk1 and MK2.
Figure 1G:
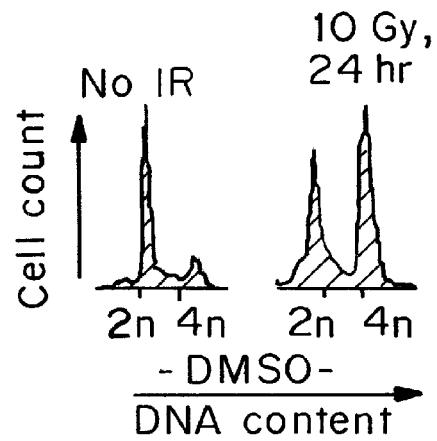
FIG. 1G is a histogram showing cell count of control (No IR) and irradiated (10 Gy) U2OS cells as function of DNA content following exposure to DMSO. FIG. H-1 through H-9 is a dot plot showing one hour time-point foci intensity scores from individual hairpins directed against the indicated genes from the screen preformed as outlined in FIG. 1A.
Figures 1, 1H:
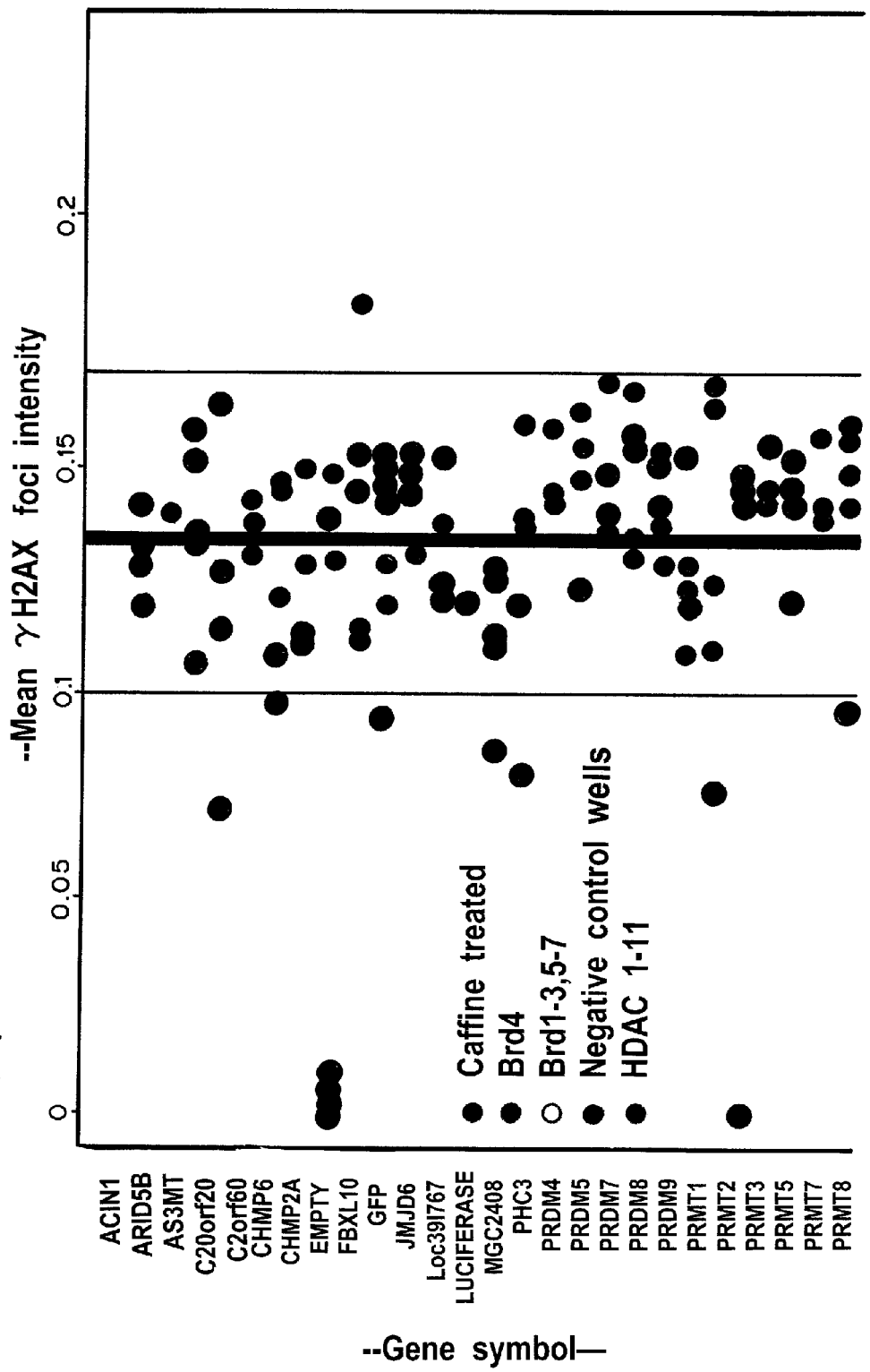
FIG. 6A-1 through 6A-2 is a plot showing fold expression change in of the listed mRNAs in Brd4 knockdown cell relative to control hairpin cell on Y-axis on log 2 scale and unadjusted p-value on X axis.
Figures 1, 1H, 2, 3:
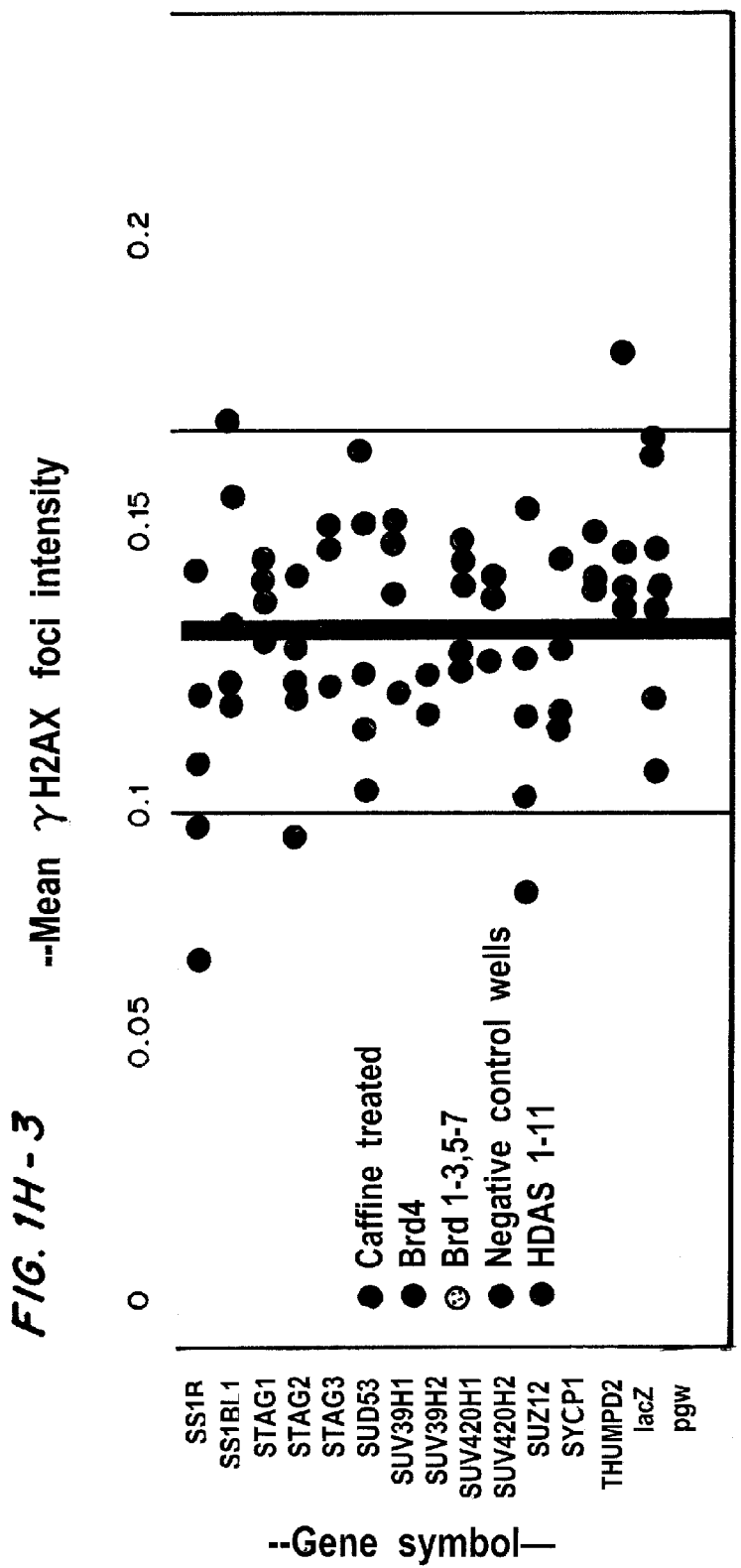

It has been discovered that alteration of the bioactivity of Brd4, in particular Brd4 isoform B, in cells can be used to inhibit or increase DNA damage repair in cells. By modulating DNA damage repair in specific cells, it is possible to increase or decrease the sensitivity of these cells to DNA damaging agents such as ionizing radiation. Increasing DNA damage repair in certain cells is desirable when survival of those cells is important. For example, increasing DNA damage repair in healthy cells exposed to DNA damaging agents such as ionizing radiation is important to enhance survival of healthy cells and tissue in a patient undergoing treatment for cancer. Decreasing DNA damage repair in cancer or tumor cells is useful to promote death of the cancer or tumor cells particularly when the cancer or tumor cells are exposed to a DNA damaging agent.

The data in Examples 1-5 and FIGS. 1-7 show that Brd4, a double bromodomain-containing protein, functions as an endogenous inhibitor of DNA damage signaling by binding to acetylated histones at sites of open chromatin and altering chromatin accessibility. Loss of Brd4 or disruption of acetyl-lysine binding results in an increase in both the number and size of radiation-induced γH2AX nuclear foci while over-expression of a Brd4 splice isoform, Brd4 isoform B, completely suppresses γH2AX formation, despite equivalent double strand break formation. Brd4 knockdown cells displayed altered chromatin structure, prolonged cell cycle checkpoint arrest and enhanced survival after irradiation, while overexpression of Brd4 isoform B results in enhanced radiation induced lethality. These data demonstrate that Brd4 is an endogenous insulator of DNA damage signaling through recognition of epigenetic modifications in chromatin.

Compositions and methods for modulating DNA repair in cells by modulating the bioactivity of one or more Brd4 isoforms, particularly Brd4 isoform B, are disclosed. Increasing the bioactivity of one or more isoforms of Brd4, particular the level of Brd4 isoform B, in cells reduces the ability of the cells to repair DNA damage which leads to cell death. Compositions and methods for treating cancer by increasing the bioavailability of one or more isoforms of Brd4, particularly Brd4 isoform B in cells, are also disclosed. The compositions and methods can be used, for example, to increase the cancer cells' sensitivity to a dose of a DNA damaging agent such as ionizing radiation.

Alternatively, decreasing the bioactivity of one or more isoforms of Brd4 in cells increases or enhances DNA repair in the cells resulting in the ability of the cells to withstand exposure to DNA damaging agents. Compositions and methods for protecting cells from DNA damaging agents by decreasing the bioactivity of one or more isoforms of Brd4, particularly Brd4 isoform B, in cells are also disclosed. The compositions and methods can be used, for example, to protect normal cells from a DNA damaging agent such as UV radiation from the sun.

I. DEFINITIONS

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences.

As used herein, an "expression control sequence" is a DNA sequence that controls and regulates the transcription and/or translation of another DNA sequence.

The term "polypeptides" includes proteins and fragments thereof. Polypeptides are as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Since it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly when the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations include at least one amino acid deletion, substitution, including conservative and non-conservative substitution, or insertion, wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from the total number of amino acids in the reference polypeptide.

As used herein, the term "low stringency" refers to conditions that permit a polynucleotide or polypeptide to bind to another substance with little or no sequence specificity.

As used herein, the term "purified" and like terms relate to the isolation of a molecule or compound in a form that is substantially free (at least 60% free, preferably 75% free, and most preferably 90% free) from other components normally associated with the molecule or compound in a native environment. As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "treating" includes alleviating the symptoms associated with a specific disorder or condition and/or preventing or eliminating the symptoms.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, the term "host cell" refers to prokaryotic and eukaryotic cells into which a recombinant vector can be introduced.

As used herein, "transformed" and "transfected" encompass the introduction of a nucleic acid (e.g. a vector) into a cell by a number of techniques known in the art.

As used herein, the phrase that a molecule "specifically binds" or "displays specific binding" to a target refers to a binding reaction which is determinative of the presence of the molecule in the presence of a heterogeneous population of other biologics.

Under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

The terms "individual", "host", "subject", and "patient" are used interchangeably herein, and refer to a mammal, including, but not limited to, humans, rodents, such as mice and rats, and other laboratory animals.

As used herein, the term "cell surface marker" refers to any molecule such as moiety, peptide, protein, carbohydrate, nucleic acid, antibody, antigen, and/or metabolite presented on the surface or in the vicinity of a cell sufficient to identify the cell as unique in either type or state.

"Protein Transduction Domain" or PTD refers to a polypeptide, polynucleotide, carbohydrate, or organic or inorganic compounds that facilitate traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. Exemplary PTDs include, but are not limited to, HIV TAT YGRKKRRQRRR (SEQ. ID NO. 12) or RKKRRQRRR (SEQ. ID NO. 13); 11 Arginine residues, or positively charged polypeptides or polynucleotides having 8-15 residues, preferably 9-11 residues.

The "bioactivity" of one or more isoforms of Brd4 refers to the biological function of the Brd4 polypeptide. Bioactivity can be increased or reduced by increasing or reducing the activity of basal levels of polypeptide, increasing or reducing the avidity of basal levels of polypeptide, the quantity of the polypeptide, the ratio of one isoform of the polypeptide relative to another isoform of the polypeptide, increasing or reducing the expression levels of the polypeptide, or a combination thereof. For example, bioavailable Brd4 polypeptide is a polypeptide that can be localized to chromatin and is capable of binding to acetylated histones. Brd4 polypeptide that is not bioavailable includes Brd4 polypeptide that is mis-localized or in-capable of binding to acetylated histones. The Brd4 polypeptide can be an endogenous Brd4 polypeptide or recombinant Brd4 polypeptide, fusion protein, or fragment or variant thereof.

II. COMPOSITIONS FOR MODULATING BRD4 ACTIVITY

It has been discover that the Bromodomain containing protein Brd4, particularly isoform B, specifically silences the DNA damage response at sites of DNA damage. Brd4 functions as an endogenous inhibitor of DNA damage signaling, but does not appear to significantly alter the amount of DNA damage that is caused by treatments such as ionizing radiation. In normal cells, this means that Brd4 functions to limit the extent of signals that are sent from sites of DNA damage. Conversely, down-regulation of Brd4 results in enhanced DNA damage signaling, a prolonged cell cycle arrest after damage, and increased cell survival after genotoxic stress.

A. Brd4

The compositions include compounds that increase or decrease the bioavailability of one or more isoforms of Brd4. Bromodomain-containing protein 4 (Brd4) belongs to the BET (bromodomains and extraterminal) family that includes mammalian Brd2, Brd3, Brd4, Brdt, *Drosophila* Fsh, yeast Bdf1, Bdf2, and corresponding homologues in other species. Brd4, also referred to as MCAP (mitotic chromosome-associated protein; Dey, et al., *Mol. Cell. Biol.*, 20, 6537-6549 (2000)), Fshrg4, and Hunk1, is a chromatin binding factor with preference for acetylated Lys-14 on histone H3 and Lys-5/12 on H4 (Dey, A., et al., *Proc. Natl. Acad. Sci.*, U.S.A., 100:8758-8763 (2003)). Brd4 has been implicated in wide range of cellular processes including cellular growth, cell cycle control, DNA replication, and gene rearrangement found in t(15;19)-associated carcinomas.

Brd4 contains two tandem bromodomains (BDI and BDII), a conserved sequence motif which may be involved in chromatin targeting, and an extraterminal (ET) domain (Florence, B., and Faller, D. V., *Front. Biosci.* 6:D1008-1018 (2001)). The bromodomains are conserved regions of about 110 amino acids that structurally form 4 α-helices (αz, αA, αB, and αC) and 2 loops, linking αz and αA (ZA loop) and αB and αC (BC loop) (Zeng, and Zhou, *FEBS Lett.*, 513, 124-128 (2002)). One or both of the bromodomains mediate binding of Brd4 to acetylated histones.

B. Compositions for Increasing the Bioactivity of Brd4

Compositions including one or more compounds for increasing the bioactivity of one or more isoforms of Brd4 are disclosed. In some embodiments, the compound is a Brd4 polypeptide, a fusion protein including a Brd4 polypeptide, an isolated nucleic acid encoding a Brd4 polypeptide or Brd4 fusion protein, or an agent such as a transcription factor that increases endogenous expression of a Brd4 polypeptide. Up regulation of Brd4, particularly isoform B, blocks signaling from DNA damage, and results in increased cell death. Thus, therapies that up-regulate Brd4 isoform B expression can be used to increase the sensitivity of cells, for example, cancer cells, to DNA damaging agents such as ionizing radiation and chemotherapy.

1. Brd4 Polypeptides

In some embodiments a composition for increasing the bioactivity of Brd4 includes a Brd4 polypeptide. There are three known isoforms of Brd4, isoform A, also referred to as the "long form," isoform B, and isoform C, also referred to as the "short form,". It is believed these isoforms are produced by alternative splicing.

Nucleic acid and amino acid sequences for Brd4 isoform A are known in the art. See for example, Genbank Accession No. NM_058243.

A composition for increasing the bioavailability of Brd4 can include a polypeptide having this sequence, a sequence having at least 80%, 85%, 90%, 95%, 99%, or 100% sequence identity to this sequence, or a fragment or variant thereof.

Nucleic acid and amino acid sequences for Brd4 isoform B are also known in the art. See for example, Genbank Accession No. BC035266.1, which provides Brd4 isoform B amino acid sequence (SEQ ID NO:22) and nucleic acid sequence (SEQ ID NO:23). A composition for increasing the bioactivity of Brd4 can include a polypeptide having a sequence having at least 80%, 85%, 90%, 95%, 99%, or 100% sequence identity to isoform B, or a fragment or variant thereof.

Nucleic acid and amino acid sequences for Brd4 isoform C are also known in the art. See for example, Genbank Accession No. NM_014299.2. A composition for increasing the bioactivity of Brd4 can include a polypeptide having this sequence, a sequence having at least 80%, 85%, 90%, 95%, 99%, or 100% sequence identity to isoform C, or a fragment or variant thereof.

All three isoforms of Brd4 are conserved over the first 719 amino acids beginning at the N-terminal methionine. isoforms A, B, and C all contain two bromodomains, and an ET domain. The first bromodomain (BDI) is from about amino acid 75 to about amino acid 147 beginning from the N-terminal methionine of the above-identified sequences. For example, in some embodiments, BDI includes the amino acid sequence:

```
                                                         (SEQ ID NO: 1)
WKHQFAWPFQ QPVDAVKLNL PDYYKIIKTP MDMGTIKKRL ENNYYWNAQE CIQDFNTMFT

NCYIYNKPGD DIV.
```

A composition for increasing the bioactivity of Brd4 can include a polypeptide having the sequence of SEQ ID NO:1, a sequence having at least 80%, 85%, 90%, 95%, 99%, or 100% sequence identity SEQ ID NO:1, or a functional fragment or variant thereof.

The second bromodomain (BDII) is from about amino acid 368 to about amino acid 440 beginning from the N-terminal methionine of the above-identified sequences. For example, in some embodiments, BDII includes the amino acid sequence:

```
                                                           (SEQ ID NO: 2)
KHAAYAWPFY KPVDVEALGL HDYCDIIKHP MDMSTIKSKL EAREYRDAQE FGADVRLMFS

NCYKYNPPDH EVV.
```

A composition for increasing the bioactivity of Brd4 can include a polypeptide having a sequence having at least 80%, 85%, 90%, 95%, 99%, or 100% sequence identity SEQ ID NO:2, or a fragment or variant thereof.

Iso forms B and C are shorter than isoform A. Isoform B differs from both isoforms A and C at its C-terminus. Isoform B contains the C-terminal sequence:

```
                                                           (SEQ ID NO: 3)
AFCTSGDFVS PGPSPYHSHV QCGRFREMLR WFLVDVEQTA AGQPHRQSAA GPAITWAPAI

AYPSPECARC CVGCS,
``` which is absent from isoforms A and C.

In a preferred embodiment, the composition for increasing the bioactivity of Brd4 includes a polypeptide that has the functional activity of isoform B. For example, in some embodiments, the composition includes a polypeptide including the amino acid sequence of SEQ ID NO:3, a sequence having at least 80%, 85%, 90%, 95%, 99%, or 100% sequence identity SEQ ID NO:3, or a fragment or variant thereof.

A number of naturally occurring variants are also known in the art, and include, but are not limited to, substitutions at one or more of amino acids 37, 371, 563, 598, and 669 beginning from the N-terminal methionine of the above-identified sequences, and amino acid 1097 of the above-identified sequences. Useful variants include those that increase biological activity, as indicated by any of the assays described herein, or that increase half life or stability of the protein. The Brd4 polypeptides and Brd4 fragments, or fusions thereof having Brd4 activity, can be engineered to increase biological activity. In a preferred embodiment, the Brd4 polypeptide or fusion protein has been modified with at least one amino acid substitution, deletion, or insertion that increases the binding of the molecule to acetylated histones. Other variants of Brd4 can be engineered to have reduced binding to acetylated histones compared to a wild-type Brd4 isoform. These variants can be used in combination with variants having stronger binding properties to modulate the binding of Brd4 polypeptides to acetylated histones.

Variant Brd4 polypeptides can be engineered to have an increased half-life relative to wildtype. These variants typically are modified to resist enzymatic degradation. Exemplary modifications include modified amino acid residues and modified peptide bonds that resist enzymatic degradation. Various modifications to achieve this are known in the art. The variants can be modified to adjust for effects of the half life of Brd4 polypeptides, fragments, or fusions thereof at serum and endosomal pH.

2. Brd4 Fusion Proteins

Fusion proteins containing one or more of the Brd4 polypeptides disclosed above can be coupled to other polypeptides to form fusion proteins. Brd4 fusion polypeptides have a first fusion partner comprising all or a part of a Brd4 protein fused (i) directly to a second polypeptide or, (ii) optionally, fused to a linker peptide sequence that is fused to the second polypeptide. The fusion proteins optionally contain a domain that functions to dimerize or multimerize two or more fusion proteins. The peptide/polypeptide linker domain can either be a separate domain, or alternatively can be contained within one of the other domains (Brd4 polypeptide or second polypeptide) of the fusion protein. Similarly, the domain that functions to dimerize or multimerize the fusion proteins can either be a separate domain, or alternatively can be contained within one of one of the other domains (Brd4 polypeptide, second polypeptide or peptide/polypeptide linker domain) of the fusion protein. In one embodiment, the dimerization/multimerization domain and the peptide/polypeptide linker domain are the same.

Fusion proteins are of formula I:

$$N-R_1-R_2-R_3-C$$

wherein "N" represents the N-terminus of the fusion protein, "C" represents the C-terminus of the fusion protein, "$R_1$" is a Brd4 polypeptide, "$R_2$" is an optional peptide/polypeptide linker domain, and "$R_3$" is a second polypeptide. Alternatively, $R_3$ may be the Brd4 polypeptide and $R_1$ may be the second polypeptide.

The fusion proteins can be dimerized or multimerized. Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

a. Second Polypeptide

The Brd4 polypeptide can be fused to a second polypeptide. The presence of the second polypeptide can alter the solubility, stability, affinity and/or valency of the Brd4 fusion polypeptide. As used herein, "valency" refers to the number of binding sites available per molecule. In one embodiment the second polypeptide is a polypeptide from a different source or different protein.

i. Brd4-NUT

In one embodiment, the Brd4 fusion protein is the naturally occurring Brd4-NUT fusion protein or a functional fragment or variant thereof. Brd4 is a target of the t(15;19) chromosomal translocation in the rare human epithelial carcinoma NUT Midline Carcinoma (NMC), which creates a fusion protein referred as Brd4-NUT. NMC is a highly aggressive cancer with a poor prognosis. Reports indicate that the only effective treatments include radiation therapy as part of a multi-modality approach (J. Engleson, et al., *BMC Cancer*, 6:69 (2006); F. Mertens, et al., *Pediatr Blood Cancer*, 49:1015 (2007); G. Santis, et al., *Journal of clinical* oncology: official journal of the American Society of Clinical Oncology, (2011)). The expressed fusion protein from the t(15;19) translocation places NUT (Nuclear Protein in Testis) at the same site as the unique 73 amino acid insert in Brd4 isoform B.

Nucleic acid and amino acid sequences for Brd4-NUT are known in the art. See for example, Genbank Accession No. AY166680.1, which provides Brd4-NUT amino acid sequence (SEQ ID NO:24) and nucleic acid sequence (SEQ ID NO:25).

In a preferred embodiment, the composition for increasing the bioactivity of Brd4 includes a fusion protein, such as Brd4-NUT, that has the functional activity of Brd4 isoform B. For example, in some embodiments, the composition includes a fusion protein including the amino acid sequence of the above-identified sequence, a sequence having at least 80%, 85%, 90%, 95%, 99%, or 100% sequence identity to the above-identified sequence, or a fragment or variant thereof.

ii. Brd4-Ig

In some embodiment the Brd4 fusion protein is a Brd4-Ig fusion protein. In one embodiment, the second polypeptide contains one or more domains of an immunoglobulin heavy chain constant region, preferably having an amino acid sequence corresponding to the hinge, $C_H2$ and $C_H3$ regions of a human immunoglobulin Cγ1 chain or to the hinge, $C_H2$ and $C_H3$ regions of a murine immunoglobulin Cγ2a chain.

In a preferred dimeric fusion protein, the dimer results from the covalent bonding of Cys residue in the hinge region of two of the Ig heavy chains that are the same Cys residues that are disulfide linked in dimerized normal Ig heavy chains.

In one embodiment, the immunoglobulin constant domain may contain one or more amino acid insertions, deletions or substitutions that enhance binding to specific cell types, increase the bioavailability, or increase the stability of the Brd4 fusion proteins, or fragments thereof. Suitable amino acid substitutions include conservative and non-conservative substitutions, as described above.

In another embodiment the second polypeptide may have a conjugation domain through which additional molecules can be bound to the Brd4 fusion proteins. In one such embodiment, the conjugated molecule is capable of targeting the fusion protein to a particular organ or tissue. In another such embodiment the conjugated molecule is another immunomodulatory agent that can enhance or augment the effects of the Brd4 fusion protein. In another embodiment the conjugated molecule is Polyethylene Glycol (PEG).

The Fc portion of the fusion protein may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see, for example, Mueller, et al., *Mol. Immun.*, 34(6):441-452 (1997), Swann, et al., *Cur. Opin. Immun.*, 20:493-499 (2008), and Presta, *Cur. Opin. Immun.* 20:460-470 (2008). In some embodiments the Fc region is the native IgG1, IgG2, or IgG4 Fc region. In some embodiments the Fc region is a hybrid, for example, a chimeric including IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region may include the entire hinge region, or less than the entire hinge region.

The therapeutic outcome in patients treated with rituximab (a chimeric mouse/human IgG1 monoclonal antibody against CD20) for non-Hodgkin's lymphoma or Waldenstrom's macroglobulinemia correlated with the individual's expression of allelic variants of Fcγ receptors with distinct intrinsic affinities for the Fc domain of human IgG1. In particular, patients with high affinity alleles of the low affinity activating Fc receptor CD16A (FcγRIIIA) showed higher response rates and, in the cases of non-Hodgkin's lymphoma, improved progression-free survival. In another embodiment, the Fc domain may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA).

Another embodiment includes IgG2-4 hybrids and IgG4 mutants that have reduced binding to FcR which increase their half life. Representative IG2-4 hybrids and IgG4 mutants are described in Angal, S. et al., *Molecular Immunology*, 30(1):105-108 (1993); Mueller, J. et al., *Molecular Immunology*, 34(6): 441-452 (1997); and U.S. Pat. No. 6,982,323 to Wang et al. In some embodiments the IgG1 and/or IgG2 domain is deleted for example, Angal et al. describe IgG1 and IgG2 having serine 241 replaced with a proline.

In a preferred embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, et al., *Cancer Res.*, 57(18):8882-90 (2007). Exemplary variants of human IgG1 Fc domains with reduced binding to CD32B and/or increased binding to CD16A contain F243L, R929P, Y300L, V305I or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297Q substitution, as this mutation abolishes FcR binding.

b. Peptide or Polypeptide Linker Domain

The disclosed Brd4 fusion proteins optionally contain a peptide or polypeptide linker domain that separates the Brd4 polypeptide from the second polypeptide. In one embodiment, the linker domain contains the hinge region of an immunoglobulin. In a preferred embodiment, the hinge region is derived from a human immunoglobulin. Suitable human immunoglobulins that the hinge can be derived from include IgG, IgD and IgA. In a preferred embodiment, the hinge region is derived from human IgG. Amino acid sequences of immunoglobulin hinge regions and other domains are well known in the art. Other suitable peptide/polypeptide linker domains include naturally occurring or non-naturally occurring peptides or polypeptides. Peptide linker sequences are at least 2 amino acids in length. Preferably the peptide or polypeptide domains are flexible peptides or polypeptides. A "flexible linker" herein refers to a peptide or polypeptide containing two or more amino acid residues joined by peptide bond(s) that provides increased rotational freedom for two polypeptides linked thereby than the two linked polypeptides would have in the absence of the flexible linker. Such rotational freedom allows two or more antigen binding sites joined by the flexible linker to each access target antigen(s) more efficiently. Exemplary flexible peptides/polypeptides include, but are not limited to, the amino acid sequences Gly-Ser, Gly-Ser-Gly-Ser (SEQ ID NO:4), Ala-Ser, Gly-Gly-Gly-Ser (SEQ ID NO:5), (Gly$_4$-Ser)$_3$ (SEQ ID NO:6) and (Gly$_4$-Ser)$_4$ (SEQ ID NO:7). Additional flexible peptide/polypeptide sequences are well known in the art.

c. Protein Transduction Domains

In some embodiments, the Brd4 fusion proteins include one or more domains for enhancing delivery of the polypeptide across the plasma membrane in into the interior of cells. The Brd4 fusion proteins can be modified to include a protein transduction domain (PTD), also known as cell penetrating peptides (CPPS). PTDs are known in the art, and include, but are not limited to, small regions of proteins that are able to cross a cell membrane in a receptor-independent mechanism (Kabouridis, P., *Trends in Biotechnology* (11): 498-503 (2003)). Although several of PTDs have been documented, the two most commonly employed PTDs are derived from TAT (Frankel and Pabo, *Cell*, 55(6):1189-93 (1988)) protein of HIV and Antennapedia transcription factor from *Drosophila*, whose PTD is known as Penetratin (Derossi et al., *J. Biol. Chem.*, 269(14):10444-50 (1994)). The Antennapedia homeodomain is 68 amino acid residues long and contains four alpha helices. Penetratin is an active domain of this protein which consists of a 16 amino acid sequence derived from the third helix of Antennapedia. TAT protein consists of 86 amino acids and is involved in the replication of HIV-1. The TAT PTD consists of an 11 amino acid sequence domain (residues 47 to 57; YGRKKRRQRRR (SEQ. ID. NO. 8)) of the parent protein that appears to be critical for uptake. Additionally, the basic domain Tat(49-57) or RKKRRQRRR (SEQ. ID NO. 9) has been shown to be a PTD. TAT has been favored for fusion to proteins of interest for cellular import. Several modifications to TAT, including substitutions of Glutatmine to Alanine, i.e., Q→A, have demonstrated an increase in cellular uptake anywhere from 90% (Wender et al., *Proc. Natl. Acad. Sci. USA.*, 97(24): 13003-8 (2000)) to up to 33 fold in mammalian cells. (Ho et al., *Cancer Res.*, 61(2):474-7 (2001)) The most efficient uptake of modified proteins was revealed by mutagenesis experiments of TAT-PTD, showing that an 11 arginine stretch was several orders of magnitude more efficient as an intercellular delivery vehicle. Thus, some embodiments include PTDs that are cationic or amphipathic. Additionally exemplary PTDs include, but are not limited to, poly-Arg-RRRRRRR (SEQ ID NO:8); PTD-5-RRQRRTSKLMKR (SEQ ID NO:9); Transportan GWTLNSAGYLLGKINL-KALAALAKKIL (SEQ ID NO:10); KALA-WEAKLAKA-LAKALAKHLAKALAKALKCEA (SEQ ID NO:11); and RQIKIWFQNRRMKWKK (SEQ ID NO:12).

In some embodiments, the fusion protein includes an endosomal escape sequence that improves delivery of the protein to the interior of the cell. Endosomal escape sequences are known in the art, see for example, Barka, et al., *Histochem. Cytochem.*, 48(11):1453-60 (2000) and Wadia and Stan, *Nat. Med.*, 10(3):310-5 (2004).

d. Targeting Signal or Domain

In some embodiments, the Brd4 fusion protein is optionally modified to include one or targeting signals or domains. The targeting signal or sequence can be specific for a host, tissue, organ, cell, organelle, an organelle such as the nucleus, or cellular compartment. Moreover, the compositions disclosed here can be targeted to other specific intercellular regions, compartments, or cell types.

In some embodiments, the targeting signal binds to a ligand or receptor which is located on the surface of a target cell such as to bring the fusion protein and cell membranes sufficiently close to each other to allow penetration of the fusion protein into the cell. Additional embodiments are directed to specifically delivering the fusion protein to specific tissue or cell types.

In a preferred embodiment, the targeting molecule is selected from the group consisting of an antibody or antigen binding fragment thereof, an antibody domain, an antigen, a cell surface receptor, a cell surface adhesion molecule, a viral envelope protein and a peptide selected by phage display that binds specifically to a defined cell.

Targeting domains to specific cells can be accomplished by modifying the disclosed fusion proteins to include specific cell and tissue targeting signals. These sequences target specific cells and tissues, but in some embodiments the interaction of the targeting signal with the cell does not occur through a traditional receptor:ligand interaction. The eukaryotic cell includes a number of distinct cell surface molecules. The structure and function of each molecule can be specific to the origin, expression, character and structure of the cell. Determining the unique cell surface complement of molecules of a specific cell type can be determined using techniques well known in the art.

One skilled in the art will appreciate that the tropism of the fusion protein can be altered by changing the targeting signal. In one specific embodiment, fusion proteins are provided that enable the addition of cell surface antigen specific antibodies to the fusion protein for targeting fusion protein.

It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest i. Brain Targeting

In one embodiment, the targeting signal is directed to cells of the nervous system, including the brain and peripheral nervous system. Cells in the brain include several types and states and possess unique cell surface molecules specific for the type. Furthermore, cell types and states can be further characterized and grouped by the presentation of common cell surface molecules.

In one embodiment, the targeting signal is directed to specific neurotransmitter receptors expressed on the surface of cells of the nervous system. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter or ligand capable of specifically binding to a neurotransmitter receptor.

In one embodiment, the targeting signal is specific to cells of the nervous system which may include astrocytes, microglia, neurons, oligodendrites and Schwann cells. These cells can be further divided by their function, location, shape, neurotransmitter class and pathological state. Cells of the nervous system can also be identified by their state of differentiation, for example, stem cells. Exemplary markers specific for these cell types and states are well known in the art and include, but are not limited to, CD133 and Neurosphere.

ii. Tumor Targeting

In some embodiments, the targeting signal is used to selectively target tumor cells. Tumor cells express cell surface markers which may only be expressed in the tumor or present in non-tumor cells but preferentially presented in tumor cells. Exemplary tumor specific cell surface markers include, but are not limited to, alfa-fetoprotein (AFP), C-reactive protein (CRP), cancer antigen-50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM. In one embodiment, the targeting signal consists of antibodies which are specific to the tumor cell surface markers.

iii. Antibodies

Another embodiment provides an antibody or antigen binding fragment thereof bound to the disclosed recombinant polypeptides acting as the targeting signal. The antibodies or antigen binding fragment thereof are useful for directing the fusion protein to a cell type or cell state. In one embodiment, the fusion protein possesses an antibody binding domain, for example from proteins known to bind antibodies such as Protein A and Protein G from *Staphylococcus aureus*. Other domains known to bind antibodies are known in the art and can be substituted. In certain embodiments, the antibody is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art.

In some embodiments, the targeting domain includes all or part of an antibody that directs the fusion protein to the desired target cell type or cell state. Antibodies can be monoclonal or polyclonal, but are preferably monoclonal. For human gene therapy purposes, antibodies are derived from human genes and are specific for cell surface markers, and are produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

iv. Organelle Targeting

Additional embodiments are directed to specifically delivering the fusion protein to intracellular compartments or organelles. Eukaryotic cells contain membrane bound structures or organelles. Organelles can have single or multiple membranes and exist in both plant and animal cells. Depending on the function of the organelle, the organelle can consist of specific components such as proteins and cofactors. The polypeptides delivered to the organelle can enhance or contribute to the functioning of the organelle. Some organelles, such as mitochondria and chloroplasts, contain their own genome. Nucleic acids are replicated, transcribed, and translated within these organelles. Proteins are imported and metabolites are exported. Thus, there is an exchange of material across the membranes of organelles. Exemplary organelles include the nucleus, mitochondrion, chloroplast, lysosome, peroxisome, Golgi, endoplasmic reticulum, and nucleolus. Synthetic organelles can be formed from lipids and can contain specific proteins within the lipid membranes. In some embodiments, the fusion proteins are targeted to the nucleus of cells.

3. Isolated Nucleic Acid Molecules

Isolated nucleic acid sequences encoding Brd4 polypeptides, fusions fragments and variants thereof are also disclosed herein. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-Brd4 proteins). The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

The nucleic acid sequences encoding Brd4 polypeptides include genomic sequences. Also disclosed are mRNA sequence wherein the exons have been deleted. Other nucleic acid sequences encoding Brd4 polypeptides, such polypeptides that include the above-identified amino acid sequences and fragments and variants thereof, are also disclosed. Nucleic acids encoding Brd4 fusion polypeptides may be optimized for expression in the expression host of choice. Codons may be substituted with alternative codons encoding the same amino acid to account for differences in codon usage between the organism from which the Brd4 nucleic acid sequence is derived and the expression host. In this manner, the nucleic acids may be synthesized using expression host-preferred codons.

Nucleic acids can be in sense or antisense orientation, or can be complementary to a reference sequence encoding a Brd4 polypeptide. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2'hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.*, 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Nucleic acids encoding polypeptides can be administered to subjects in need thereof. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008).

4. Vectors and Host Cells

Vectors encoding Brd4 polypeptides, fusion, fragments, and variants thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. For example, the control sequence can be incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A. In one embodiment, a nucleic acid molecule encoding a Brd4 fusion polypeptide is present in a vector containing nucleic acids that encode one or more domains of an Ig heavy chain constant region, preferably having an amino acid sequence corresponding to the hinge, $C_H2$ and $C_H3$ regions of a human immunoglobulin Cγ1 chain.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the Brd4 polypeptides or fusion polypeptides described herein.

The vectors can be used to express Brd4 in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. For example, nucleic acids encoding polypeptides can be administered directly to lymphoid tissues or tumors. Alternatively, lymphoid tissue specific targeting can be achieved using lymphoid tissue-specific transcriptional regulatory elements (TREs) such as a 13 lymphocyte-, T lymphocyte-, or dendritic cell-specific TRE. Lymphoid tissue specific TREs are known in the art.

Nucleic acids may also be administered in vivo by viral means. Nucleic acid molecules encoding polypeptides or fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in viva, physical means well-known in the art can be used for direct transfer of DNA, including administration of plasmid DNA and particle-bombardment mediated gene transfer.

5. Other Compounds that Increase the Bioactivity of Brd4

In some embodiments, the compositions include a compound that increases bioactivity of endogenous Brd4, preferably Brd4 isoform B. Such compounds include factors that increase the expression of or increase the half life of endogenous Brd4, preferably Brd4 isoform B. Factors that increase expression of endogenous Brd4 include, for example, Brd4 transcription factors. Brd4 transcription factors can be provided as a recombinant polypeptide, or an isolated nucleic acid encoding the transcription factor.

In some embodiments the factor that increases expression of endogenous Brd4 or increase the half life of engodenous Brd4 is a small molecule.

C. Compounds that Decrease the Bioactivity of Brd4

Compounds that reduce the bioactivity of one or more isoforms of Brd4, particularly isoform B, can be used to protect cells from DNA damage. For example, compounds which inhibit Brd4 bromodomain binding of one or more Brd4 isoforms, particularly isoform B to acetylated histones, or mis-localize one or more Brd4 isoforms, particularly isoform B, away from chromatin can be used to protect cells from DNA damaging agents including, but not limited to, ionizing radiation.

1. Inhibitory Nucleic Acids for Antagonizing Brd4

Inhibitory nucleic acids can be used to antagonize one or more isoforms of Brd4, particularly Brd4 isoform B, by inhibiting or down regulating expression of one or more isoforms of Brd4, particularly Brd4 isoform B from mRNA encoding one or more isoforms of Brd4. Thus, in some embodiments, the Brd4 antagonist is an inhibitory nucleic acid that silences gene expression. In some embodiments, the Brd4 antagonist is an inhibitory nucleic acid that silences expression of Brd4 isoform A, Brd4 isoform B, Brd4 isoform C, or combinations thereof. Any inhibitory nucleic acids based on the above-identified nucleic acid sequences or a nucleic acid sequence encoding a polypeptide including the above-identified amino acid sequences or a fragment or variant thereof. In some embodiments the inhibitory nucleic acid targets Brd4 isoform A, isoform B, isoform C, or combinations thereof. In some embodiments, the inhibitory nucleic acid targets a sequence that is conserved in all three isoforms, and therefore reduces bioavailability of all three isoforms. For example, in some embodiments, the inhibitory nucleic acid targets a nucleic acid encoding amino acids 1 to 719 of isoform A, for a fragment or variant thereof.

In some embodiments the inhibitory nucleic acid specifically reduces bioavailability of a particular isoform of Brd4 by targeting an mRNA sequence that is unique to the target Brd4 isoform. For example, in some embodiments, the inhibitory nucleic acid is a nucleic acid that reduces bioavailability of Brd4 isoform B, but not isoform A, or isoform C, or a combination thereof. An inhibitory nucleic acid specific for Brd4 isoform B can target a nucleic acid sequence that encodes an amino acid sequence of isoform B that is not present in isoform A or isoform C. For example, the inhibitory nucleic acid can target the above-identified nucleic acid encoding isoform B, or a fragment or variant thereof.

In some embodiments, the inhibitory nucleic acid is a nucleic acid that reduces bioavailability of Brd4 isoform A, but not isoform B, or isoform C, or a combination thereof. An inhibitory nucleic acid specific for Brd4 isoform A can target a nucleic acid sequence that encodes an amino acid sequence of isoform A that is not present in isoform B or isoform C. For example, the inhibitory nucleic acid can target a nucleic acid encoding amino acids 720 to 1363 of isoform A, or a fragment or variant thereof.

In some embodiments, the inhibitory nucleic acid is a nucleic acid that reduces bioavailability of Brd4 isoform C, but not isoform A, or isoform B, or a combination thereof. An inhibitory nucleic acid specific for Brd4 isoform C can target a nucleic acid sequence that encodes an amino acid sequence of isoform A that is not present in isoform A or isoform B.

Inhibitory nucleic acid technologies are known in the art and include, but are not limited to, antisense oligonucleotides, catalytic nucleic acids such as ribozymes and deoxyribozymes, aptamers, triplex forming nucleic acids, external guide sequences, and RNA interference molecules (RNAi), particularly small nucleic acid molecules, such as short interfering nucleic acid (siNA), short interfering RNA (siRNA), double-stranded RNA (dsRNA), micro-RNA (mRNA), and short hairpin RNA (shRNA) molecules capable of mediating RNA interference (RNAi).

a. RNA Interference

Gene silencing by RNAi was originally observed with the addition of double stranded RNA (dsRNA) (Fire, A., et al. (1998) Nature, 391:806-11; Napoli, C., et al. (1990) Plant Cell 2:279-89; Hannon, G. J. (2002) Nature, 418:244-51).

Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

In some embodiments the inhibitory nucleic acid is an siRNA. SiRNA is typically a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. Sequence specific gene or isoform specific silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

Small RNAs include microRNAs (miRNA) and small interfering RNAs (siRNAs). MiRNAs are produced by the cleavage of short stem-loop precursors by Dicer-like enzymes; whereas, siRNAs are produced by the cleavage of long double-stranded RNA molecules. MiRNAs are single-stranded, whereas siRNAs are double-stranded. Therefore, the double-stranded structure may be formed by a single self-complementary RNA strand or two separate complementary RNA strands. RNA duplex formation may be initiated either inside or outside the plant cell.

Suitable inhibitory nucleic acids can contain one or more modified bases, or have a modified backbone to increase stability or for other reasons. For example, the phosphodiester linkages of natural RNA may be modified to include at least one of a nitrogen or sulfur heteroatom. Moreover, nucleic acids comprising unusual bases, such as inosine, or modified bases, such as tritylated bases, to name just two examples, can be used. It will be appreciated that a great variety of modifications have been made to nucleic acids that serve many useful purposes. The term nucleic acids as it is employed herein embraces such chemically, enzymatically or metabolically modified forms of nucleic acids, provided that it is derived from an endogenous template.

The sequence of at least one strand of the RNAi molecule contains a region complementary to at least a part of the target mRNA sufficient for the RNAi molecule to specifically hybridize to the target mRNA. In one embodiment, one strand of the RNAi molecule is substantially identical to at least a portion of the target mRNA.

In one embodiment, the inhibitory nucleic acid has 100% sequence identity with at least a part of the target mRNA. However, inhibitory nucleic acids having 70%, 80% or greater than 90% or 95% sequence identity may be used. Thus sequence variations that might be expected due to genetic mutation, strain polymorphism, or evolutionary divergence can be tolerated.

RNAi molecules includes small RNA molecules which are single stranded or double stranded RNA molecules generally less than 200 nucleotides in length. Such molecules are generally less than 100 nucleotides and usually vary from 10 to 100 nucleotides in length. The duplex region of a double stranded RNA may have a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). While the optimum length of the double stranded RNA may vary according to the target sequence and experimental conditions, the duplex region of the RNA may be at least 19, 20, 21, 22, 23, 25, 50, 100, 200, 300, 400 or more nucleotides long. In a preferred format, small RNA molecules, such as siRNA and shRNA have 11, 12, 13, 14, 15, 16, 17, 18, 19, 20, 21, 22, 23, 24, 25, 26, 27, 28, 29 or 30 nucleotides. Preferably, the nucleotides are contiguous, consecutive nucleotides of complementary to a target mRNA sequence, for example Brd4 mRNA.

In vivo, the RNAi molecule may be synthesized using recombinant techniques well known in the art (see e.g., Sambrook, et al., Molecular Cloning; A Laboratory Manual, Third Edition (2001)). For example, bacterial cells can be transformed with an expression vector which comprises the DNA template from which double stranded RNA is to be derived. Alternatively, the cells in which inhibition of gene or isoform expression is desired may be transformed with an expression vector or by other means. Bidirectional transcription of one or more copies of the template may be by endogenous RNA polymerase of the transformed cell or by a cloned RNA polymerase (e.g., T3, T7, SP6) coded for by the expression vector or a different expression vector. Inhibition of gene or isoform expression may be targeted by specific transcription in an organ, tissue, or cell type; an environmental condition (e.g. temperature, chemical); and/or engineering transcription at a developmental stage or age, especially when the RNAi molecule is synthesized in vivo. RNAi molecules may also be delivered to specific tissues or cell types using known gene delivery systems. The production of siRNA from a vector is commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. are any shRNA designed as described above based on the sequences for the herein disclosed inflammatory mediators.

b. Aptamers

In some embodiments, a compound that reduces the bioavailability of one or more isoforms of Brd4 is an aptamer. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules as well as large molecules, such as reverse transcriptase. Aptamers can bind very tightly with $K_d$'s from the target molecule of less than 10-12 M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide. Representative examples of how to make and use aptamers to bind a variety of different target molecules are known in the art.

c. Ribozymes

In some embodiments, a compound that reduces the bioavailability of one or more isoforms of Brd4 is a ribozyme. Ribozymes are nucleic acid molecules that are capable of catalyzing a chemical reaction, either intramolecularly or intermolecularly. Ribozymes are thus catalytic nucleic acids. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Examples of how to make and use ribozymes to catalyze a variety of different reactions are known in the art.

d. Triplex Forming Nucleic Acids

In some embodiments a compound that reduces the bioavailability of one or more isoforms of Brd4 are triplex forming nucleic acids. Triplex forming nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$. Examples of how to make and use triplex forming molecules to bind a variety of different target molecules are known in the art.

e. External Guide Sequences

In some embodiments a compound that reduces the bioavailability of one or more isoforms of Brd4 are external guide sequences (EGSs). EGSs are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells. Examples of how to make and use EGS molecules to facilitate cleavage of a variety of different target molecules are known in the art.

2. Antibodies

Monoclonal and polyclonal antibodies that are reactive with epitopes of Brd4 isoform A, isoform B, isoform C, or combinations thereof, that can inhibit the interaction of Brd4 isoform A, isoform B, isoform C, or combinations thereof with acetylated histones are also useful to antagonize Brd4 polypeptide activity. Thus, in some embodiments, a compound that reduces the bioavailability of a Brd4 polypeptide is an antibody that specifically binds a Brd4 polypeptide and prevents Brd4 binding to acetylated histones under physiological conditions.

Monoclonal antibodies (mAbs) and methods for their production and use are described in Hartlow, E. et al., Antibodies: A Laboratory Manual, Cold Spring Harbor Laboratory Press, Cold Spring Harbor, N.Y., 1988). Anti-idiotypic antibodies are described, for example, in *Idiotypes in Biology and Medicine*, S Karger Pub. 1990.

The antibodies can be xenogeneic, allogeneic, syngeneic, or modified forms thereof, such as humanized or chimeric antibodies. Antiidiotypic antibodies specific for the idiotype of a specific antibody, for example, an anti-Erbin antibody, are also included. The term "antibody" is meant to include both intact molecules as well as fragments thereof that include the antigen-binding site and are capable of binding to a Brd4 epitope. These include, Fab and F(ab')$_2$ fragments which lack the Fc fragment of an intact antibody, clear more rapidly from the circulation, and may have less non-specific tissue binding than an intact antibody (Wahl et al., *J. Nuc. Med.* 24:316-325 (1983)). Also included are Fv fragments (Hochman, J. et al. (1973) *Biochemistry*, 12:1130-1135; Sharon, J. et al. (1976) *Biochemistry*, 15:1591-1594). These various fragments are produced using conventional techniques such as protease cleavage or chemical cleavage (see, e.g., Rousseaux et al., *Meth. Enzymol.*, 121:663-69 (1986)).

Polyclonal antibodies are obtained as sera from immunized animals such as rabbits, goats, rodents, etc. and may be used directly without further treatment or may be subjected to conventional enrichment or purification methods such as ammonium sulfate precipitation, ion exchange chromatography, and affinity chromatography.

The immunogen may include the complete Brd4 polypeptide, such as Brd4 isoform A, isoform B, or isoform C, or fragments or derivatives thereof. In some embodiments, that antibody binds an epitope that is conserved in all three isoforms. Immunogens include, for example, all or a part of one or more bromodomains of Brd4, or a polypeptide including amino acids 1 to 719 of SEQ ID NO:2, or fragments or variants thereof. In some embodiments the antibody is specific for Brd4 isoform B. In some embodiments the antibody or antigen binding fragment is designed to bind an epitope on Brd4 isoform B that is masked or absent on isoform A, isoform C, or combinations thereof. In some embodiments the antibody or antigen binding fragment is designed to bind an epitope on Brd4 isoform A that is masked or absent on isoform B, isoform C, or combinations thereof. For example, in some embodiments, the antibody or antigen binding fragment binds to a polypeptide including amino acids 719 to 1362 of SEQ ID NO:2 or an antigenic fragment or variant thereof. In some embodiments the antibody or antigen binding fragment is designed to bind an epitope on Brd4 isoform C that is masked or absent on isoform A, isoform B, or combinations thereof. Immunogens including bromodomain I (SEQ ID NO:7), bromodomain II, and amino acids 719 to 1362 of SEQ ID NO:2, or antigenic fragments or variants thereof can be produced in a variety of ways known in the art, e.g., expression of cloned nucleic acid sequence using conventional recombinant methods or isolation from cells of origin.

Monoclonal antibodies can be produced using conventional hybridoma technology, such as the procedures introduced by Kohler and Milstein, Nature, 256:495-97 (1975), and modifications thereof (see above references). An animal, preferably a mouse is primed by immunization with an immunogen as above to elicit the desired antibody response in the primed animal. B lymphocytes from the lymph nodes, spleens or peripheral blood of a primed, animal are fused with myeloma cells, generally in the presence of a fusion promoting agent such as polyethylene glycol (PEG). Any of a number of murine myeloma cell lines are available for such use: the P3-NS1/1-Ag4-1, P3-x63-k0Ag8.653, Sp2/0-Ag14, or HL1-653 myeloma lines (available from the ATCC, Rockville, Md.). Subsequent steps include growth in selective medium so that unfused parental myeloma cells and donor lymphocyte cells eventually die while only the hybridoma cells survive. These are cloned and grown and their supernatants screened for the presence of antibody of the desired specificity, e.g. by immunoassay techniques. Positive clones are subcloned, e.g., by limiting dilution, and the monoclonal antibodies are isolated.

Hybridomas produced according to these methods can be propagated in vitro or in vivo (in ascites fluid) using techniques known in the art (see generally Fink et al., Prog. Clin. Pathol., 9:121-33 (1984)). Generally, the individual cell line is propagated in culture and the culture medium containing high concentrations of a single monoclonal antibody can be harvested by decantation, filtration, or centrifugation.

The antibody may be produced as a single chain antibody or scFv instead of the normal multimeric structure. Single chain antibodies include the hypervariable regions from an Ig of interest and recreate the antigen binding site of the native Ig while being a fraction of the size of the intact Ig (Skerra, A. et al. Science, 240: 1038-1041 (1988); Pluckthun, A. et al., Methods Enzymol., 178: 497-515 (1989); Winter, G. et al., Nature, 349: 293-299 (1991)). In a preferred embodiment, the antibody is produced using conventional molecular biology techniques.

3. Small Molecule Inhibitors of Brd4

The term "small molecule" generally refers to small organic compounds having a molecular weight of more than about 100 and less than about 2,500 Daltons, preferably between 100 and 2000, more preferably between about 100 and about 1250, more preferably between about 100 and about 1000, more preferably between about 100 and about 750, more preferably between about 200 and about 500 Daltons. The small molecules can include cyclical carbon or heterocyclic structures and/or aromatic or polyaromatic structures substituted with one or more functional groups. The small molecule antagonist reduces or interferes with Brd4 binding to acetylated histones by binding to Brd4 isoform A, Brd4 isoform B, or Brd4 isoform C, or combinations thereof. For example, in some embodiments, the small molecule competitively blocks, inhibits or reduces the ability of the acetyl-lysine recognition motifs of one or more of the bromodomains to bind to acetyl-lysine. In one embodiment, the small molecule is Brd4 bromodomain inhibitor (+)JQ1 (P. Filippakopoulos, et al., Nature, 468: 1067-73 (2010)). A control for (+)JQ1 is its inactive enantiomer, (−)JQ1. The structure of JQ1 is show below:

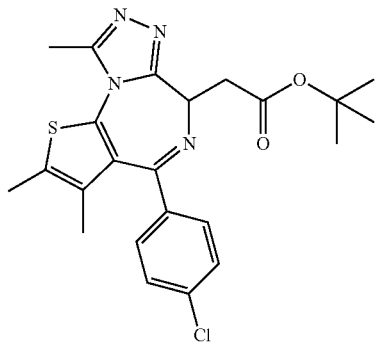 [SMILES: Cc1sc2c(c1C)C(c1ccc(Cl)cc1)=NC(CC(=O)OC(C)(C)C)c1nnc(C)n1-2]

Derivatives of JQ1 may also be used. Derivatives include compounds where the core ring structure is retained but the molecule differs in one or more substituents on the core ring structure.

In some embodiments, the small molecule inhibitor is specific for isoform B. Therefore, in some embodiments, the small molecule antagonist reduces or interferes with the bioavailability of isoform B by binding to Brd4 isoform B but does not reduce or interfere with the bioavailability of isoforms A, isoform C, or a combination thereof. The small molecule can specifically target a domain masked or absent on isoform A and C. In some embodiments, the small molecule antagonist reduces or interferes with the bioavailability of isoform A by binding to Brd4 isoform A but does not reduce or interfere with the bioavailability of isoforms B, isoform C, or a combination thereof. The small molecule can specifically target a domain masked or absent on isoform B and C, for example, a domain including amino acids 1 to 719 of SEQ ID NO:2 or a fragment or variant thereof. In some embodiments, the small molecule antagonist reduces or interferes with the bioavailability of isoform C by binding to Brd4 isoform C but does not reduce or interfere with the bioavailability of isoforms A, isoform B, or a combination thereof.

D. Pharmaceutical Compositions

Pharmaceutical compositions including the polypeptides, fusion proteins, nucleic acids, and small molecules are provided. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the polypeptides, fusion proteins, nucleic acids, small molecules, or combinations thereof, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration.

1. Formulations for Parenteral Administration

In a preferred embodiment, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a polypeptide, fusion protein, nucleic acid, small molecule, or combinations thereof and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Topical Administration

The polypeptides, fusion proteins, nucleic acids, small molecules, or combinations thereof can be applied topically. Topical administration can include application to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations can include penetration enhancers.

3. Implants, Coatings, and Sustained or Controlled Delivery Polymeric Matrices

The polypeptides, fusion proteins, nucleic acids, small molecules, and combinations thereof can be administered in sustained or other controlled release formulations. Controlled release polymeric devices can be made for long term release systemically following implantation of a polymeric device (rod, cylinder, film, disk) or injection (microparticles). The matrix can be in the form of microparticles such as microspheres, where the polypeptide, fusion protein, nucleic acid, small molecule, or combinations thereof are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer can be cast as a thin slab or film, ranging from nanometers to four centimeters, a powder produced by grinding or other standard techniques, or even a gel such as a hydrogel.

In preferred embodiments, the Brd4 inhibitor is applied in a coating or as part of a device which is implanted at a site in which an increase in DNA damage and decrease in DNA repair is desired. Examples of such devices include brachytherapy beads for use in treating prostate or breast cancer, for example, where the Brd4 inhibitor is administered in a coating on the beads; microparticles or discs such as the GLIADEL® wafer which are also used for delivery of chemotherapeutics, especially alkylating agents such as BCNU and doxyrubicin; and in and/or on stents and vascular grafts where the Brd4 inhibitor is used to decrease overproliferation of normal fibroblasts or endothelial cells that could cause scarring or restenosis. In the preferred embodiment, the Brd4 inhibitor is in a polymeric matrix such as those described above, especially a polylactide-co-glycolide or a polyanhydride such as a sebacic acid-co-fumaric acid copolymer, for sustained release.

In other embodiments, compounds which increase levels of Brd4 are used to decrease DNA damage and increase DNA repair. These can be administered by injection in a depo or matrix, such as polymeric microparticles, providing sustained release into healthy tissue adjacent to areas being treated for cancer, to decrease radiation damage. These can also be applied to damaged, diseased, or burned tissue, to enhance healing. In preferred embodiments, these are applied to, incorporated into, or coated onto wound or burn healing dressings or into sutures. In a particularly preferred embodiment, these are delivered with dressings or treatments for non-healing chronic wounds such as decubitus or diabetic ulcers.

Either non-biodegradable or biodegradable matrices can be used for delivery of polypeptides, fusion proteins, nucleic acids, small molecules, or combinations thereof, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 8: 275-283 (1987); and Mathiowitz, et al., *J. Appl. Polymer Sci.*, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

In another embodiment, the polypeptides, fusion proteins, nucleic acids, small molecules, or combinations thereof are administered with transplanted cells encapsulated within a matrix to allow release of the Brd4 polypeptides or fragments, or fusions thereof over a period of time in the area of transplantation. The matrix can be a polymeric matrix made using any polymer suitable for cell encapsulation. Exemplary polymeric materials suitable for encapsulating cells include, but are not limited to, alginate, agarose, hyaluronic acid, collagen, synthetic monomers, albumin, fibrinogen, fibronectin, vitronectin, laminin, dextran, dextran sulfate, chondroitin sulfate, dermatan sulfate, keratan sulfate, chitin, chitosan, heparan, heparan sulfate, or a combination thereof.

In still another embodiment, the compounds are incorporated into a topical formulation such as a gel, lotion or cream, to prevent sun, radiation or aging damage to skin which arises from the increased amount of DNA damage.

VI. METHODS OF MANUFACTURE

A. Methods for Producing Polypeptides

Isolated polypeptides can be obtained by, for example, chemical synthesis or by recombinant production in a host cell. To recombinantly produce a polypeptide, including a fusion protein, a nucleic acid containing a nucleotide sequence encoding the polypeptide can be used to transform, transduce, or transfect a bacterial or eukaryotic host cell (e.g., an insect, yeast, or mammalian cell). In general, nucleic acid constructs include a regulatory sequence operably linked to a nucleotide sequence encoding the fusion protein. Regulatory sequences (also referred to herein as expression control sequences) typically do not encode a gene product, but instead affect the expression of the nucleic acid sequences to which they are operably linked.

Useful prokaryotic and eukaryotic systems for expressing and producing polypeptides are well known in the art include, for example, *Escherichia coli* strains such as BL-21, and cultured mammalian cells such as CHO cells.

In eukaryotic host cells, a number of viral-based expression systems can be utilized to express polypeptides. Viral based expression systems are well known in the art and include, but are not limited to, baculoviral, SV40, retroviral, or vaccinia based viral vectors.

Mammalian cell lines that stably express variant polypeptides can be produced using expression vectors with appropriate control elements and a selectable marker. For example, the eukaryotic expression vectors can be used to express polypeptides in Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin or by metabolic selection using the Glutamine Synthetase-NS0 system). The transfected cells can be cultured such that the polypeptide of interest is expressed, and the polypeptide can be recovered from, for example, the cell culture supernatant or from lysed cells. Alternatively, a fusion protein can be produced by (a) ligating amplified sequences into a mammalian expression vector such as pcDNA3 (Invitrogen Life Technologies), and (b) transcribing and translating in vitro using wheat germ extract or rabbit reticulocyte lysate.

Polypeptides can be isolated using, for example, chromatographic methods such as affinity chromatography, ion exchange chromatography, hydrophobic interaction chromatography, DEAE ion exchange, gel filtration, and hydroxylapatite chromatography. In some embodiments, polypeptides can be engineered to contain an additional domain containing amino acid sequence that allows the polypeptides to be captured onto an affinity matrix. For example, an Fc-fusion polypeptide in a cell culture supernatant or a cytoplasmic extract can be isolated using a protein A column. In addition, a tag such as c-myc, hemagglutinin, polyhistidine, or Flag™ (Kodak) can be used to aid polypeptide purification. Polypeptide enhancing amino acid sequence such as SUMO/SMT3 can also be added to increase expression of the polypeptide of interest. Such tags can be inserted anywhere within the polypeptide, including at either the carboxyl or amino terminus. In some embodiments, the tag is following expression of the polypeptide. Other fusions that can be useful include enzymes that aid in the detection of the polypeptide, such as alkaline phosphatase. Immunoaffinity chromatography also can be used to purify polypeptides. Polypeptides can additionally be engineered to contain a secretory signal (if there is not a secretory signal already present) that causes the polypeptide to be secreted by the cells in which it is produced. The secreted polypeptide can then be isolated from the cell media.

B. Methods for Producing Isolated Nucleic Acid Molecules

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a polypeptide or inhibitory nucleic acid. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in PCR Primer: A Laboratory Manual, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Polypeptide or inhibitory nucleic acid encoding nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992. Examples of amino acid positions that can be modified include those described herein.

III. SCREENS FOR SMALL MOLECULES THAT EFFECT BIOACTIVITY OF BRD4

Modulators of the function, expression, or bioactivity of one or more Brd4 isoforms, or gene, and homologues thereof can be identified using well known techniques and reagents. In some embodiments, the modulator increases or decreases the physical interaction between one or more isoforms of Brd4 and acetylated histones. Some modulators increase or decrease the function, expression, or bioavailability of the Brd4 isoform B without altering the bioavailability of isoform A or isoform C. Some modulators increase or decrease the function, expression, or bioavailability of the Brd4 isoform A, isoform C, or combinations thereof without altering the bioavailability of isoform B.

In some embodiments, screening assays can include random screening of large libraries of test compounds. Alternatively, the assays may be used to focus on particular classes of compounds suspected of modulating the function or expression of one or more isoforms of Brd4 or homologues thereof in cells, tissues, organs, or systems.

Assays can include determinations of protein expression, protein activity, or binding activity of one or more isoforms of Brd4. Other assays can include determinations of nucleic acid transcription or translation, for example mRNA levels, miRNA levels, mRNA stability, mRNA degradation, transcription rates, and translation rates of one or more isoforms of Brd4.

In one embodiment, the identification of a Brd4 modulator is based on the function of one or more isoforms of Brd4 in the presence and absence of a test compound. The test compound or modulator can be any substance that alters or is believed to alter the function of one or more isoforms of Brd4. In some embodiments the test compound or modulator increases or decreases the ability of an isoform of Brd4 to bind to acetylated histones. In some embodiments the test compound or modulator increases or decreases Brd4-dependent DNA damage signaling or a DNA damage response. For example, in some embodiments the test compound or modulator increases or decreases γH2AX foci number, γH2AX foci size, γH2AX foci intensity, γH2AX-mediated signaling, G2/M growth arrest, cell survival, and proliferation of a cell contacted with the compound or modulator compared to a control.

One exemplary method includes contacting one or more isoforms of Brd4 with at least a first test compound, and assaying for an interaction between one or more isoforms of Brd4 and the first test compound with an assay.

Specific assay endpoints or interactions that may be measured in the disclosed embodiments include binding to acetylated histones. These assay endpoints may be assayed using standard methods such as FACS, FACE, ELISA, Northern blotting and/or Western blotting. Moreover, the assays can be conducted in cell free systems, in isolated cells, genetically engineered cells, immortalized cells, or in organisms such as *C. elegans* and transgenic animals.

Other screening methods include labeling one or more isoforms of Brd4 to identify a test compound. One or more isoforms of Brd4 can be labeled using standard labeling procedures that are well known and used in the art. Such labels include, but are not limited to, radioactive, fluorescent, biological and enzymatic tags.

Another embodiment provides a method for identifying a modulator of expression one or more isoforms of Brd4 by determining the effect a test compound has on the expression of one or more isoforms of Brd4 in cells. For example isolated cells or whole organisms expressing one or more isoforms of Brd4 can be contacted with a test compound. Expression one or more isoforms of Brd4 can be determined by detecting Brd4 protein expression or Brd4 mRNA transcription or translation. Suitable cells for this assay include, but are not limited to, immortalized cell lines, primary cell culture, or cells engineered to express Brd4. Compounds that modulate the expression of one or more isoforms of Brd4 in particular that reduce or inhibit the expression or bioavailability of one or more isoforms of Brd4, can be selected. Alternatively, compounds that increase or enhance expression or activity one or more isoforms of Brd4 can be selected.

One example of a cell free assay is a binding assay. While not directly addressing function, the ability of a modulator to bind to a target molecule, for example binding one or more isoforms of Brd4 to acetylated histones, is strong evidence of a related biological effect. The binding of a molecule to a target may, in and of itself, be inhibitory, due to steric, allosteric or charge-charge interactions or may downregulate or inactivate one or more isoforms of Brd4. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

Techniques for high throughput screening of compounds are known in the art. Large numbers of small peptide test compounds can be synthesized on a solid substrate, such as plastic pins or some other surface. Round polypeptide is detected by various methods.

IV. Methods of Use

A. Methods of Increasing the Bioactivity of Brd4

Methods of increasing the bioactivity of one or more isoforms of Brd4, particularly Brd4 isoform B in a cell are disclosed. It has been discovered that increasing the bioactivity of Brd4, particularly Brd4 isoform B, blocks signaling from DNA damage. As discussed in more detail below, increasing the bioavailability of one or more isoforms of Brd4 can be used to increase the sensitivity of cells, particularly cancer cells, to DNA damaging agents such as ionizing radiation, chemotherapy, or combinations thereof. In some embodiments the bioavailability of one, two, or three isoforms of Brd4 are increased. In some embodiments the bioavailability of one isoform is modulated relative to the other isoforms. For example, in some embodiments, the ratio of Brd4 isoform B is increased relative to the sum or Brd4 isoform A and Brd4 isoform C.

Generally, the methods of increasing the bioavailability of one or more isoform of Brd4 include contacting a cell with an effective amount of a composition to increase the bioavailability of Brd4 in the cell compared to a control. In some embodiments, bioavailability of the one or more isoforms of Brd4 in a cell is increased by contacting the cell with a composition that increases expression of a nucleic acid sequence encoding the one or more isoforms of Brd4 in the cell. In some embodiments, bioavailability of the one or more isoforms of Brd4 in a cell is increased by contacting the cell with a composition that increases expression of one or more Brd4 polypeptides, or fragments, fusions or variants thereof, in the cell. In a preferred embodiment, the bioavailability of isoform B is increased.

In some embodiments, bioavailability of one isoform is increased by reducing bioavailability of another isoform. For example, in some embodiments, the bioavailability of isoform B is increased by reducing the bioavailability of isoform A, isoform C, or a combination thereof. Such methods may include contacting the cell with a composition that increases expression of a nucleic acid sequence encoding isoform B, contacting the cell with a composition that increases expression of isoform B, or fragments, fusions or variants thereof, in the cell, contacting the cell with a composition that reduces expression of a nucleic acid sequence encoding isoform A or isoform C, contacting the cell with a composition that reduces expression of isoform A or isoform A, or fragments or variants thereof, or combinations thereof.

Generally cells are contacted with an effective amount of a composition to increase the bioavailability of one or more isoforms of Brd4 compared to a control. Increasing the bioavailability of one or more isoforms of Brd4, particularly isoform B, can block signaling from a site of DNA damage compared to a control. Reduced signaling at a site of DNA damage can be characterized as a change in one or more DNA damage responses. DNA damage responses include, but are not limited to, a reduction in γH2AX foci number, a reduction in γH2AX foci size, a reduction in γH2AX foci intensity, a reduction in γH2AX-mediated signaling, a reduction in G2/M growth arrest, decreased cell survival, and decreased proliferation. DNA damage responses can be measured qualitatively or quantitatively using methods known in the art, including the methods described in the Examples below. DNA damage responses in cells treated with a composition for increasing bioavailability of one or more isoforms of Brd4, particularly isoform B, can be compared to a control, for example cells that are not contacted with the composition.

1. Methods of Treatment

Methods of increasing the bioactivity of one or more isoforms of Brd4, particularly Brd4 isoform B, in a cell are particularly useful in the context of treating cancer. For example, increasing the bioactivity of one or more isoforms of Brd4, particular isoform B, in a cell can increase the cell's sensitivity to a DNA damaging agent, prime the cell for radiation therapy, or increase the effectiveness of radiation therapy at killing the cell. In some embodiments, the disclosed compositions and methods for increasing the bioactivity of one or more isoforms of Brd4, particularly isoform B, are used in the treatment of cancer, for example as an adjunct to radiation therapy or chemotherapy. The composition can be administered to a subject in need therefore before, during, or in combination or alternation with a therapeutic course of one or more DNA damaging agents. In preferred embodiments, the DNA damaging agent is a DNA damaging agent that can induce formation of γH2AX foci in cells.

Increasing the bioactivity of one or more isoforms of Brd4, particularly isoform B in cells, for example, cancer or tumor cells, increases cell death following treatment with a DNA damaging agent compared to a control. In some embodiments, increasing the bioactivity of one or more isoforms of Brd4, particularly isoform B, in tumor cells reduces tumor mass following treatment with a DNA damaging agent compared to a control.

In some embodiments, a composition for increasing bioactivity of Brd4 is targeted or specifically delivered to cancer cells. The composition for increasing bioavailability of Brd4 can be delivered systemically and the DNA damaging agent can be targeted or specifically delivered to cancer cells.

DNA damaging agents include, but are not limited to, ionizing radiation and chemotherapeutic agents.

a. Ionizing Radiation

The compositions and methods can be used to increase sensitivity of a cell, for example a cancer or tumor cell, to ionizing radiation. Ionizing radiation is typically defined as radiation with enough energy to liberate an electron from the orbit of an atom, causing the atom to become charged or ionized. Ionizing radiation can be administered to a subject in need thereof as part of radiation therapy for the treatment for cancer. Examples of radiation therapy include, but are not limited to, external beam radiation therapy (EBRT or XRT) or teletherapy, brachytherapy or sealed source radiation therapy, and systemic radioisotope therapy or unsealed source radiotherapy. The radiation therapy can be administered to the subject externally (i.e., outside the body), or internally for example, brachytherapy which typically utilizes sealed radioactive sources placed in the area under treatment, and or systemic administration of radioisotopes by infusion or oral ingestion. Radiation therapy can include temporary or permanent placement of radioactive sources on or within the subject. Another example of radiation therapy is particle therapy which is typically includes external beam radiation therapy where the particles are protons or heavier ions.

Radiation therapy can be administered to a subject in combination with surgery, chemotherapy, hormone therapy, immunotherapy, or combination thereof. For example, intraoperative radiation therapy or (IORT) is delivered immediately after surgical removal of a cancer. This method has been employed in breast cancer (TARGeted Introperative radiation therapy or TARGIT), brain tumors and rectal cancers.

The amount of radiation used in photon radiation therapy is measured in gray (Gy), and can be determined based on the type and stage of cancer being treated. For example, a typical curative dose for a solid epithelial tumor ranges from 60 to 80 Gy, while lymphomas are treated with 20 to 40 Gy. Preventative doses are typically around 45-60 Gy in 1.8-2 Gy fractions (for breast, head, and neck cancers.). In some embodiments, the compositions and methods of increasing the bioavailability of one or more isoforms of Brd4 reduce the dose of radiation required to induce a curative or preventative effect.

b. Chemotherapeutic Agents

The disclosed compositions and methods can be used to increase sensitivity of a cell, for example, a cancer or tumor cell, to a chemotherapeutic agent. Preferably the chemotherapeutic agent is a DNA damaging agent, such as an alkylating agent. Alkylating agents include, but are not limited to, N,N'N'-triethylenethiophosphoramide (THIO-TEPA), cyclophosphamide (CYTOXAN; NEOSAR); chlorambucil (LEUKERAN); melphalan (ALKERAN); carmustine (BICNU); busulfan (BUSULFEX); lomustine (CEENU); dacarbazine (DTIC-DOME); oxaliplatin (ELOXATIN); carmustine (GLIADEL); ifosfamide (IFEX); mechlorethamine (MUSTARGEN); busulfan (MYLERAN); carboplatin (PARAPLATIN); cisplatin (CDDP; PLATINOL); temozolomide (TEMODAR); thiotepa (THIOPLEX); bendamustine (TREANDA); or streptozocin (ZANOSAR).

2. Cancers to be Treated

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth. The treatment is also useful for reducing overproliferation of non-cancerous tissues such as endometriosis, restenosis, and scarring (fibrosis).

Malignant tumors which may be treated are classified according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers such as vascular cancer such as multiple myeloma, adenocarcinomas and sarcomas, of bone, bladder, brain, breast, cervical, colo-rectal, esophageal, kidney, liver, lung, nasopharangeal, pancreatic, prostate, skin, stomach, and uterine. In some embodiments, the disclosed compositions are used to treat multiple cancer types concurrently. The compositions can also be used to treat metastases or tumors at multiple locations.

In a preferred embodiment, the compositions and methods are used to treat gliomas (including astrocytomas) in the brain, as well as bone, breast, prostate, colon, and lung cancers. The methods and compositions can also be used to treat pancreatic and stem cells from brain cancer. In some embodiments, the composition is used to treat lung or breast cancer carcinomas, which are the source of many brain cancers.

B. Methods of Decreasing the Bioactivity of Brd4

Methods of decreasing the bioactivity of one or more isoforms of Brd4, particularly Brd4 isoform B in a cell are also disclosed. It has been discovered that compositions that inhibit Brd4 bromodomain binding or mis-localize Brd4 can protect cells from DNA damage. Decreasing the bioactivity of Brd4, particularly Brd4 isoform B, increases signaling from DNA damage. As discussed in more detail below, decreasing the bioactivity of one or more isoforms of Brd4 can be used to increase DNA damage repair, particularly healthy or normal cells. In some embodiments the bioactivity of one, two, or three isoforms of Brd4 are decreased. In some embodiments the bioavailability of one isoform is modulated relative to the other isoforms. For example in some embodiments, the ratio of Brd4 isoform B is decreased relative to the sum or Brd4 isoform A and Brd4 isoform C.

Generally, the methods of decreasing the bioactivity of one or more isoform of Brd4 include contacting a cell with an effective amount of a composition to decrease the bioavailability of Brd4 in the cell compared to a control. In some embodiments, bioactivity of the one or more isoforms of Brd4 in a cell is decreased by contacting the cell with a composition that decreases expression of a nucleic acid sequence encoding the one or more isoforms of Brd4 in the cell. In some embodiments, bioactivity of the one or more isoforms of Brd4 in a cell is decreased by contacting the cell with a composition that decreasing expression of one or more Brd4 polypeptides, or fragments, or variants thereof, in the cell. In a preferred embodiment, the bioavailability of isoform B is decreased.

In some embodiments, bioactivity of one isoform is decreased by increasing bioavailability of another isoform. For example, in some embodiments, the bioavailability of isoform B is decreased by increasing the bioavailability of isoform A, isoform C, or a combination thereof. Such methods may include contacting the cell with a composition that decreases expression of a nucleic acid sequence encoding isoform B, contacting the cell with a composition that decreases expression of isoform B, or fragments, or variants thereof, in the cell, contacting the cell with a composition that increases expression of a nucleic acid sequence encoding isoform A or isoform C, contacting the cell with a composition that increases expression of isoform A or isoform A, or fusions, fragments or variants thereof, or combinations thereof.

Generally cells are contacted with an effective amount of a composition to decrease the bioactivity of one or more isoforms of Brd4 compared to a control. Decreasing the bioavailability of one or more isoforms of Brd4, particularly isoform B, can increase signaling from a site of DNA damage compared to a control. Increased signaling at a site of DNA damage can be characterized as a change in one or more DNA damage responses. DNA damage responses include, but are not limited to, an increase in γH2AX foci number, an increase in γH2AX foci size, an increase in γH2AX foci intensity, an increase in γH2AX-mediated signaling, an increase in G2/M growth arrest, increased cell survival, and increased proliferation. DNA damage responses can be measured qualitatively or quantitatively using methods known in the art, including the methods described in the Examples below. DNA damage responses in cells treated with a composition for decrease bioavailability of one or more isoforms of Brd4, particularly isoform B, can be compared to a control, for example cells that are not contacted with the composition.

Methods of decreasing the bioactivity of one or more isoforms of Brd4, particularly Brd4 isoform B in a cell are particularly useful in the context of protecting cells from DNA damage. For example, decreasing the bioactivity of one or more isoforms of Brd4, particular isoform B, in a cell can decrease the cell's sensitivity to a DNA damaging agent. In some embodiments, the disclosed compositions and methods for decreasing the bioactivity of one or more isoforms of Brd4, particularly isoform B, are used to protect a subject from a DNA damaging agent, for example UV or ionizing radiation. The composition can be administered to a subject in need therefore before or during exposure to a DNA damaging agent. In preferred embodiments, the DNA damaging agent is a DNA damaging agent that can induce formation of γH2AX foci in cells.

Decreasing the bioactivity of one or more isoforms of Brd4, particularly isoform B in cells, for example normal or healthy cells, reduces mutations in the cell or cell death following exposure to a DNA damaging agent. In some embodiments, the compositions and methods for decreasing the bioactivity of Brd4, particularly Brd4 isoform B, are used in method of reducing the effects of DNA damage in a subject due to exposure to ionizing radiation or UV radiation. The exposure can be due to incidental, occupation, or recreational exposure to ionizing radiation or UV radiation. The exposure can be chronic or acute. In some embodiments the source of the DNA damaging agent is the sun.

V. METHODS OF DETERMINING A CELL'S SENSITIVITY TO DNA DAMAGING AGENTS

It has been discovered that Brd4 isoform B is specifically down-regulated in recurrent tumors, relative to its level in the original tumor. It has also been discovered that Brd4 isoform B expression, but not isoform A or isoform C expression, is decreased or low in cancer patients who have tumors that are resistant to treatment with DNA damaging agents, and increased or high in patients who show a good response. Assaying the level of Brd4 isoform B expression in cancers of a subject can be used to determine to disease state and predict which patients will have a good response to radiation treatment, or to other DNA damaging agents. Accordingly, Brd4 isoform B can be used as a biomarker in a screening assay to identify patients, for example cancer patients, wherein administration of a course of treatment with a DNA damaging agent is likely to result in an improvement in one or more symptoms associated with the cancer. In one embodiment, the cancer is glioblastoma.

In certain embodiments, the disease state of a cancer in a patient can be determined by quantifying the amount of Brd4 isoform B in the cancer cells, wherein a low or decreased amount of Brd4 isoform B in the subject's cancer cells compared to a control is indicative of a cancer or tumor that is recurrent or likely to reoccur. For example, in some embodiments, a low or decreased amount of Brd4 isoform B in the subject's cancer cells is indicative that treatment of the cancer or tumor with a DNA damaging agent such as ionizing radiation is not likely to be curative.

In some embodiments, the sensitivity of cells to a DNA damaging agent can be determined by quantifying the amount of Brd4 isoform B in the cells, wherein a reduced amount of Brd4 isoform B in the cells compared to a control is indicative of cells that are resistant to the DNA damaging agent, and an increased amount of Brd4 isoform B in the cells compared to a control is indicative of cells that are sensitive to the DNA damaging agent. For example, in some embodiments high or increased expression of Brd4 isoform B expression in cells of the tumor is indicative that the tumor size or burden will be reduced following treatment with a DNA damaging agent such as ionizing radiation. In some embodiments, low or decreased expression of Brd4 isoform B expression in cells of the tumor is indicative that the tumor size or burden will not be reduced, or minimally reduced following treatment with a DNA damaging agent such as ionizing radiation.

Suitable controls can be determined by one of skill in the art, and include, for example, cancer cells from a non-recurrent cancer or tumor, or normal, or healthy cells. In some embodiments, the cells of the non-recurrent cancer or tumor of the cell type or tissue as the cancer cells from the subject to be tested. In some embodiments the normal or healthy cells are the same cell type or tissue as the cancer cells from the subject to be tested. In some embodiments the control is a single or more preferably pooled or averaged values of control cell The amount of Brd4 isoform B in cells can be determined by measuring Brd4 isoform B mRNA level, protein level, or a combination thereof.

The amount of Brd4 isoform B protein in cells can be determined using conventional techniques such as enzyme-linked immunosorbent assays, mass spectrometry, spectrophotometry, or a combination thereof.

A. Methods of Detecting Brd4 isoform B Protein Levels

Certain embodiments provide methods for detecting the presence and/or measuring a level of Brd4 isoform B protein in a biological sample, using a Brd4, or preferably an isoform B protein-specific antibody. Preferably the antibody recognizes an epitope masked or absent on isoform A and isoform C. The methods generally include: a) contacting a sample with an antibody specific for Brd4 isoform B; and b) detecting binding between the antibody and molecules of the sample.

In some embodiments, the level of Brd4 isoform B protein in a cell is determined by immunofluorescence or immunohistochemistry by staining the cells the anti-Brd4 isoform B antibody and detecting the level of staining qualitatively or quantitatively.

In some embodiments, Brd4 isoform B levels are detected in protein isolated from cells. Detection of specific binding of the Brd4 isoform B protein-specific antibody, when compared to a suitable control, is an indication that Brd4 isoform B protein is present in the sample. Suitable controls include a sample known not to contain Brd4 isoform B protein, and a sample contacted with an antibody not specific for Brd4 isoform B protein, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. In general, the Brd4 isoform B protein-specific antibody will be detectably labeled, either directly or indirectly. Direct labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. The antibody may be attached (coupled) to an insoluble support, such as a polystyrene plate or a bead. Indirect labels include second antibodies specific for Brd4 isoform B protein-specific antibodies, wherein the second antibody is labeled as described above; and optionally contain members of specific binding pairs, e.g., biotin-avidin, and the like. The biological sample may be brought into contact with and immobilized on a solid support or carrier, such as nitrocellulose, that is capable of immobilizing cells, cell particles, or soluble proteins. The support may then be washed with suitable buffers, followed by contacting with a detectably-labeled Brd4 isoform B protein-specific antibody.

B. Methods of Detecting Brd4 Isoform B mRNA, Levels

Certain embodiments provide methods for detecting the presence and/or measuring a level of Brd4 isoform B mRNA in a biological sample. Preferably the assay detects a nucleic acid sequence absent on isoform A and isoform C. The methods generally include determining the level of Brd4 isoform B mRNA in a biological sample from an individual; and comparing the level of Brd4 isoform B mRNA in a biological sample from the individual with the level of Brd4 isoform B mRNA in a control. The biological sample can be cells, for example, cancer cells. In some embodiments, the level of mRNA in cells is determined quantitatively or qualitatively by detecting the Brd4 isoform B mRNA in cells, for example, by fluorescent in situ hybridization. In some embodiments, Brd4 isoform B mRNA levels are detected in mRNA isolated from cells.

1. RT-PCR

The step of determining the level of Brd4 isoform B mRNA can be performed using quantitative RT-PCR (QRT-PCR), typically including the step of hybridizing primers which hybridize to Brd4 isoform B mRNA or the complement thereof. The primers can be between about 4-40 nucleotides in length, preferably 8-35, preferably 10-30 and still more preferably, the primers are 15-25 nucleotides in length.

Methods of RT-PCR are well known in the art. Typically, total RNA, or mRNA from a sample is used as a template and a primer specific to the transcribed portion of Brd4 isoform B is used to initiate reverse transcription. Preferably the transcribed portion of isoform B is absent from the transcribed portions of isoform A and isoform C.

One embodiment of a protocol used to design and select primers encompassed by the invention describes the principle and steps involved in the design of primers for use in real-time PCR with SYBR-Green assay. Preferably, this protocol uses The National Center for Biotechnology Information (NCBI) search engine and application of PrimerQuest primer design software. The PrimerQuest is web-base software developed for Integrated DNA Technologies, Inc. (IDT). This software is based on Primer3 developed by the Whitehead Institute for Biomedical Research.

Preferred guidelines used for designing primers encompassed by the invention are that the product or amplicon length preferably be 100-150 bases, that the optimum Tm preferably be 60° C., with the preferable ranges from 58-62° C. also being acceptable, and that the most preferable GC content be 50%, with preferable ranges from 45-55% also being acceptable. It is preferable that complementary strings of the three bases at the 3'-end of each primer to itself or the other primer be avoided in order to reduce "primer-dimer" formation. Also it is preferable that complementary sequences within a primer sequence and between the primers of a pair be avoided. Preferably, runs of 3 or more G's or C's at the 3'-end are avoided, as well as single base repeats greater than 3 bases. Unbalanced distribution of G/C- and A/T rich domains preferably are avoided, and preferably the primer has a G or C is the 3'-end. It is preferable that the 3'-end of the primers not be a T since primers with a T at the 3'-end have a greater tolerance to mismatch. It is preferable to avoid mismatches, especially at the 3'-end; and it is preferable to position at least 7 unique bases at the 3'-end. Preferably, genomic amplification is avoided, and as such, it is preferable that any one primers should span an intron. Preferably, primers should be designed so that one half or at least 7 nucleotides of the primer hybridizes to the 3' end of one exon and the remaining to the 5' end of the adjacent exon.

Preferably, the primer should be unique to a Brd4 isoform B sequence and does not match to a pseudogene, or another iso form of Brd4, for example Brd4 isoform A or C. BLAST can be used to examine the specificity of the primer.

The product of the reverse transcription is subsequently used as a template for PCR. PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. Methods to optimize the stringency of primer annealing conditions are well known in the art.

QRT-PCR, which is quantitative in nature, can also be performed to provide a quantitative measure of gene expression levels. In QRT-PCR reverse transcription and PCR can be performed in two steps, or reverse transcription combined with PCR can be performed concurrently. One of these techniques, for which there are commercially available kits such as Taqman (Perkin Elmer, Foster City, Calif.), is performed with a transcript-specific antisense probe. This probe is specific for the PCR product (e.g. a nucleic acid fragment derived from a gene or mRNA) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions are performed in 96 well plates so that samples derived from many individuals are processed and measured simultaneously. The Taqman system has the additional advantage of not requiring gel electrophoresis and allows for quantification when used with a standard curve.

A second technique useful for detecting PCR products quantitatively without is to use an intercalating dye such as the commercially available QuantiTect SYBR Green PCR (Qiagen, Valencia Calif.). RT-PCR is performed using SYBR green as a fluorescent label which is incorporated into the PCR product during the PCR stage and produces a fluorescence proportional to the amount of PCR product.

Both Taqman and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol). Additionally, other systems to quantitatively measure mRNA expression products are known including Molecular Beacons® which uses a probe having a fluorescent molecule and a quencher molecule, the probe capable of forming a hairpin structure such that when in the hairpin form, the fluorescence molecule is quenched, and when hybridized the flourescense increases giving a quantitative measurement of gene expression.

Additional techniques to quantitatively measure RNA expression include, but are not limited to, polymerase chain reaction, ligase chain reaction, Qbeta replicase and the multiplex microsphere bead assay.

The level of gene expression can be measured by amplifying RNA from a sample using transcription based amplification systems (TAS), including nucleic acid sequence amplification (NASBA) and 3 SR. In NASBA, the nucleic acids may be prepared for amplification using conventional phenol/chloroform extraction, heat denaturation, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once with a polymerase such as T7 or SP6. The resulting products, whether truncated or complete, indicate target specific sequences.

Several techniques may be used to separate amplification products. For example, amplification products may be separated by agarose, agarose-acrylamide or polyacrylamide gel electrophoresis using conventional methods. Several techniques for detecting PCR products quantitatively without electrophoresis may also be used according to the invention. For example, chromatographic techniques may be employed to effect separation. There are many kinds of chromatography which may be used in the present invention: adsorption, partition, ion-exchange and molecular sieve, HPLC, and many specialized techniques for using them including column, paper, thin-layer and gas chromatography.

Another example of a separation methodology is done by covalently labeling the oligonucleotide primers used in a PCR reaction with various types of small molecule ligands. In one such separation, a different ligand is present on each oligonucleotide. A molecule, perhaps an antibody or avidin if the ligand is biotin, that specifically binds to one of the ligands is used to coat the surface of a plate such as a 96 well ELISA plate. Upon application of the PCR reactions to the surface of such a prepared plate, the PCR products are bound with specificity to the surface. After washing the plate to remove unbound reagents, a solution containing a second molecule that binds to the first ligand is added. This second molecule is linked to some kind of reporter system. The second molecule only binds to the plate if a PCR product has been produced whereby both oligonucleotide primers are incorporated into the final PCR products. The amount of the PCR product is then detected and quantified in a commercial plate reader much as ELISA reactions are detected and quantified.

Amplification products must be visualized in order to confirm amplification of the nucleic acid sequences of interest. One typical visualization method involves staining of a gel with ethidium bromide and visualization under LTV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified nucleic acid sequence of interest. The probe preferably is conjugated to a chromophore but may be radiolabeled. In another embodiment, the probe is conjugated to a binding partner, such as an antibody or biotin, where the other member of the binding pair carries a detectable moiety.

In another embodiment, detection is by Southern blotting and hybridization with a labeled probe. The techniques involved in Southern blotting are well known to those of skill in the art and may be found in many standard books on molecular protocols. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

2. Northern Blot

The step of determining the level of Brd4 isoform B mRNA can be performed using Northern blot analysis. In Northern blots, RNA samples are first separated by size via electrophoresis in an agarose gel under denaturing conditions. The RNA is then transferred to a membrane, cross-linked and hybridized with a labelled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labelled probe, e.g., a radiolabelled cDNA, either containing the full-length, single stranded DNA or a fragment of that DNA sequence may be any length up to at least 20, at least 30, at least 50, or at least 100 consecutive nucleotides in length. The probe can be labelled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as caxbodiimides, diisocyanates, glutaraldehyde and the like. Any enzymes known to one of skill in the art can be utilized.

Examples of such enzymes include, but are not limited to, peroxidase, beta-D-galactosidase, urease, glucose oxidase plus peroxidase and alkaline phosphatase.

3. Nucleic Acid Array

In another embodiment, the step of determining the level of Brd4 isoform B mRNA can be performed by hybridizing Brd4 isoform B mRNA or a complement thereof isolated from the biological sample to an array comprising a nucleic acid including a sequence that can hybridize to the Brd4 isoform B mRNA or complement thereof, and quantifying the hybridization. Methods of preparing and executing nucleic acid microarrays for detection and quantification of an mRNA isolated from a biological sample are well known in the art.

C. Kits

Kits for determining the amount of protein or RNA product of Brd4 isoform B are also provided. Such kits include materials and reagents required for measuring the expression of Brd4 isoform B protein or mRNA. In some embodiments, the reagents of the kit are used to detect a nucleic acid sequence or amino acid sequence present on Brd4 isoform B mRNA or protein respectively that is masked or absent on the mRNA or protein of Brd4 isoform. A and isoform C.

In some embodiments, the kits include one or more additional reagents employed in the various methods, such as: (1) reagents for purifying RNA from cells; (2) primers for generating test nucleic acids; (3) dNTPs and/or rNTPs (either premixed or separate), optionally with one or more uniquely labeled dNTPs and/or rNTPs (e.g., biotinylated or Cy3 or Cy5 tagged dNTPs); (4) post synthesis labeling reagents, such as chemically active derivatives of fluorescent dyes; (5) enzymes, such as reverse transcriptases, DNA polymerases, and the like; (6) various buffer mediums, e.g., hybridization and washing buffers; (7) labeled probe purification reagents and components, like spin columns, etc.; and (8) protein purification reagents; (9) signal generation and detection reagents, e.g., streptavidin-alkaline phosphatase conjugate, chemifluorescent or chemiluminescent substrate. In particular embodiments, the kits comprise prelabeled quality controlled protein and or RNA transcript (preferably, mRNA) for use as a control.

In some embodiments, the kits are RT-PCR kits. In other embodiments, the kits are nucleic acid arrays and protein arrays. Such kits can include an array having associated Brd4 isoform B protein or nucleic acid and packaging means therefore. Alternatively the Brd4 isoform B protein or nucleic acid can be prepackaged onto an array. A microarray or RT-PCR kit can be used and contain only those reagents and materials necessary for measuring the levels of RNA products of Brd4 isoform B. Alternatively, in some embodiments, the kits can comprise materials and reagents that are not limited to those required to measure the levels of RNA of Brd4 isoform B. For example, a microarray kit or RT-PCR kit may contain reagents and materials necessary for measuring the levels of other RNA products biomarkers for example, tumor markers. In some embodiments, the microarray kit or RT-PCR kit contains reagents and materials necessary for measuring the levels of other RNA products that are not biomarkers.

In some embodiments, kits for measuring a RNA product of Brd4 isoform B include materials and reagents that are necessary for measuring the expression of the RNA product. For RT-PCR kits, the kits generally include pre-selected primers specific for particular RNA products (e.g., an exon(s), an intron(s), an exon junction(s), and an exon-intron junction(s)) of Brd4 isoform B. The RT-PCR kits can also include enzymes suitable for reverse transcribing and/or amplifying nucleic acids (e.g., polymerases such as Taq), and deoxynucleotides and buffers needed for the reaction mixture for reverse transcription and amplification. The RT-PCR kits may also comprise probes specific for Brd4 isoform B. The probes may or may not be labeled with a detectable label (e.g., a fluorescent label). Each component of the RT-PCR kit is generally in its own suitable container. Thus, these kits generally include distinct containers suitable for each individual reagent, enzyme, primer and probe. Further, the RT-PCR kits can include instructions for performing the assay and methods for interpreting and analyzing the data resulting from the performance of the assay.

For nucleic acid microarray kits, the kits generally include probes attached to a support surface. The probes may be labeled with a detectable label. In some embodiments, the probes are specific for the 5' region, the 3' region, the internal coding region, an exon(s), an intron(s), an exon junction(s), or an exon-intron junction(s) of Brd4 isoform B.

The microarray kits can include instructions for performing the assay and methods for interpreting and analyzing the data resulting from the performance of the assay. The kits can also include hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

For antibody based kits, the kit can comprise, for example: (1) a first antibody (which may or may not be attached to a support) which binds to Brd4 isoform B protein and, optionally, (2) a second, different antibody which binds to either the protein, or the first antibody and is conjugated to a detectable label (e.g., a fluorescent label, radioactive isotope or enzyme). In some embodiments, the reagents of the kit are used to detect an amino acid sequence present on Brd4 isoform B protein that is masked or absent on the mRNA or protein of Brd4 isoform A and isoform C. The antibody-based kits can also include beads for conducting an immunoprecipitation. Each component of the antibody-based kits is generally in its own suitable container. Thus, these kits generally include distinct containers suitable for each antibody. Further, the antibody-based kits can include instructions for performing the assay and methods for interpreting and analyzing the data resulting from the performance of the assay.

EXAMPLES

Example 1

Expression of Brd4 Affects the DNA Damage Response

Materials and Methods

Antibodies and Stains

Mouse monoclonal antibodies against γH2AX were from Upstate/Millipore (cat. #05636), Actin (Sigma, cat. #A5441), and phospho-ATM Serine 1981 (Rockland, cat. #200-301400). Rabbit polyclonal and monoclonal antibodies against Brd4 were from Abeam (cat. #Ab46199), total H2AX (Abeam, cat. #ab11175), phospho-SO (Cell Signaling Technologies, cat. #2851), acetyl lysine (Cell Signaling Technologies, cat. #9441), cleaved caspase 3 (Cell Signaling Technologies, cat. #9664), phopho-histone H3 (Upstate/Millipore cat. #06570 and BD/Pharmingen cat. #559565), histone H3 acetyl lysine 14 (Abeam, cat. #ab52946). DNA stains were Hoechst 33342 (Invitrogen cat #H 1399) propidium iodide (Invitrogen cat. #P1304MP) and ethidium bromide (Invitrogen cat. #15585011).

Image-Based Screens

For both shRNA and small molecule screens, human U2OS osteosarcoma cells (ATCC HTB-96) were grown in DMEM+Pen/Strep+10% v/v FBS (complete media) at 37° C. in a 5% CO2 atmosphere. All screens were carried out at passage 10-15. Cells were tested for mycoplasma by PCR prior to seeding and infection. U2OS cells were seeded with a MicroFill (Biotek) in 384-well black, clear bottom plates (Greiner) at a density of 300 (shRNA) cells/well in 50 IJL of media, and allowed to attach overnight at 37° C. in a 5% $CO_2$ atmosphere.

For shRNA screens, the media was exchanged the following day to complete media with 8 µg/mL polybrene using a JANUS workstation (PerkinElmer). Virus infection was carried out on an EP3 workstation (PerkinElmer) with 1.5 µL of hightiter retrovirus. All plates had two wells infected with 1.5 µL of control virus with shRNA directed against H2AX. Plates were centrifuged in a swinging-bucket rotor at 2250 rpm for 30 minutes following infection and returned to the incubator overnight. The plates were then selected with 2.5 µg/mL puromycin for 48 hours, and allowed to proliferate in complete media for another 48 hours, with media exchanges carried out on the JANUS or RapidPlate (Qiagen) liquid handling workstations. Eight wells in each plate were not selected with puromycin.

For small molecule testing, cells were plated at 500 cells/well in 384-well plates. The day after plating, small molecules at different concentrations in 100 nL DMSO were pin transferred to cells with a CyBio robot, and cells were propagated for 16 hours. For both small molecule and shRNA screens, four plates were created in replicate for the time points outlined below. Four wells were left untreated in each plate, and received 25 mM caffeine in complete media 1 hour prior to irradiation.

All plates were treated with 10 Gy of 667 keV X-rays from a 137Cs source in a Gammacell irradiator (Atomic Energy of Canada, Ltd). A 0 hour control plate was not irradiated. The plates were returned to the incubator and fixed with 4.4% w/v paraformaldehyde in phosphate-buffered saline (PBS) at 1, 6, and 24 hours post irradiation. Plates were stored in PBS at 4° C. prior to staining. Fixed plates were washed 3 times with PBS and blocked with 24 IJL of GSDB (0.15% goat serum, 8.33% goat serum, 120 mM sodium phosphate, 225 mM NaCl) for 30 minutes. The 0, 1, and 6 hour plates were incubated with 1:300 dilutions in GSDB of primary mouse monoclonal anti-γH2AX (Ser 139), and rabbit polyclonal anti-pHH3 antibody. For the 24 hour plates, we substituted 1:300 rabbit polyclonal anti-cleaved Caspase 3 for the pHH3 antibody.

All plates were incubated overnight at 4° C., washed, and stained with a secondary antibody mix containing 10 IJg/mL Hoescht 33342, 1:300 goat anti-mouse polyclonalAlexa Fluor 488, and goat anti-rabbit polyclonal-Alexa Fluor 555 in GSDB. After a second overnight incubation at 4° C., the plates were washed 3 times in PBS and stored in 50 IJLlwell 50 UM Trilox (Sigma) in PBS at 4° C.

Imaging and Image Analysis

Plates were allowed to equilibrate to room temperature for 30 minutes and imaged on a Cellomics ArrayScan VTI automated microscope with a 20x objective. The acquisition parameters were the same for each shRNA or chemical library. Six fields per well were imaged, with three channels/field (DAPI, fluorescein and rhodamine) for a total of 18 acquired images per well. Images were segmented and analyzed with CellProfiler cell image analysis software (Carpenter et al., *Genome Biology*, 2006, 7, R100). The imaging pipeline used to segment the images is available on request. Cell morphology and intensity data were acquired on a per image and per cell basis, and exported into a mySQL database. The data were visualized with SpotFire (TIBCO) and CellProfiler Analyst (Jones, et al., *PNAS*, 106:1826 (2009), Lamprecht, et al., *Biotechniques*, 42:71 (2007)).

Immunofluorescence Microscopy

U2OS cells were plated on #1 glass coverslips (VWR) and were cultured in DMEM+Pen/Strep+10% v/v FBS (complete media) at 37° C. in a 5% CO2 atmosphere, then exposed to 10 Gy Ionizing radiation from a 137CS source in a Gammacell irradiator (Atomic Energy of Canada, Ltd). fixed in methanol, and processed for immuofluorescence using the antibodies indicated above. Images were captured on a Zeiss Axiophot II microscope with a Hamamatsu CCD camera and processed with OpenLab/Volocity software. Quantitative image analysis was accomplished using Cell-Profiler (www.CellProfiler.org) or ImageJ software (http://rsb.info.nih.gov/nihimageJ).

Expression Profiling and Analysis

Total RNA was harvested from stable U2OS cells expressing Brd4 or control shRNA using RNeasy (Qiagen), labeled and analyzed on the Affymetrix U133 Plus 2.0 array. Unsupervised clustering of expression data was performed using the R package pvclst. L1MMA (Smyth, *Stat. Appl. Genet. Mol. Biol.*, 3, Article 3, (2004) was used to identify significant changes in expression between Brd4 knockdown and control cells.

Western Blotting

Cells were treated with 10Gy ionizing radiation in a 137Cs source in a Gammacell irradiator (Atomic Energy of Canada, Ltd). trypsinized and lysed in LB (25 mM Tris-HCl pH 7.6, 150 mM NaCl, 1 mM EOTA and 1% NP-40) with protease and phosphatase inhibitors (Complete mini EOTA-free and PhosSTOP, Roche Applied Science). Lysates were separated by SOS-PAGE, transferred to nitrocellulose, blotted with the antibodies above, and imaged using a Li-cor Odyssey (www.licor.com) scanner.

RT-PCR

Total RNA was extracted from 106 U2OS cells expressing either control or Brd4-directed shRNA, or from 1 mg tumor tissue (as described below) that had been flash frozen in liquid nitrogen with a RNeasy kit (Qiagen). cDNA was generated with oligo dT primers with SuperScript reverse transcriptase (Invitrogen) according to manufacturer's instructions. These cDNAs were used as templates for linear-range PCR amplification or quantitative real-time PCR with SYBR green master mix on an Applied Biosystems 7500 with the following primers: forward-5' CTC CTC CTA AAA AGA CGA AGA-3' (SEQ ID NO:13), and reverse (pan-isoform) 5'-TTC GGA GTC TTC GCT GTC AGA GGA G-3' (SEQ ID NO:14), (isoform A) 5'GCC CCT TCT TTT TTG ACT TCG GAG C-3' (SEQ ID NO:15), (isoform B) 5'-GCC CTG GGG ACA CGA AGT CTC CAC T-3' (SEQ ID NO:16), (isoform C) 5'-CCG TTT TAT TAA GAG TCC GTG TCC A-3' (SEQ ID NO:17), (CHEK2) forward 5'-ACAGATAAATAC CGAACATACAGC-3' (SEQ ID NO:18) and reverse 5'GACGGCGTTTTCCTTTCCCTA-CAA-3' (SEQ ID NO:19), and using (GAPOH) primers forward 5'GATGCCCTGGAGGAAGTGCT-3' (SEQ ID NO:20) and reverse 5'-AGCAGGCACAA CACCACGTT-3' (SEQ ID NO:21) as control for normalization.

Small Molecule Inhibitors

Brd4 bromodomain inhibitor (+)JQ1 and its inactive enantiomer (−)JQ1 were synthesized as described (Filippakopoulos, et al., Nature, 468:1067 (2010)) and were used at 250 nM. a-amanitin (cat. #A2263) and cycloheximide (cat. #C4859) were from Sigma and were used at concentrations as indicated a-amanitin: 1-16 µM, cycloheximide 35-560 µM). UCN01 was from Sigma (cat. #U6508) and was used at concentrations of 0.003-10 µM. Caffeine was from Sigma (cat. #C0750) and was used at concentrations 10-25 mM.

Results

To explore the role of chromatin modification in the DDR, a high-throughput, high-content quantitative microscopy assay multiplexed for early and late DDR endpoints was developed (FIG. 1A). The assay was applied to an RNAi screen focused on chromatin interacting proteins and modifying enzymes together with a collection of proteins known to be important in DNA damage signaling and cancer.

U20S cells in 384 well plates were infected with lentiviral shRNAs (D. E. Root, et al., Nat Methods, 3:715 (2006)), irradiated with 10Gy of ionizing radiation (IR) and analyzed at 0 (unirradiated), 1, 6 and 24 hours later (FIG. 1A). At each time point, cells were co-stained with antibodies against γH2AX to measure early signaling events in the DDR, Hoechst 33342 to measure DNA content and monitor cell cycle progression and arrest, and phospho-histone H3 (pHH3) to measure mitotic entry (FIG. 1B). At 24 hours, cleaved caspase-3 (CC3) was substituted for pHH3 to measure apoptotic cell death. Six representative images were acquired from each well at every time point and customized image analysis software (CellProfiler) (M. R. Lamprecht, et al., Biotechniques, 42:71 (2007); A. E. Carpenter, et al., Nat Rev Genet, 5:11 (2004); J. Moffat, et al., Cell, 124:1283 (2006); A. E. Carpenter, et al., Genome Biol, 7:R100 (2006)) used to extract data from the resulting 184,000 images to quantitatively measure the cellular responses listed above. Perturbation of known components of the DDR signaling response machinery scored strongly in this screen. Examples include: caffeine (a known inhibitor of ATM and ATR) and shRNAs against ATM dramatically reduced the number and intensity of γH2AX foci while knockdown of PP2CA, a Phosphatase that acts on γH2AX (D. Chowdhury, et al., Mol Cell, 20:801 (2005)) had the opposite effect (FIG. 1C); knockdown of BRCA2, which is required for efficient repair of DNA by homologous recombination (M. E. Moynahan, et al., Molecular Cell, 7:263 (2001); A. R. Venkitaraman, Cell, 108:171 (2002)) resulted in persistently elevated γH2AX foci at late times (FIG. 1C); both caffeine and UCN01 (an inhibitor of Chk1 and MK2, (E. C. Busby, et al., Cancer Res, 60:2108 (2000)), as well as shRNAs against p53 and ATR, abrogated the normal G2/M arrest following irradiation, leading to premature mitotic entry (FIGS. 1B, 1D, 1F, and 1G); and shRNAs against XRCC5 resulted in enhanced apoptotic cell death (A. Nussenzweig, et al., Proc Natl Acad Sci USA, 94:13588 (1997)) 24 hours after irradiation (FIG. 1D).

Figure 2A:
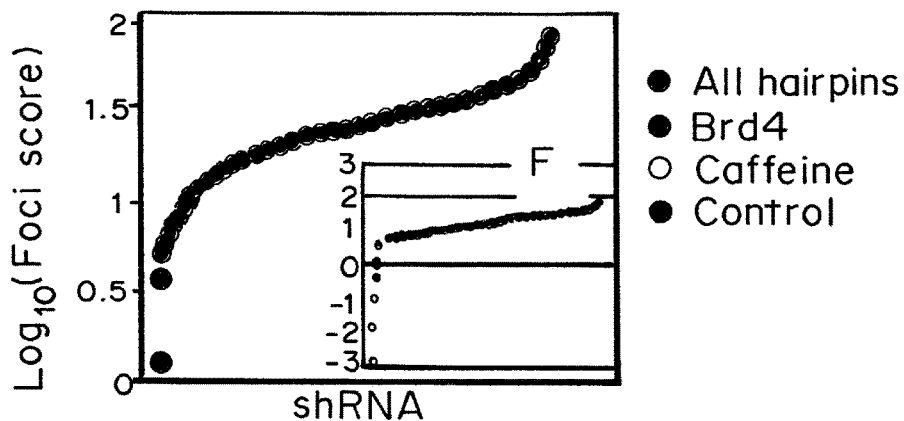
FIG. 2A is a scatter plot showing the foci score (Log 10) of shRNA (all hairpins, Brd4, caffeine, and Control treatment groups). The inset is a scatter plot of data including caffeine-treated control wells for reference.
Figure 2B:
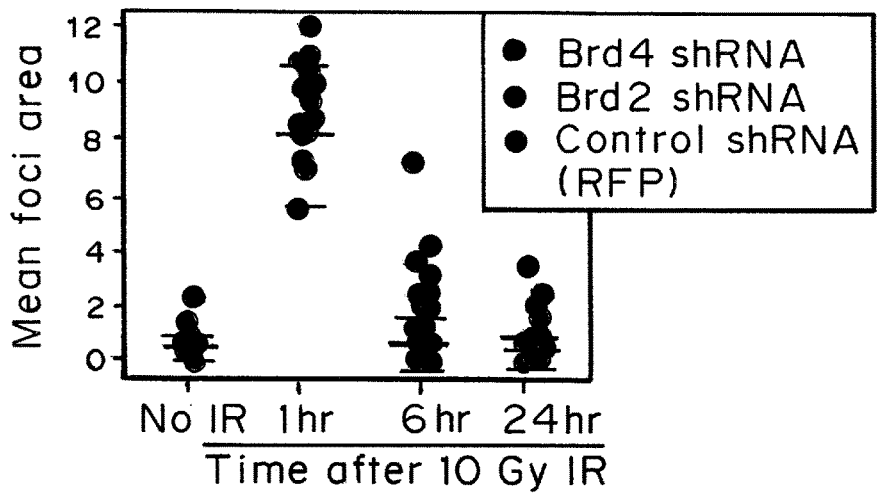
FIG. 2B is a dot plot showing the mean foci area of Brd4 shRNA, Brd2 shRNA, and Control treatment groups a function of time both before and after treatment with 10 Gy ionizing radiation. Thick bars represent mean values and thin bars represent 2 S.D. of the mean.
Figure 2C:
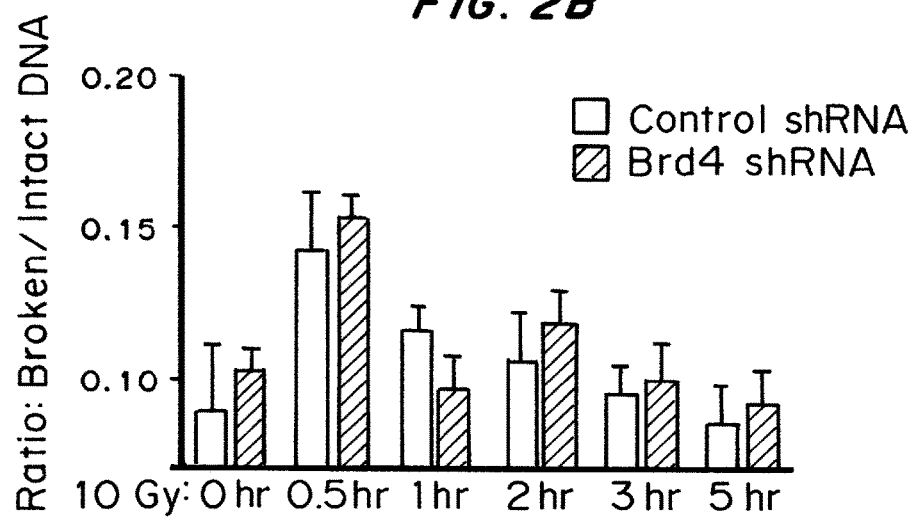
FIG. 2C is a bar graph showing the ratio of Broken DNA to Intact DNA following treatment with Brd4 shRNA or Control shRNA as a function of time in a pulsed-field electrophoresis assay.
Figure 2G:
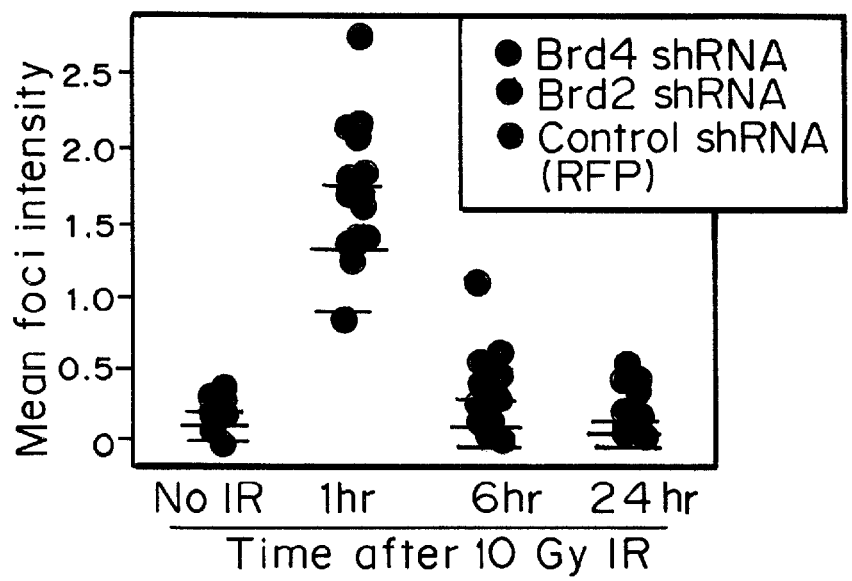
FIG. 2G is a dot plot showing the mean γH2AX foci intensity (mean integrated intensity per image) of control, Brd2 shRNA, and Brd4 shRNA without IR, and 1 hr, 6 hr, and 24 hr, after exposure to 10 Gy IR.
Figure 2H:
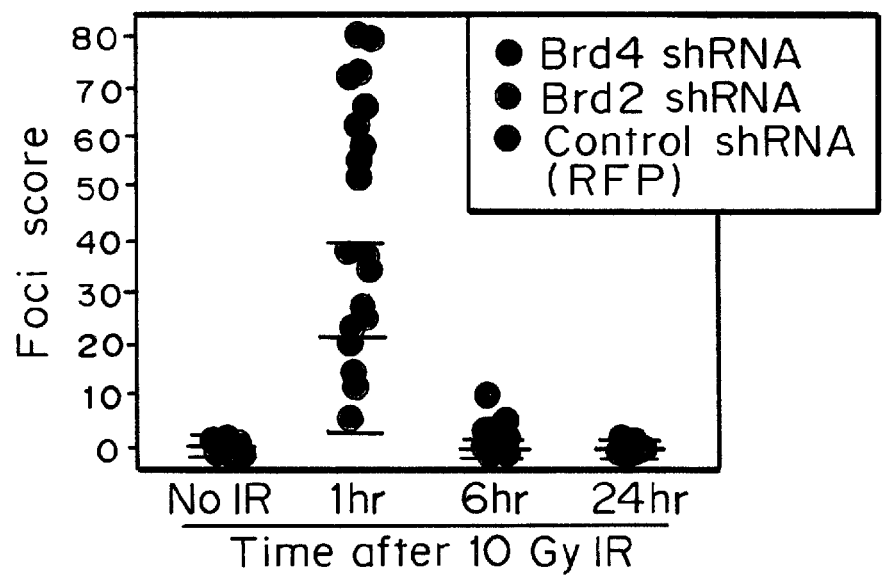
FIG. 2H is a dot plot showing the γH2AX foci score (the product of foci number per nucleus and mean integrated foci intensity) of control, Brd2 shRNA, and Brd4 shRNA without IR, and 1 hr, 6 hr, and 24 hr, after exposure to 10 Gy IR.

One thousand and two (1002) shRNAs directed against 196 genes with known and predicted chromatin modifying activity were tested for their involvement in the DNA damage response (FIG. 2A). Intriguingly, the most pronounced increase in γH2AX foci number, size and intensity following IR was observed after knockdown of Brd4, a double-bromodomain protein that binds acetyl-lysine (FIGS. 2A-B, 2F-H). Cells expressing multiple distinct shRNA hairpins directed against Brd4 showed increased γH2AX signal at 1, 6, and 24 hrs after exposure to 10Gy IR. This effect was not observed following knockdown of other bromodomain-containing proteins (FIGS. 2B, 1H, 2G-H), and was further confirmed in short-term Brd4 knockdowns using siRNA oligonucleotides targeting additional independent sequences within Brd4. The enhancement of multiple parameters of γH2AX foci following Brd4 knockdown, including their size, and intensity, in addition to their number, point to a role for Brd4 in limiting the propagation of DDR signaling following IR (FIG. 2A-B, 2G-H).

Example 2

Enhanced Signaling from Damaged DNA is Observed in the Absence of Brd4

Materials and Methods

Pulsed Field Gel Electrophoresis and Micrococcal Nuclease Assay

For pulse field gel analysis, control and BRD4 knockdown cells were plated at 1×106 cells per plate, exposed to 10Gy IR with a 137CS source in a Gammacell irradiator (Atomic Energy of Canada, Ltd). and harvested at 0.5, 1, 2, 3 and 5 hour timepoints. Cells were trypsinized, diluted to 2×106 cells and embedded in agarose plugs. The agarose plugs were exposed to Proteinase K (1 mg/mL) in 500 mM EDTA, 1% N-Iauryl Sarcosyl, pH 8.0, for 48 hrs, washed 3×1 hr with TE buffer, loaded onto a 0.675% agarose gel, and separated under pUlsed-field conditions with a Rotaphor 6.0 (Biometra, www.biometra.com). Nuclei from control and Brd4 knockdown cells were isolated by hypotonic lysis and micrococcal nuclease assays performed as described by Carey and Smale, CSH Protoc., pdb.prot4890 (2007).

Results

One explanation for the results described herein is that Brd4-dependent alterations in chromatin structure increased the levels of DNA damage either by enhancing IR-induced DNA double strand breaks (DSBs) or by limiting the rate of repair. To investigate this, a pulsed-field gel electrophoresis was used to quantify DSBs caused by 10Gy IR in U20S cells expressing control or Brd4-directed shRNA. No increase in the amount of IR-induced DSBs was observed in the Brd4 knockdown cells, and the kinetics of DNA DSB repair in the control and Brd4 knockdown cells was similar (FIG. 2D). These observations, together with our finding that individual γH2AX foci were larger and more intense in irradiated Brd4 knockdown cells (FIGS. 2B, 2G-H), suggest that there is enhanced signaling from damaged DNA in the absence of Brd4, rather than an increase in the amount of damage per se.

The susceptibility of DNA from control and Brd4-knockdown cells to micrococcal nuclease digestion was measured to determine if this result was caused by alterations in chromatin structure. DNA from Brd4 knockdown cells was more readily digested to smaller nucleosome fragments than DNA from control cells, consistent with a more open global chromatin structure that facilitates loading of DDR signaling molecules in the absence of Brd4 function. Consistent with this role for Brd4 as an endogenous chromatin compactor that suppresses DDR-associated signaling, it was observed that cells lacking Brd4 not only showed enhanced γH2AX signaling, but also had a prolonged G2/M arrest (FIG. 2D) and showed significantly increased cell survival and proliferation after IR (FIG. 2E, F).

Example 3

Brd4 Isoform B is a Suppressor of DNA Damage Signaling and Response

Materials and Methods

Flow Cytometry

3×106 U2OS cells were plated and transiently transfected with pEGFP-C 1, isoform C, isoform B, isoform B, BD1 mutant, Brd4-NUT and truncated Brd4-NUT using Fugene 6 (Roche). These cells were exposed to 10 Gy Ionizing radiation and harvested 24 hrs later, fixed with 4% formaldehyde, extracted with 100% ethanol, processed for flow cytometry using the antibodies listed above. Data were analyzed using FlowJo (www.flowjo.com) software.

Colony Formation and CellTiter-Glo Assays

Control and BRD4 knockdown cells were exposed to 10Gy IR or left untreated, trypsinized, counted and re-plated using serial dilutions. Colonies were propagated to the 10-15 cell stage (3-7 days), stained with Wright stain and counted with CellProfiler software. CellTiterGlo (Promega) assays were performed in 96-well format according to manufacturer's instructions and analyzed on a Perkin-Elmer Micro-Beta instrument.

Constructs, shRNA and siRNA

Full length constructs of Brd4-NUT (accession #AY166680.1), Brd4 isoform A (accession # NM_058243), B (accession #BC035266) and C (accession #NM_014299.2) were cloned into pEGFP-C1 (Clontech) and pFLAG-CMV2 (Sigma) by PCR. Bromodomain mutations were introduced using quickchange (Stratagene) using PCR primers: 5'AAA TIG TTA CAT CGC CAA CAA GCC TGG AGA TGA CGC AGT CTT AAT GGC AG-3' and 5'-CTG CCA TTA AGA CTG CGT CAT CTC CAG GCT TGT TGG CGA TOT AAC AAT TT-3'. shRNA directed against Brd4 were from the TRC library (see Table S1), or created in the mir30-based pMLP vector (kind gift of Dr. Michael Hemann) with primer 5'-TGC TOT TGA CAG TGA GCG AAG ACA CA-3' for Brd4. U2OS cell lines stably expressing this shRNA or control hairpins (ineffective hairpins directed against human sequences of BAD and PUMA) were created using puromycin selection at 2 ug/mL. STEALTH siRNA against BRD4 and control were purchased from Invitrogen, and used according to manufacturer's instructions.

Results

Figures 1, 1H, 2, 3, 4, 5:
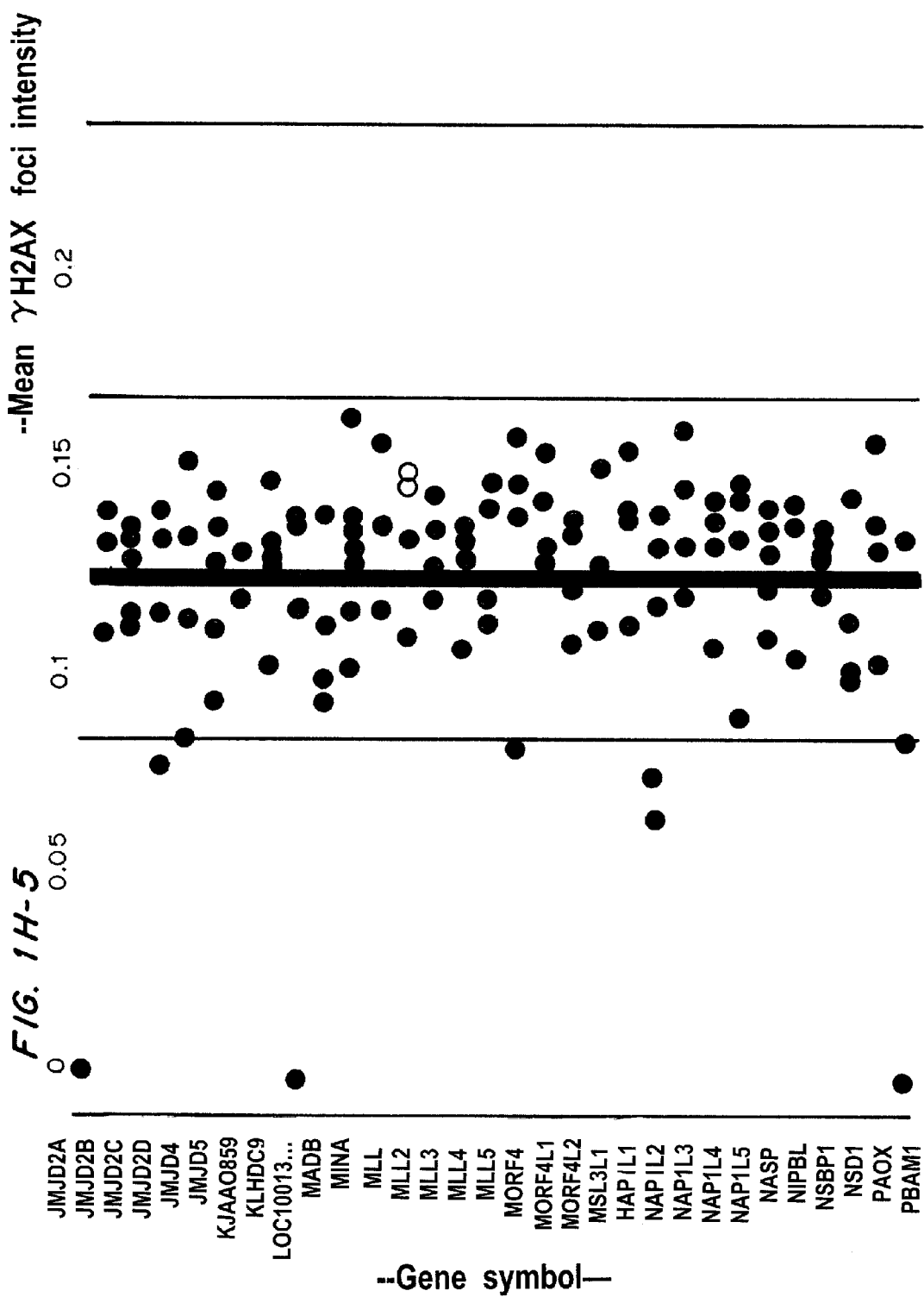
FIG. 5 is a diagram showing the conserved and unique domains of Brd4 isoform A and Brd4 isoform C.
Figures 1, 1H, 2, 3, 4, 5, 6, 7, 8, 9:
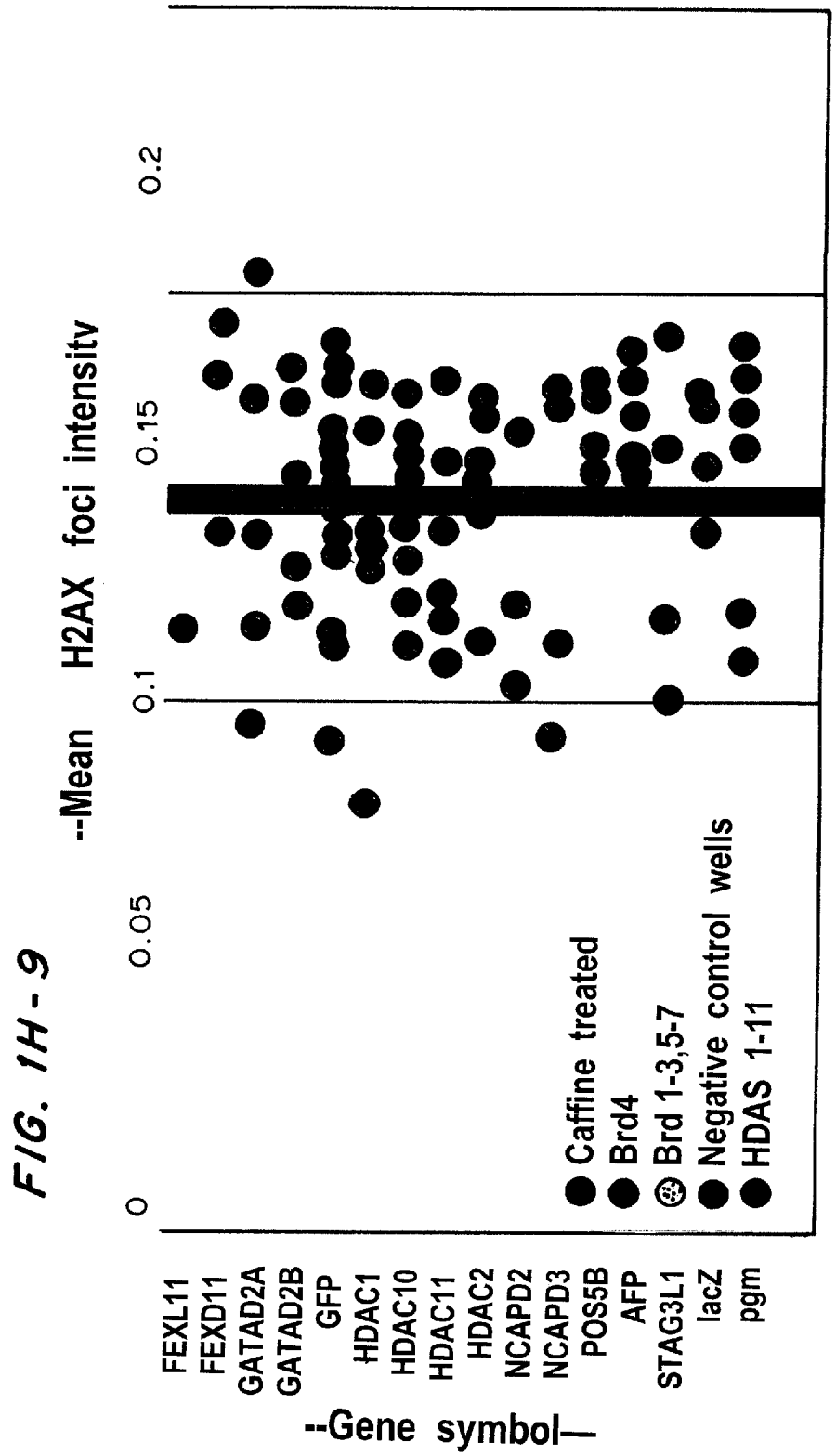
Figure 3A:
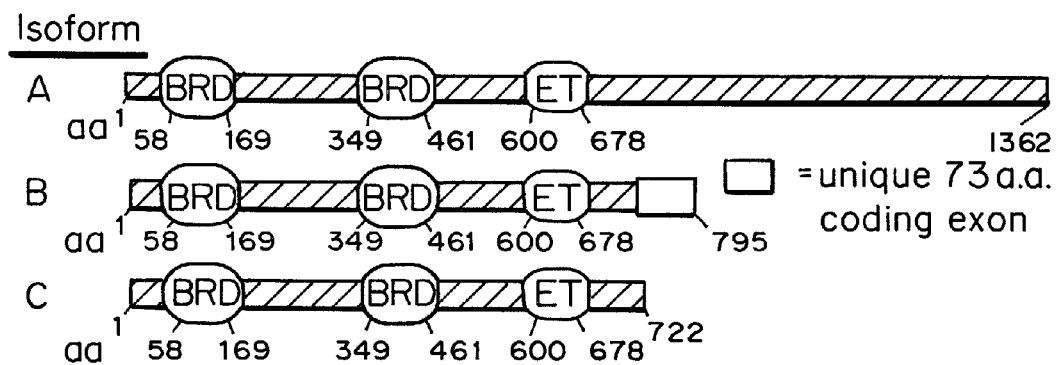
FIG. 3A is a diagram showing the conserved and unique domains of Brd4 isoform A, B, and C.
Figure 3B:
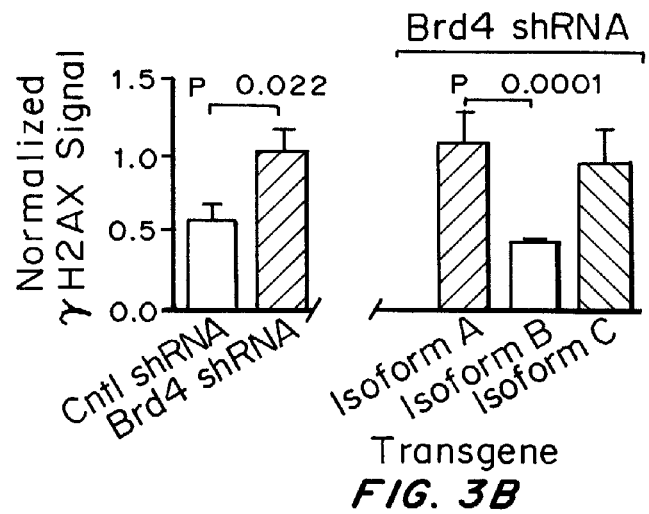
FIG. 3B is a bar graph qualifying γH2AX intensity (10 fields each in three independent experiments) normalized to Brd4 knockdown cells. Error bars represent S.D. of the mean. P-values were calculated using two-tailed student's t test.

Three splice variants of Brd4 are known, all of which are both normally expressed and effectively targeted by Brd4 shRNA in U2OS cells (FIG. 3A). To test the contribution of each isoform to suppression of DDR signaling, shRNA-resistant expression constructs for each isoform were generated and tested their ability to "rescue" the elevated γH2AX phenotype seen in cells expressing Brd4 shRNA. As shown in FIG. 3B, re-expression of isoform B most effectively reversed the increased H2AX phosphorylation observed in Brd4 knockdown cells following irradiation. Importantly, in contrast to the elevated DDR signaling and enhanced cell cycle arrest and survival seen upon Brd4 knockdown, overexpression of isoform B in U2OS cells in the absence of Brd4 knockdown almost completely eliminated γH2AX foci formation, and severely reduced ATM autophosphorylation on Ser-1981, 53BP1 foci formation, and foci formation of multiple DDR signaling molecules marked by a pan-phospho-SQ antibody, indicating potent inhibition of the DDR. These effects were not observed with Brd4 isoforms A and C (FIG. 5). In addition, Brd4 isoform B-overexpressing cells showed significantly reduced survival following IR (FIG. 3C), implicating isoform B as a suppressor of DNA damage signaling and response.

Example 4

Brd4 Bromodomain 1 is Important for the Activity of Brd4 Isoform B

Brd4 contains 2 bromodomains, modular signaling domains that are known to bind to acetyllysine-containing sequence motifs in histones and other proteins. The first bromodomain has highest affinity in vitro for histone H3K14Ac peptides, while the second bromodomain has similarly high affinity for histone H4K5Ac and H4K14Ac peptides (F. Vollmuth, et al., *J Biol Chem*, 284:36547 (2009)). To probe whether these interactions were critical for the ability of Brd4 to modulate γH2AX signaling, Brd4 bromodomain binding to acetyl-lysine was blocked with the small molecule JQ1 (P. Filippakopoulos, et al., *Nature*, 468:1067 (2010)). Treatment of cells with this inhibitor [(+)JQ1], but not its inactive enantiomer [(−)JQ1], resulted in enhanced H2AX phosphorylation following IR, recapitulating the results obtained following Brd4 knockdown.

Figure 3C:
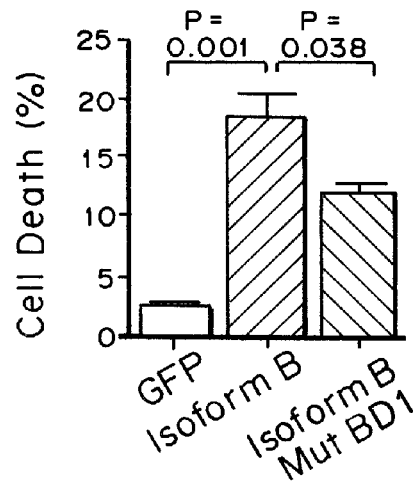
FIG. 3C is a bar graph showing cell death (%) in control, isoform B expression cells, and cells expression isoform B with a mutation in bromodomain 1, 24 hours after exposure to 10 Gy IR. Error bars represent S.D. of the mean. P-values were calculated using two-tailed student's t test.

Next, point mutations that abrogate acetyl lysine binding by each of the Brd4 bromodomains were examined (A. Dey, et al., *Proc Natl Acad Sci USA*, 100:8758 (2003)). Mutation of bromodomain 1, but not bromodomain 2, reversed the ability of Brd4 isoform B to inhibit DDR signaling, and suppressed the increase in cell death following IR in isoform B overexpressing cells (FIG. 3C). Finally, the ability of Brd4 isoform B to suppress γH2AX foci formation was reversed by treatment of the cells with JQ1, but not its inactive enantiomer, consistent with more potent inhibition of Brd4 bromodomain 1 than bromodomain 2 by JQ1, as reported previously (P. Filippakopoulos, et al., *Nature*, 468:1067 (2010). Finally, strong co-localization of Brd4 isoform B with nuclear H3K14Ac within cells that was abrogated by mutation of bromodomain 1 was observed.

Example 4

DNA Damage and Repair Signaling Effects of Brd4 are not Mediated Via Transcriptional Changes in DNA Damage and Repair-Associated mRNA Levels As with many other chromatin-interacting proteins, Brd4 also has a defined role in transcriptional modulation, in this case via its interactions with the P-TEFb transcriptional complex, (D. C. Hargreaves, et al., *Cell*, 138:129 (2009); M. K. Jang, et al., *Molecular Cell*, 19:523 (2005); Z. Yang, et al., *Molecular Cell*, 19:535 (2005)). The expression pattern of mRNAs derived from cells stably expressing control and Brd4 shRNA were profiled to investigate the contribution of Brd4-driven transcriptional changes to the suppression of DNA damage signaling. No statistically significant differences in gene expression were detected between these samples at a BH-adjusted p-value of 0.05 using L1MMA (G. K. Smyth, et al., *Stat Appl Genet Mol Biol*, 3: Article 3 (2004)). Further relaxation of the stringency for statistical significance revealed a small number of genes differentially expressed 2 fold or more only one of which, CHEK2, is known to participate in DDR signaling (FIG. 6A-1, 6A-2, 6B, 6C). Importantly, however, short term Brd4 knockdowns with siRNA, or inhibition with JQ1, both of which are sufficient to increase γH2AX foci formation after irradiation, showed no change in CHEK2 mRNA, and neither long-term nor short term Brd4 knockdown had any effect on the protein levels of DDR molecules themselves, including Chk2. (FIG. 6A-1, 6A-2, 6B, 6C). Moreover, the suppression of DDR signaling by Brd4 isoform B overexpression was insensitive to transcription inhibition with a-amanitin, or translation inhibition with cycloheximide, indicating that the DDR signaling effects of Brd4 are not mediated via transcriptional changes in DDR-associated mRNA levels, and suggesting that the mRNA changes seen with long-term Brd4 inhibition could be compensatory changes from upregulated DDR signaling.

Example 5

Brd4 Isoform B Expression Levels Correlate with Treatment Response

Figure 4A:
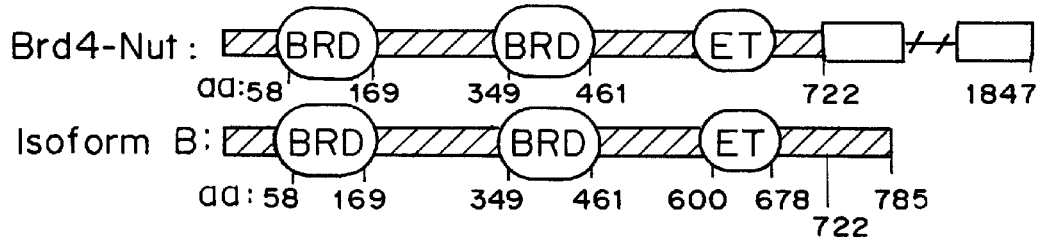
FIG. 4A is a diagram showing the conserved and unique domains of Brd4-Nut and Brd4 isoform B.
Figure 4B:
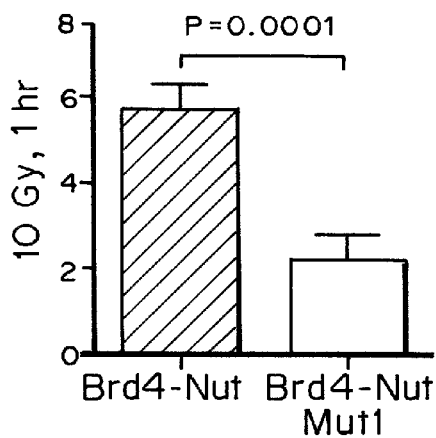
FIG. 4B is a bar graph showing cell death 1 hour after exposure to 10 Gy IR for cells expressing Brd4-Nut or Brd4-Nut with a mutation in bromodomain 1.
Figure 4C:
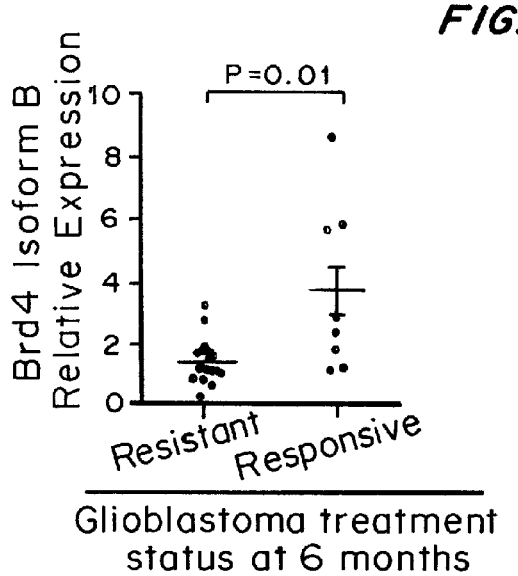
FIG. 4C is a dot plot showing relative mRNA expression of Brd4 isoform B in tumor specimens from glioblastoma patients with stable disease (responsive) or progressive tumor (resistant) 6 months after treatment with radiotherapy and temozolomide.
Figure 4D:
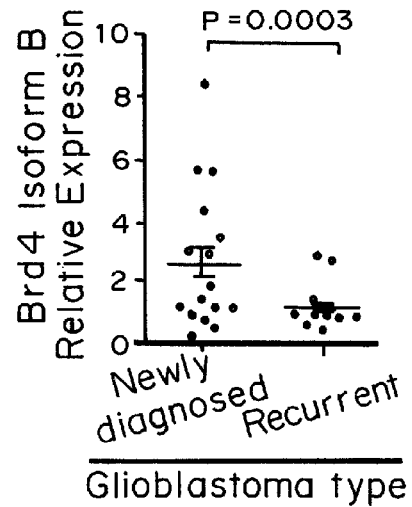
FIG. 4D is a dot plot showing relative mRNA expression of Brd4 isoform B in tumor specimens from newly diagnosed glioblastoma patients and patients with recurrent disease. Lines in (4C) and (4D) indicate mean and error bars indicate standard error of the mean. P-values are given from unpaired, two-tailed student's t test.
Figure 7A:
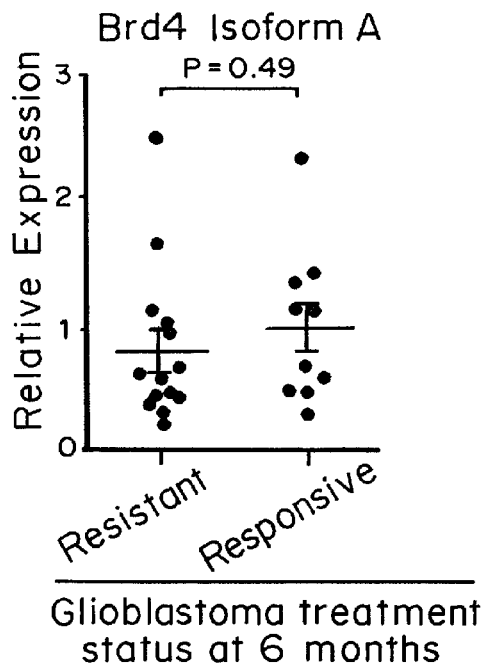
FIG. 7A is a dot plot showing relative mRNA expression of Brd4 isoform A in tumor specimens from glioblastoma patients with stable disease (responsive) or progressive tumor (resistant) 6 months after definitive chemo-radiotherapy to 60 Gy with concurrent daily temodar at 75 mg/m².
Figure 7B:
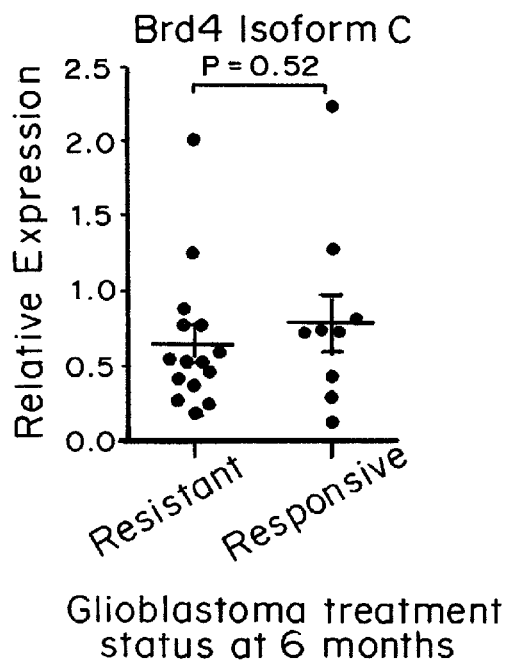
FIG. 7B is a dot plot showing relative mRNA expression of Brd4 isoform C in tumor specimens from glioblastoma patients with stable disease (responsive) or progressive tumor (resistant) 6 months after definitive chemo-radiotherapy to 60 Gy with concurrent daily temodar at 75 mg/m².
Figure 7C:
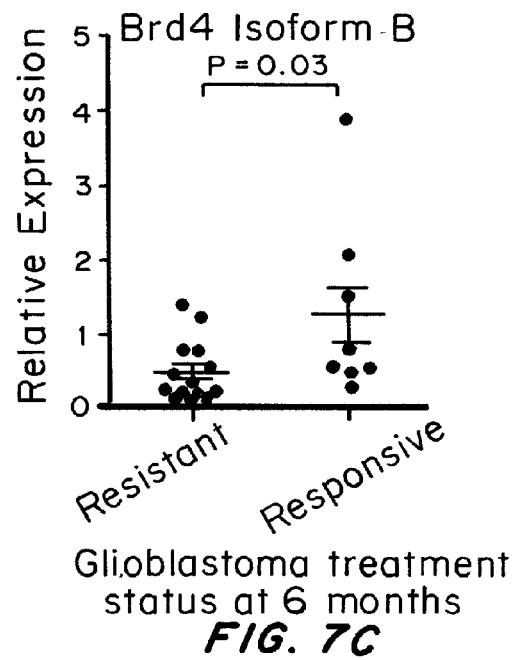
FIG. 7C is a dot plot showing relative mRNA expression of Brd4 isoform B in tumor specimens from glioblastoma patients with stable disease (responsive) or progressive tumor (resistant) 6 months after definitive chemo-radiotherapy to 60 Gy with concurrent daily temodar at 75 mg/m². Lines indicate mean and error bars indicate standard error of the mean. P-values are given from unpaired, two-tailed student's t-test.

Materials and Methods
  Human Tumor Specimens
  All tumor collection and clinical data analysis was performed with IRB approval and monitoring of the Dana-Farber/Harvard cancer center on protocol 07-231. Human glioblastoma specimens were collected at the time of surgery and immediately flashfrozen in liquid nitrogen. Pathological analysis of the specimens was performed by a board certified neuro-pathologist to verify >80% tumor cell content. All patients received standard radiotherapy to a total dose of 60 Gy with concurrent temozolomide chemotherapy as described by Stupp, et al., *N Engl. J. Med.*, 352:987 (2005). Clinical data from patients was collected and correlated to tumor specimens using the following criteria: Tumor progression was defined as greater than 25% increase in the contrast enhancing tumor volume on magnetic resonance imaging at 6 months after diagnosis. Stable disease was defined as patients without tumor progression at 6 months after diagnosis. Recurrent tumor specimens were obtained from patients with tumor progression who had disease that was amenable to surgical resection, and was collected as outlined above.
Results
  Brd4 is a target of the t(15;19) chromosomal translocation in the rare human epithelial carcinoma NUT Midline Carcinoma (NMC). NMC is a highly aggressive cancer with a poor prognosis. Reports indicate that the only effective treatments include radiation therapy as part of a multi-modality approach (J. Engleson, et al., *BMC Cancer*, 6:69 (2006); F. Mertens, et al., *Pediatr Blood Cancer*, 49:1015 (2007); G. Santis, et al., *Journal of clinical oncology: official journal of the American Society of Clinical Oncology*, (2011)). The expressed fusion protein from the t(15;19) translocation places NUT (Nuclear Protein in Testis) at the same site as the unique 73 amino acid insert in Brd4 isoform B (FIG. 4A) (French, et al., *Oncogene*, 27:2237 (2008), French, et al., *Clin. Oncol.*, 22:4135 (2004), French, et al., *J. Clin. Path.*, 14 (2008)).
  Next, the effects of Brd4 isoform B effects on radiation-induced DDR signaling were examined. It was discovered that both Brd4 isoform B and the Brd4-NUT fusion protein co-localize with H3acK14, and this association is disrupted by mutation of bromodomain 1. In contrast to the diffuse nuclear localization pattern of Brd4, however, the Brd4-NUT fusion protein forms punctate nuclear foci in which H3K14Ac is sequestered. Importantly, these Brd4-NUT-enriched regions strongly exclude the formation of γH2AX foci after IR, similar to the more global effects seen with the diffusely localized isoform B. In addition, expression of the Brd4-NUT fusion protein, like isoform B itself, sensitizes cells to IR-induced death, and this effect that can be rescued by mutation of bromodomain 1 (FIG. 4B).
  The rarity of this tumor and scarcity of tumor tissue made further direct exploration of the role of the Brd4-NUT fusion protein in treatment response difficult. Following the identification of the endogenous Brd4 isoform B as a DDR response modulator with similarities to the cancer-derived Brd4-NUT fusion protein prompted the expression of isoform B in glioblastoma multiforme was investigated. Glioblastoma multiforme is common tumor for which radiotherapy plays a central treatment role, and for which human tumor samples are more readily available. Tumors from patients who either responded to radiation therapy or experienced treatment failure at 6 months after diagnosis were tested. Strikingly, a strong correlation between Brd4 isoform B expression level, and treatment response was observed (FIG. 4C). Expression of Brd4 isoforms A and C did not show a similar correlation (FIGS. 7A and B), while a second independent tumor dataset confirmed the correlation of isoform B expression level with treatment response (FIG. 7C). Furthermore, in a set of glioblastoma tumors collected either at the time of initial diagnosis, or at the time of treatment failure, there was a striking suppression of Brd4 isoform B expression in the recurrent tumors (FIG. 4D).

CONCLUSIONS

Figure 4E:
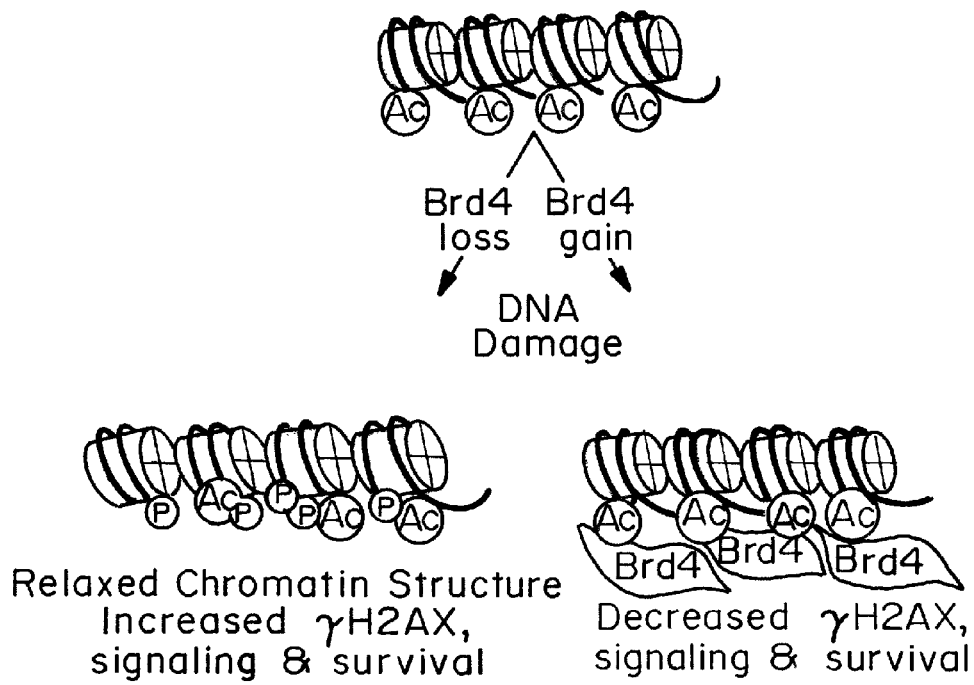
FIG. 4E is a model for Brd4-mediated effects on DNA damage signaling via epigenetic alterations in chromatin structure.
Figure 5:
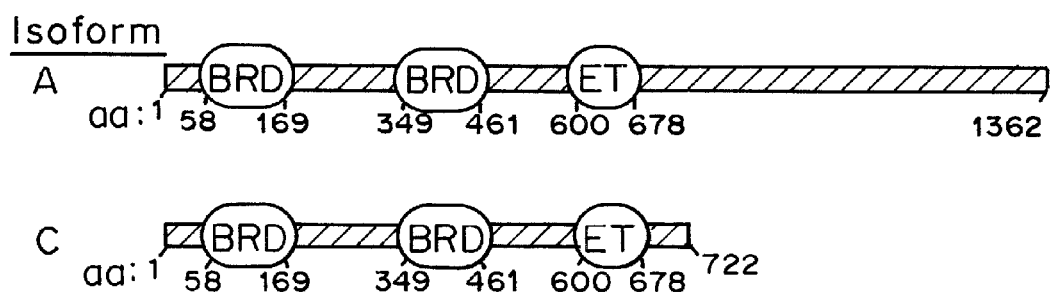
Figures 1, 6A:
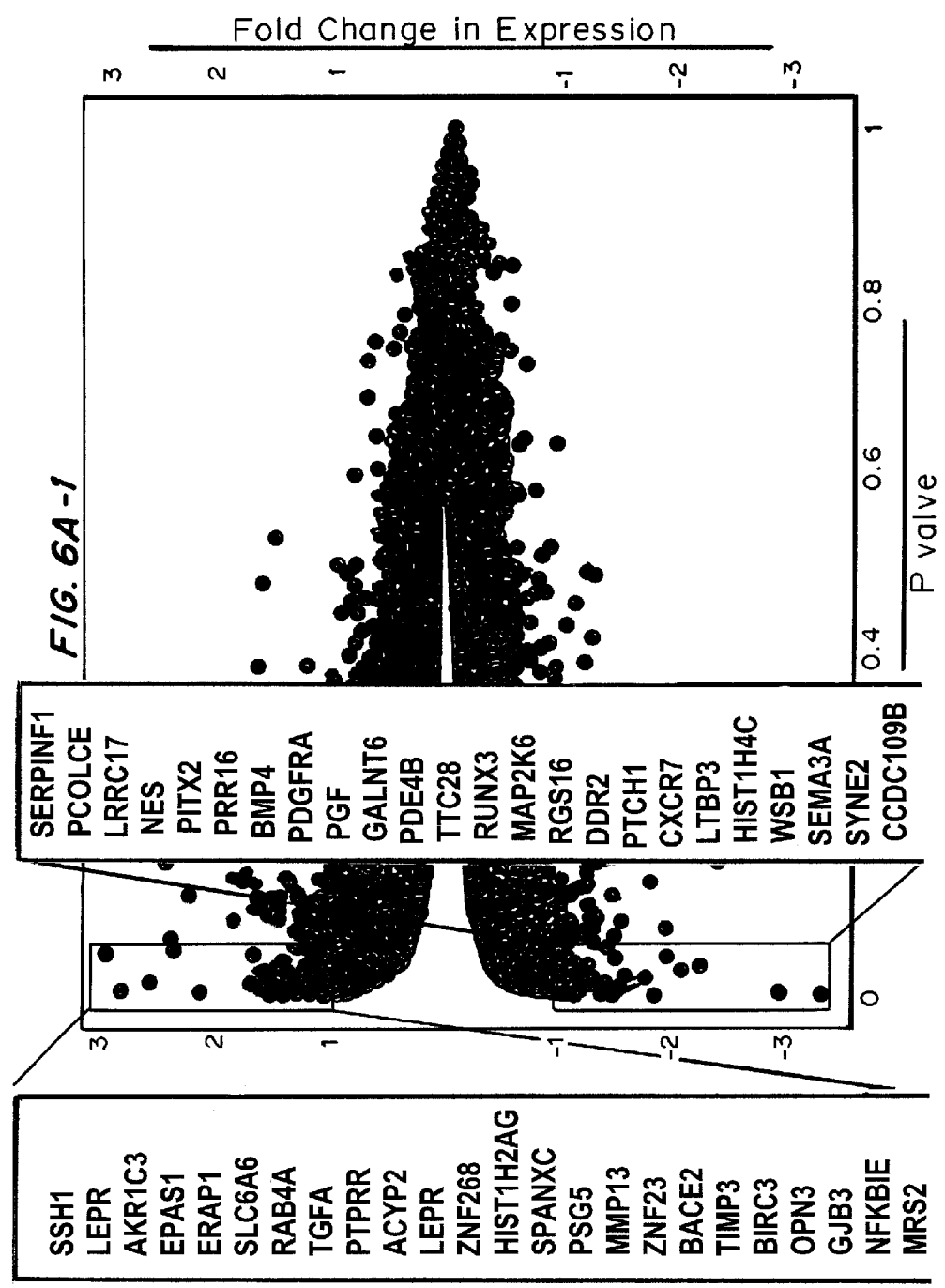
Figure 6B:
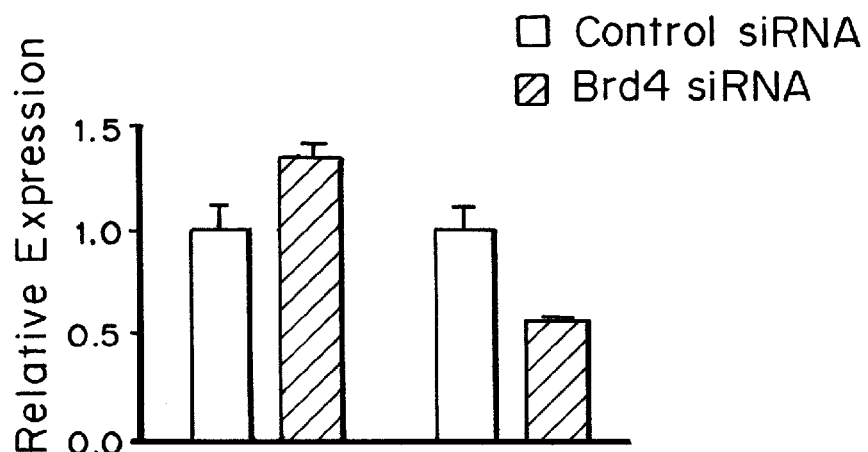
FIG. 6B is a bar graph showing relative expression of CHEK2 and BRD4 in control and Brd4 siRNA knockdown cells.
Figure 6C:
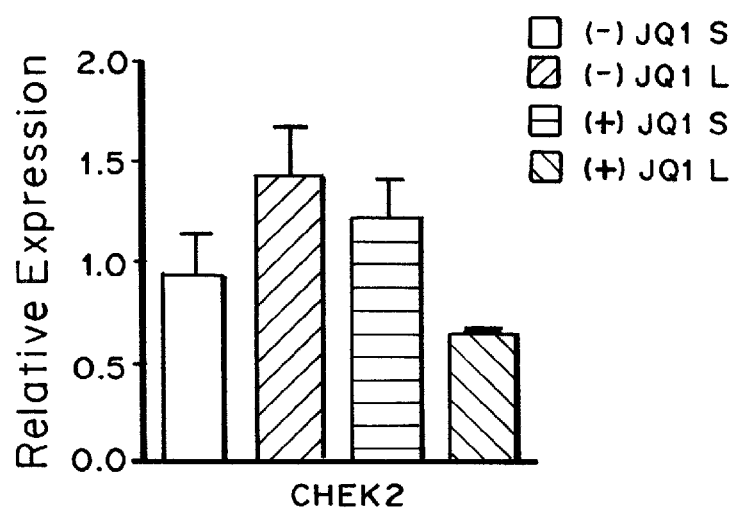
FIG. 6C is a bar graph showing relative expression of CHEK2 in cells treated with (−)JQ1 S (16 hrs), (−)JQ1 L (144 hrs), (+)JQ1 S (16 hrs), or (+)JQ1 L (144 hrs).

Taken together, the data presented in the Examples above indicate that structural alterations in chromatin mediated by Brd4 acetyl-lysine binding function to attenuate the DNA damage signaling response to IR. These effects on DDR signaling are consistent with the epigenetic induction of a chromatin structure that is inhibitory to the formation of γH2AX in the case of higher levels of Brd4 isoform B expression, or a more "open" chromatin structure that facilitates the formation of γH2AX foci when Brd4 is expression is reduced, or following pharmacological inhibition of its bromodomain binding, as shown schematically in FIG. 4E. The data indicate that the effects of Brd4 on DDR signaling are not mediated via transcriptional changes in DDR-associated mRNAs through interactions with the P-TEFb transcriptional complex. Additionally, loss of Brd4 bromodomain 1 function, which completely abrogates its DDR suppressive effect, has been shown to have no effect on the ability of Brd4 to modulate gene transcription by P-TEFb (M. K. Jang, et al., *Molecular Cell*, 19:523 (2005)). This finding is in line with the recent identification of other chromatin interacting proteins such as KAP-1 and Brg1 that have roles in DNA damage signaling that do not seem to arise directly from transcriptional activity that these molecules also possess (Y. Ziv, et al., *Nature*, 8:870 (2006); A. Goodarzi, et al., *Molecular Cell*, 31:167 (2008); H.-S. Lee, et al., *The EMBO Journal*, 29:1434 (2010)). In fact, the findings described herein implicate histone acetylation and acetyl-lysine binding domains in the more general concept that specific relaxed chromatin structures are important in propagating H2AX phosphorylation and DDR signaling (M. Murga, et al., *The Journal of Cell Biology*, 178:1101 (2007); M. Kruhlak, *The Journal of Cell Biology*, 172:823 (2006); I. G. Cowell, et al., *PLoS ONE*, 2:e1057 (2007)).
  The connection between Brd4 and DNA damage signaling in the context of cancer has several important implications. First, elevated levels of isoform B expression appear to be an indicator of clinical response for tumors like glioblastoma multiforme to radiation therapy. Second, the existence of pharmacological inhibitors of Brd4 bromodomains raises the possibility of novel anti-cancer therapies by targeting epigenetic modifications that modulate the DDR (B. E. Schwartz, et al., *Cancer research,* 71:2686 (2011); P. Filippakopoulos, et al., *Nature,* 468:1067 (2010)). Many precancerous lesions, for example, display oncogene-induced stress that triggers a DDR-mediated growth arrest (J. Bartkova, et al., *Nature,* 434:864 (2005); J. Bartkova, et al., *Nature,* 444:633 (2006); R. Di Micco, et al., *Nature,* 444:638 (2006); R. Di Micco, et al., *Nature cell biology* (2011)). To escape DDR-induced senescence and proceed to the malignant phenotype, tumor cells must suppress this DDR signaling. At later times, restoration of checkpoint signaling is important for resistance to genotoxic treatments. The finding that Brd4 isoform B expression is enhanced in glioblastoma tumors that respond to therapy, but suppressed in the tumor subpopulation that recurs after radiation treatment is consistent with this model. Drugs like JQ1 that target the Brd4 bromodomains and increase DNA damage signaling are therefore likely to enhance cell cycle arrest and death when given alone, but must be used cautiously in combination with genotoxic agents.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of reducing the DNA damage response in a cell comprising contacting the cell with an effective amount of a Brd4 polypeptide or a nucleic acid encoding the Brd4 polypeptide to reduce the DNA damage response in the cell, wherein the Brd4 polypeptide comprises at least 95% sequence identity to the Brd4 isoform B having the amino acid sequence of SEQ ID NO:22.

2. A method for reducing overproliferation of cells or increasing sensitivity of cells to cytotoxic agents comprising contacting the cells with an effective amount of a Brd4 polypeptide or a nucleic acid encoding the Brd4 polypeptide to inhibit or reduce cellular DNA repair in cells, wherein the Brd4 polypeptide comprises at least 95% sequence identity to the Brd4 isoform B having the amino acid sequence of SEQ ID NO:22.

3. The method of claim 1, further comprising radiation therapy in an effective amount to promote the death of cells exposed to the combination of Brd4 polypeptide and radiation.

4. The method of claim 2 wherein the cell is a cancer cell, pre-cancerous cell, or a tumor cell.

5. The method of claim 1 further comprising inducing DNA damage in the cell by exposing the cells to a DNA damaging agent.

6. The method of claim 1, wherein the Brd4 polypeptide comprises Brd4 isoform B.

7. The method of claim 1, wherein the contacting occurs in vivo after administering the Brd4 polypeptide or the nucleic acid encoding the Brd4 polypeptide to a subject in need thereof.

8. The method of claim 2, wherein the Brd4 polypeptide comprises Brd4 isoform B.

9. The method of claim 2, wherein the contacting occurs in vivo after administering the Brd4 polypeptide or the nucleic acid encoding the Brd4 polypeptide to a subject in need thereof.

10. The method of claim 7, wherein the subject has a tumor.

11. The method of claim 10, further comprising treating the subject with radiation therapy directed against the tumor.

12. The method of claim 11, wherein the radiation therapy is ionizing radiation therapy.

13. A method of treating cancer comprising administering to a subject with cancer a pharmaceutical composition comprising an effective amount of a Brd4 polypeptide or a nucleic acid encoding the Brd4 polypeptide to reduce DNA repair in combination with radiation therapy, wherein the combination of the Brd4 polypeptide and the radiation therapy increases death of the cancer cells relative to treating the subject with the radiation therapy in the absence of the Brd4 polypeptide, wherein the Brd4 polypeptide comprises at least 95% sequence identity to the Brd4 isoform B having the amino acid sequence of SEQ ID NO:22, or at least 95% sequence identity to the Brd4-NUT having the amino acid sequence of SEQ ID NO:24.

14. The method of claim 13, wherein the Brd4 polypeptide comprises Brd4 isoform B or Brd4-NUT.

15. The method of claim 14, wherein the cancer is glioma.

16. The method of claim 13, wherein the Brd4 polypeptide is packaged into or associated with a polymeric matrix, depo, particle, coating or device for controlled or sustained release of the compound.

17. The method of claim 16, wherein the polymeric matrix, depo, particle, coating or device is implanted in the subject at a site in which a decrease in DNA repair is desired.

18. The method of claim 1, wherein the Brd4 polypeptide comprises the bromodomain 1, the extraterminal (ET) domain, and the C-terminal tail of Brd4 isoform B.

19. The method of claim 1, wherein the Brd4 polypeptide comprises Brd4 isoform B.

20. The method of claim 1, wherein the Brd4 polypeptide comprises SEQ ID NO:1 operably linked to SEQ ID NO:3.

21. A method of reducing the DNA damage response in a cell comprising contacting the cell with an effective amount of a Brd4 polypeptide or a nucleic acid encoding the Brd4 polypeptide to reduce the DNA damage response in the cell, wherein the Brd4 polypeptide comprises at least 95% sequence identity to the Brd4-NUT having the amino acid sequence of SEQ ID NO:24, and wherein the contacting occurs in vivo after administering the Brd4 polypeptide or the nucleic acid encoding the Brd4 polypeptide to a subject in need thereof.

22. The method of claim 21, further comprising radiation therapy in an effective amount to promote the death of cells exposed to the combination of Brd4 polypeptide and radiation.

23. The method of claim 21, further comprising inducing DNA damage in the cell by exposing the cell to a DNA damaging agent.

24. The method of claim 23, wherein the subject has a tumor.

25. The method of claim 24, further comprising treating the subject with radiation therapy directed against the tumor.

26. The method of claim 25, wherein the radiation therapy is ionizing radiation therapy.

27. The method of claim 21, wherein the Brd4 polypeptide comprises Brd4-NUT.

28. A method for reducing overproliferation of cells or increasing sensitivity of cells to cytotoxic agents comprising contacting the cells with an effective amount of a Brd4 polypeptide or a nucleic acid encoding the Brd4 polypeptide to inhibit or reduce cellular DNA repair in cells, wherein the Brd4 polypeptide comprises at least 95% sequence identity to the Brd4-NUT having the amino acid sequence of SEQ ID NO:24, and wherein the contacting occurs in vivo after administering the Brd4 polypeptide or the nucleic acid encoding the Brd4 polypeptide to a subject in need thereof.

29. The method of claim 28, wherein the cell is a cancer cell, pre-cancerous cell, or a tumor cell.

30. The method of claim 28, wherein the Brd4 polypeptide comprises Brd4-NUT.

* * * * *

SEQUENCE LISTING

```
<160> NUMBER OF SEQ ID NOS: 25

<210> SEQ ID NO 1
<211> LENGTH: 73
<212> TYPE: PRT
<213> ORGANISM: Artificial Sequence
<220> FEATURE:
<223> OTHER INFORMATION: Synthetic Peptide

<400> SEQUENCE: 1

Trp Lys His Gln Phe Ala Trp Pro Phe Gln Gln Pro Val Asp Ala Val
1               5                   10                  15

Lys Leu Asn Leu Pro Asp Tyr Tyr Lys Ile Ile Lys Thr Pro Met Asp
            20                  25                  30

Met Gly Thr Ile Lys Lys Arg Leu Glu Asn Asn Tyr Tyr Trp Asn Ala
        35                  40                  45

Gln Glu Cys Ile Gln Asp Phe Asn Thr Met Phe Thr Asn Cys Tyr Ile
    50                  55                  60

Tyr Asn Lys Pro Gly Asp Asp Ile Val
65                  70

<210> SEQ ID NO 2
<211> LENGTH: 73
<212> TYPE: PRT
<213> ORGANISM: Artificial Sequence
<220> FEATURE:
<223> OTHER INFORMATION: Synthetic peptide.

<400> SEQUENCE: 2

Lys His Ala Ala Tyr Ala Trp Pro Phe Tyr Lys Pro Val Asp Val Glu
1               5                   10                  15

Ala Leu Gly Leu His Asp Tyr Cys Asp Ile Ile Lys His Pro Met Asp
            20                  25                  30

Met Ser Thr Ile Lys Ser Lys Leu Glu Ala Arg Glu Tyr Arg Asp Ala
        35                  40                  45

Gln Glu Phe Gly Ala Asp Val Arg Leu Met Phe Ser Asn Cys Tyr Lys
    50                  55                  60

Tyr Asn Pro Pro Asp His Glu Val Val
65                  70

<210> SEQ ID NO 3
<211> LENGTH: 75
<212> TYPE: PRT
<213> ORGANISM: Artificial Sequence
<220> FEATURE:
```

<223> OTHER INFORMATION: Synthetic peptide.

<400> SEQUENCE: 3

Ala Phe Cys Thr Ser Gly Asp Phe Val Ser Pro Gly Pro Ser Pro Tyr
1               5                   10                  15

His Ser His Val Gln Cys Gly Arg Phe Arg Glu Met Leu Arg Trp Phe
            20                  25                  30

Leu Val Asp Val Glu Gln Thr Ala Ala Gly Gln Pro His Arg Gln Ser
        35                  40                  45

Ala Ala Gly Pro Ala Ile Thr Trp Ala Pro Ala Ile Ala Tyr Pro Ser
    50                  55                  60

Pro Glu Cys Ala Arg Cys Cys Val Gly Cys Ser
65                  70                  75

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide.

<400> SEQUENCE: 4

Gly Ser Gly Ser
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide.

<400> SEQUENCE: 5

Gly Gly Gly Ser
1

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide.

<400> SEQUENCE: 6

Gly Gly Gly Gly Ser Gly Gly Gly Ser Gly Gly Gly Ser
1               5                   10                  15

<210> SEQ ID NO 7
<211> LENGTH: 19
<212> TYPE: PRT
<213> ORGANISM: Artificial Sequence
<220> FEATURE:
<223> OTHER INFORMATION: Synthetic peptide.

<400> SEQUENCE: 7

Gly Gly Gly Gly Ser Gly Gly Gly Ser Gly Gly Gly Ser Gly
1               5                   10                  15

Gly Gly Ser

<210> SEQ ID NO 8
<211> LENGTH: 7
<212> TYPE: PRT
<213> ORGANISM: Artificial Sequence
<220> FEATURE:

<223> OTHER INFORMATION: Synthetic Peptide

<400> SEQUENCE: 8

Arg Arg Arg Arg Arg Arg Arg
1               5

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide.

<400> SEQUENCE: 9

Arg Arg Gln Arg Arg Thr Ser Lys Leu Met Lys Arg
1               5                   10

<210> SEQ ID NO 10
<211> LENGTH: 27
<212> TYPE: PRT
<213> ORGANISM: Artificial Sequence
<220> FEATURE:
<223> OTHER INFORMATION: Synthetic peptide.

<400> SEQUENCE: 10

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 11
<211> LENGTH: 29
<212> TYPE: PRT
<213> ORGANISM: Artificial Sequence
<220> FEATURE:
<223> OTHER INFORMATION: Synthetic peptide.

<400> SEQUENCE: 11

Trp Glu Ala Lys Leu Ala Lys Ala Leu Ala Lys Ala Leu Ala Lys His
1               5                   10                  15

Leu Ala Lys Ala Leu Ala Lys Ala Leu Lys Cys Glu Ala
            20                  25

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide.

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 21
<212> TYPE: DNA
<213> ORGANISM: Artificial Sequence
<220> FEATURE:
<223> OTHER INFORMATION: Synthetic primer.

<400> SEQUENCE: 13
ctcctcctaa aaagacgaag a                                        21

<210> SEQ ID NO 14

```
<211> LENGTH: 25
<212> TYPE: DNA
<213> ORGANISM: Artificial Sequence
<220> FEATURE:
<223> OTHER INFORMATION: Synthetic primer.

<400> SEQUENCE: 14
ttcggagtct tcgctgtcag aggag                                     25

<210> SEQ ID NO 15
<211> LENGTH: 25
<212> TYPE: DNA
<213> ORGANISM: Artificial Sequence
<220> FEATURE:
<223> OTHER INFORMATION: Synthetic primer.

<400> SEQUENCE: 15
gccccttctt ttttgacttc ggagc                                     25

<210> SEQ ID NO 16
<211> LENGTH: 25
<212> TYPE: DNA
<213> ORGANISM: Artificial Sequence
<220> FEATURE:
<223> OTHER INFORMATION: Synthetic primer.

<400> SEQUENCE: 16
gccctgggga cacgaagtct ccact                                     25

<210> SEQ ID NO 17
<211> LENGTH: 25
<212> TYPE: DNA
<213> ORGANISM: Artificial Sequence
<220> FEATURE:
<223> OTHER INFORMATION: Synthetic primer.

<400> SEQUENCE: 17
ccgttttatt aagagtccgt gtcca                                     25

<210> SEQ ID NO 18
<211> LENGTH: 24
<212> TYPE: DNA
<213> ORGANISM: Artificial Sequence
<220> FEATURE:
<223> OTHER INFORMATION: Synthetic primer.

<400> SEQUENCE: 18
acagataaat accgaacata cagc                                      24

<210> SEQ ID NO 19
<211> LENGTH: 24
<212> TYPE: DNA
<213> ORGANISM: Artificial Sequence
<220> FEATURE:
<223> OTHER INFORMATION: Synthetic primer.

<400> SEQUENCE: 19
gacggcgttt tcctttccct acaa                                      24

<210> SEQ ID NO 20
<211> LENGTH: 20
<212> TYPE: DNA
<213> ORGANISM: Artificial Sequence
<220> FEATURE:
<223> OTHER INFORMATION: Synthetic primer.

<400> SEQUENCE: 20
```
gatgccctgg aggaagtgct                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer.

<400> SEQUENCE: 21
agcaggcaca acaccacgtt                                               20

<210> SEQ ID NO 22
<211> LENGTH: 794
<212> TYPE: PRT
<213> ORGANISM: Homo sapiens

<400> SEQUENCE: 22

```
Met Ser Ala Glu Ser Gly Pro Gly Thr Arg Leu Arg Asn Leu Pro Val
1               5                   10                  15

Met Gly Asp Gly Leu Glu Thr Ser Gln Met Ser Thr Thr Gln Ala Gln
            20                  25                  30

Ala Gln Pro Gln Pro Ala Asn Ala Ala Ser Thr Asn Pro Pro Pro
        35                  40                  45

Glu Thr Ser Asn Pro Asn Lys Pro Lys Arg Gln Thr Asn Gln Leu Gln
    50                  55                  60

Tyr Leu Leu Arg Val Val Leu Lys Thr Leu Trp Lys His Gln Phe Ala
65                  70                  75                  80

Trp Pro Phe Gln Gln Pro Val Asp Ala Val Lys Leu Asn Leu Pro Asp
                85                  90                  95

Tyr Tyr Lys Ile Ile Lys Thr Pro Met Asp Met Gly Thr Ile Lys Lys
            100                 105                 110

Arg Leu Glu Asn Asn Tyr Tyr Trp Asn Ala Gln Glu Cys Ile Gln Asp
        115                 120                 125

Phe Asn Thr Met Phe Thr Asn Cys Tyr Ile Tyr Asn Lys Pro Gly Asp
    130                 135                 140

Asp Ile Val Leu Met Ala Glu Ala Leu Glu Lys Leu Phe Leu Gln Lys
145                 150                 155                 160

Ile Asn Glu Leu Pro Thr Glu Glu Thr Glu Ile Met Ile Val Gln Ala
                165                 170                 175

Lys Gly Arg Gly Arg Gly Arg Lys Glu Thr Gly Thr Ala Lys Pro Gly
            180                 185                 190

Val Ser Thr Val Pro Asn Thr Thr Gln Ala Ser Thr Pro Pro Gln Thr
        195                 200                 205

Gln Thr Pro Gln Pro Asn Pro Pro Val Gln Ala Thr Pro His Pro
    210                 215                 220

Phe Pro Ala Val Thr Pro Asp Leu Ile Val Gln Thr Pro Val Met Thr
225                 230                 235                 240

Val Val Pro Pro Gln Pro Leu Gln Thr Pro Pro Val Pro Pro Gln
                245                 250                 255

Pro Gln Pro Pro Ala Pro Ala Pro Gln Pro Val Gln Ser His Pro
    260                 265                 270

Pro Ile Ile Ala Ala Thr Pro Gln Pro Val Lys Thr Lys Lys Gly Val
        275                 280                 285

Lys Arg Lys Ala Asp Thr Thr Thr Pro Thr Thr Ile Asp Pro Ile His
    290                 295                 300
```

```
Glu Pro Pro Ser Leu Pro Pro Glu Pro Lys Thr Thr Lys Leu Gly Gln
305                 310                 315                 320

Arg Arg Glu Ser Ser Arg Pro Val Lys Pro Lys Lys Asp Val Pro
            325                 330                 335

Asp Ser Gln Gln His Pro Ala Pro Glu Lys Ser Ser Lys Val Ser Glu
                340                 345                 350

Gln Leu Lys Cys Cys Ser Gly Ile Leu Lys Glu Met Phe Ala Lys Lys
                355                 360                 365

His Ala Ala Tyr Ala Trp Pro Phe Tyr Lys Pro Val Asp Val Glu Ala
                370                 375                 380

Leu Gly Leu His Asp Tyr Cys Asp Ile Ile Lys His Pro Met Asp Met
385                 390                 395                 400

Ser Thr Ile Lys Ser Lys Leu Glu Ala Arg Glu Tyr Arg Asp Ala Gln
                405                 410                 415

Glu Phe Gly Ala Asp Val Arg Leu Met Phe Ser Asn Cys Tyr Lys Tyr
                420                 425                 430

Asn Pro Pro Asp His Glu Val Val Ala Met Ala Arg Lys Leu Gln Asp
                435                 440                 445

Val Phe Glu Met Arg Phe Ala Lys Met Pro Asp Glu Pro Glu Glu Pro
                450                 455                 460

Val Val Ala Val Ser Ser Pro Ala Val Pro Pro Thr Lys Val Val
465                 470                 475                 480

Ala Pro Pro Ser Ser Ser Asp Ser Ser Ser Asp Ser Ser Ser Asp Ser
                485                 490                 495

Asp Ser Ser Thr Asp Asp Ser Glu Glu Glu Arg Ala Gln Arg Leu Ala
                500                 505                 510

Glu Leu Gln Glu Gln Leu Lys Ala Val His Glu Gln Leu Ala Ala Leu
                515                 520                 525

Ser Gln Pro Gln Gln Asn Lys Pro Lys Lys Lys Glu Lys Asp Lys Lys
                530                 535                 540

Glu Lys Lys Lys Glu Lys His Lys Arg Lys Glu Glu Val Glu Glu Asn
545                 550                 555                 560

Lys Lys Ser Lys Ala Lys Glu Pro Pro Lys Lys Thr Lys Lys Asn
                565                 570                 575

Asn Ser Ser Asn Ser Asn Val Ser Lys Lys Glu Pro Ala Pro Met Lys
                580                 585                 590

Ser Lys Pro Pro Pro Thr Tyr Glu Ser Glu Glu Glu Asp Lys Cys Lys
                595                 600                 605

Pro Met Ser Tyr Glu Glu Lys Arg Gln Leu Ser Leu Asp Ile Asn Lys
                610                 615                 620

Leu Pro Gly Glu Lys Leu Gly Arg Val Val His Ile Ile Gln Ser Arg
625                 630                 635                 640

Glu Pro Ser Leu Lys Asn Ser Asn Pro Asp Glu Ile Glu Ile Asp Phe
                645                 650                 655

Glu Thr Leu Lys Pro Ser Thr Leu Arg Glu Leu Glu Arg Tyr Val Thr
                660                 665                 670

Ser Cys Leu Arg Lys Lys Arg Lys Pro Gln Ala Glu Lys Val Asp Val
                675                 680                 685

Ile Ala Gly Ser Ser Lys Met Lys Gly Phe Ser Ser Ser Glu Ser Glu
                690                 695                 700

Ser Ser Ser Glu Ser Ser Ser Ser Asp Ser Glu Asp Ser Glu Thr Ala
705                 710                 715                 720
```

Phe Cys Thr Ser Gly Asp Phe Val Ser Pro Gly Ser Pro Tyr His
                725                 730                 735

Ser His Val Gln Cys Gly Arg Phe Arg Glu Met Leu Arg Trp Phe Leu
            740                 745                 750

Val Asp Val Glu Gln Thr Ala Ala Gly Gln Pro His Arg Gln Ser Ala
        755                 760                 765

Ala Gly Pro Ala Ile Thr Trp Ala Pro Ala Ile Ala Tyr Pro Ser Pro
    770                 775                 780

Glu Cys Ala Arg Cys Cys Val Gly Cys Ser
785                 790

<210> SEQ ID NO 23
<211> LENGTH: 3255
<212> TYPE: DNA
<213> ORGANISM: Homo sapiens

<400> SEQUENCE: 23

```
ggcgtcagtg cgctggcggc ggcggcggcg gcggcggcgg cggcggctgg gctgtttgtt      60
ctggtctccc gcagccgagg agccgaagca gtggcggcgg cagcggctgc ggcggctgcc     120
ggcggtgccc gcgggcgagc gcggcctgtg agctcggcag agcggcgggc gggccccggc     180
gccgcgcagg cagctcgggg aggggcggc ggcagcgggc ggacggccgg cggggcggc      240
gtgcggccta cgtctcaga gtgcctggtg aagaatgtga tgggatcact agcatgtctg      300
cggagagcgg ccctgggacg agattgagaa atctgccagt aatggggat ggactagaaa      360
cttcccaaat gtctacaaca caggcccagg cccaaccccca gccagccaac gcagccagca      420
ccaacccccc gccccagag acctccaacc ctaacaagcc caagaggcag accaaccaac     480
tgcaatacct gctcagagtg gtgctcaaga cactatggaa acaccagttt gcatggcctt     540
tccagcagcc tgtggatgcc gtcaagctga acctccctga ttactataag atcattaaaa     600
cgcctatgga tatgggaaca ataaagaagc gcttggaaaa caactattac tggaatgctc     660
aggaatgtat ccaggacttc aacactatgt ttacaaattg ttacatctac aacaagcctg     720
gagatgacat agtcttaatg gcagaagctc tggaaaagct cttcttgcaa aaaataaatg     780
agctacccac agaagaaacc gagatcatga tagtccaggc aaaaggaaga ggacgtggga     840
ggaaagaaac agggacagca aaacctggcg tttccacggt accaaacaca actcaagcat     900
cgactcctcc gcagacccag acccctcagc cgaatcctcc tcctgtgcag gccacgcctc     960
acccccttccc tgccgtcacc ccggacctca tcgtccagac ccctgtcatg acagtggtgc    1020
ctccccagca actgcagacg cccccgccag tgccccccca gccacaaccc caccccgctc    1080
cagctcccca gcccgtacag agccacccac ccatcatcgc ggccacccca gcctgtgaa    1140
agacaaagaa gggagtgaag aggaaagcag acaccaccac cccaccacc attgaccca    1200
ttcacgagcc accctcgctg ccccgggagc ccaagaccac caagctgggc cagcggcggg    1260
agagcagccg gcctgtgaaa cctccaaaga aggacgtgcc cgactctcag cagcacccag    1320
caccagagaa gagcagcaag gtctcggagc agctcaagtg ctgcagcggc atcctcaagg    1380
agatgtttgc caagaagcac gccgcctacg cctggccctt ctacaagcct gtggacgtgg    1440
aggcactggg cctacacgac tactgtgaca tcatcaagca ccccatggac atgagcacaa    1500
tcaagtctaa actggaggcc gtgagtacc gtgatgctca ggagtttggt gctgacgtcc    1560
gattgatgtt ctccaactgc tataagtaca acccctccga ccatgaggtg gtggccatgg    1620
cccgcaagct ccaggatgtg ttcgaaatgc gctttgccaa gatgccggac gagcctgagg    1680
```

```
agccagtggt ggccgtgtcc tccccggcag tgccccctcc caccaaggtt gtggccccgc   1740
cctcatccag cgacagcagc agcgatagct cctcggacag tgacagttcg actgatgact   1800
ctgaggagga gcgagcccag cggctggctg agctccagga gcagctcaaa gccgtgcacg   1860
agcagcttgc agccctctct cagccccagc agaacaaacc aaagaaaaag agaaagaca    1920
agaaggaaaa gaaaaagaa aagcacaaaa ggaaagagga agtggaagag aataaaaaaa    1980
gcaaagccaa ggaacctcct cctaaaaaga cgaagaaaaa taatagcagc aacagcaatg   2040
tgagcaagaa ggagccagcg cccatgaaga gcaagccccc tcccacgtat gagtcggagg   2100
aagaggacaa gtgcaagcct atgtcctatg aggagaagcg gcagctcagc ttggacatca   2160
acaagctccc cggcgagaag ctgggccgcg tggtgcacat catccagtca cgggagccct   2220
ccctgaagaa ttccaacccc gacgagattg aaatcgactt tgagaccctg aagccgtcca   2280
cactgcgtga gctggagcgc tatgtcacct cctgtttgcg gaagaaaagg aaacctcaag   2340
ctgagaaagt tgatgtgatt gccggctcct ccaagatgaa gggcttctcg tcctcagagt   2400
cggagagctc cagtgagtcc agctcctctg acagcgaaga ctccgaaaca gctttctgca   2460
ccagtggaga cttcgtgtcc cagggccttc cccgtatca cagtcacgtg cagtgcggcc    2520
gcttcaggga gatgcttcgc tggttttctg gggatgtgga gcagactgca gctggccagc   2580
cgcatcgcca gtctgctgct ggccctgcca tcacctgggc cccagccatt gcctaccct    2640
cccagagtg tgctcgttgc tgtgttggct gctcctgaat ctgccctaac tccacacgca   2700
cctggacttg cgtgtccctc ctgcagttct aactaacagt cccttctttt caagccccgt   2760
gggtctgcac gttggaccct gggttcccca ttagagccca ccttctgagc agcagcctca   2820
gtgggaggtg gaggcaggta gtgatgctgg gtgccaggtg ggagtggaga ggggactgct   2880
ctcctccaag tgtgcacttt cctcattatt ctcaggggcg cagatgctca ggctggcgca   2940
ggggagaggc tagggaggga gccatggtgc ccagaaggcc tggcgaccag ccctgctga   3000
gagatggagc taacatcctg tgtttacggc aacgggggtt gccgctaggc tggtgcagct   3060
gtcagtgagc tggcgtgctg cagaccacct gagagctggc cctagggtct caggcagact   3120
ggggagtggg gatccacagt gggaaacctg tgttttggca gtagactcct gcatgttctc   3180
ccacgggcct gtcccatccc tgggattttt ttctaactag aaataaatgc taaccctcaa   3240
aaaaaaaaaa aaaaa                                                    3255
```

<210> SEQ ID NO 24
<211> LENGTH: 1846
<212> TYPE: PRT
<213> ORGANISM: Homo sapiens

<400> SEQUENCE: 24

Met Ser Ala Glu Ser Gly Pro Gly Thr Arg Leu Arg Asn Leu Pro Val
1               5                   10                  15

Met Gly Asp Gly Leu Glu Thr Ser Gln Met Ser Thr Thr Gln Ala Gln
            20                  25                  30

Ala Gln Pro Gln Pro Ala Asn Ala Ala Ser Thr Asn Pro Pro Pro
        35                  40                  45

Glu Thr Ser Asn Pro Asn Lys Pro Lys Arg Gln Thr Asn Gln Leu Gln
    50                  55                  60

Tyr Leu Leu Arg Val Val Leu Lys Thr Leu Trp Lys His Gln Phe Ala
65                  70                  75                  80

Trp Pro Phe Gln Gln Pro Val Asp Ala Val Lys Leu Asn Leu Pro Asp
                85                  90                  95

-continued

```
Tyr Tyr Lys Ile Ile Lys Thr Pro Met Asp Met Gly Thr Ile Lys Lys
            100                 105                 110

Arg Leu Glu Asn Asn Tyr Tyr Trp Asn Ala Gln Glu Cys Ile Gln Asp
            115                 120                 125

Phe Asn Thr Met Phe Thr Asn Cys Tyr Ile Tyr Asn Lys Pro Gly Asp
            130                 135                 140

Asp Ile Val Leu Met Ala Glu Ala Leu Glu Lys Leu Phe Leu Gln Lys
145                 150                 155                 160

Ile Asn Glu Leu Pro Thr Glu Thr Glu Ile Met Ile Val Gln Ala
            165                 170                 175

Lys Gly Arg Gly Arg Gly Arg Lys Glu Thr Gly Thr Ala Lys Pro Gly
            180                 185                 190

Val Ser Thr Val Pro Asn Thr Thr Gln Ala Ser Thr Pro Pro Gln Thr
            195                 200                 205

Gln Thr Pro Gln Pro Asn Pro Pro Val Gln Ala Thr Pro His Pro
            210                 215                 220

Phe Pro Ala Val Thr Pro Asp Leu Ile Val Gln Thr Pro Val Met Thr
225                 230                 235                 240

Val Val Pro Pro Gln Pro Leu Gln Thr Pro Pro Val Pro Pro Gln
            245                 250                 255

Pro Gln Pro Pro Ala Pro Ala Pro Gln Pro Val Gln Ser His Pro
            260                 265                 270

Pro Ile Ile Ala Ala Thr Pro Gln Pro Val Lys Thr Lys Gly Val
            275                 280                 285

Lys Arg Lys Ala Asp Thr Thr Thr Pro Thr Thr Ile Asp Pro Ile His
            290                 295                 300

Glu Pro Pro Ser Leu Pro Pro Glu Pro Lys Thr Thr Lys Leu Gly Gln
305                 310                 315                 320

Arg Arg Glu Ser Ser Arg Pro Val Lys Pro Pro Lys Lys Asp Val Pro
            325                 330                 335

Asp Ser Gln Gln His Pro Ala Pro Glu Lys Ser Ser Lys Val Ser Glu
            340                 345                 350

Gln Leu Lys Cys Cys Ser Gly Ile Leu Lys Glu Met Phe Ala Lys Lys
            355                 360                 365

His Ala Ala Tyr Ala Trp Pro Phe Tyr Lys Pro Val Asp Val Glu Ala
            370                 375                 380

Leu Gly Leu His Asp Tyr Cys Asp Ile Ile Lys His Pro Met Asp Met
385                 390                 395                 400

Ser Thr Ile Lys Ser Lys Leu Glu Ala Arg Glu Tyr Arg Asp Ala Gln
            405                 410                 415

Glu Phe Gly Ala Asp Val Arg Leu Met Phe Ser Asn Cys Tyr Lys Tyr
            420                 425                 430

Asn Pro Pro Asp His Glu Val Val Ala Met Ala Arg Lys Leu Gln Asp
            435                 440                 445

Val Phe Glu Met Arg Phe Ala Lys Met Pro Asp Glu Pro Glu Glu Pro
            450                 455                 460

Val Val Ala Val Ser Ser Pro Ala Val Pro Pro Thr Lys Val Val
465                 470                 475                 480

Ala Pro Pro Ser Ser Ser Asp Ser Ser Ser Asp Ser Ser Ser Asp Ser
            485                 490                 495

Asp Ser Ser Thr Asp Asp Ser Glu Glu Glu Arg Ala Gln Arg Leu Ala
            500                 505                 510
```

-continued

```
Glu Leu Gln Glu Gln Leu Lys Ala Val His Glu Gln Leu Ala Ala Leu
            515                 520                 525

Ser Gln Pro Gln Gln Asn Lys Pro Lys Lys Glu Lys Asp Lys Lys
530                 535                 540

Glu Lys Lys Lys Glu Lys His Lys Arg Lys Glu Glu Val Glu Glu Asn
545                 550                 555                 560

Lys Lys Ser Lys Ala Lys Glu Pro Pro Lys Lys Thr Lys Lys Asn
                565                 570                 575

Asn Ser Ser Asn Ser Asn Val Ser Lys Lys Glu Pro Ala Pro Met Lys
            580                 585                 590

Ser Lys Pro Pro Pro Thr Tyr Glu Ser Glu Glu Glu Asp Lys Cys Lys
            595                 600                 605

Pro Met Ser Tyr Glu Glu Lys Arg Gln Leu Ser Leu Asp Ile Asn Lys
        610                 615                 620

Leu Pro Gly Glu Lys Leu Gly Arg Val Val His Ile Ile Gln Ser Arg
625                 630                 635                 640

Glu Pro Ser Leu Lys Asn Ser Asn Pro Asp Glu Ile Glu Ile Asp Phe
                645                 650                 655

Glu Thr Leu Lys Pro Ser Thr Leu Arg Glu Leu Glu Arg Tyr Val Thr
            660                 665                 670

Ser Cys Leu Arg Lys Lys Arg Lys Pro Gln Ala Glu Lys Val Asp Val
        675                 680                 685

Ile Ala Gly Ser Ser Lys Met Lys Gly Phe Ser Ser Ser Glu Ser Glu
        690                 695                 700

Ser Ser Ser Glu Ser Ser Ser Ser Asp Ser Glu Asp Ser Glu Thr Ala
705                 710                 715                 720

Ser Ala Leu Pro Gly Pro Asp Met Ser Met Lys Pro Ser Ala Ala Leu
                725                 730                 735

Ser Pro Ser Pro Ala Leu Pro Phe Leu Pro Thr Ser Asp Pro Pro
            740                 745                 750

Asp His Pro Pro Arg Glu Pro Pro Gln Pro Ile Met Pro Ser Val
            755                 760                 765

Phe Ser Pro Asp Asn Pro Leu Met Leu Ser Ala Phe Pro Ser Ser Leu
770                 775                 780

Leu Val Thr Gly Asp Gly Pro Cys Leu Ser Gly Ala Gly Ala Gly
785                 790                 795                 800

Lys Val Ile Val Lys Val Lys Thr Glu Gly Gly Ser Ala Glu Pro Ser
                805                 810                 815

Gln Thr Gln Asn Phe Ile Leu Thr Gln Thr Ala Leu Asn Ser Thr Ala
            820                 825                 830

Pro Gly Thr Pro Cys Gly Gly Leu Glu Gly Pro Ala Pro Pro Phe Val
            835                 840                 845

Thr Ala Ser Asn Val Lys Thr Ile Leu Pro Ser Lys Ala Val Gly Val
850                 855                 860

Ser Gln Glu Gly Pro Pro Gly Leu Pro Pro Gln Pro Pro Pro Val
865                 870                 875                 880

Ala Gln Leu Val Pro Ile Val Pro Leu Glu Lys Ala Trp Pro Gly Pro
                885                 890                 895

His Gly Thr Thr Gly Glu Gly Gly Pro Val Ala Thr Leu Ser Lys Pro
            900                 905                 910

Ser Leu Gly Asp Arg Ser Lys Ile Ser Lys Asp Val Tyr Glu Asn Phe
            915                 920                 925

Arg Gln Trp Gln Arg Tyr Lys Ala Leu Ala Arg Arg His Leu Ser Gln
```

```
                    930             935             940
Ser Pro Asp Thr Glu Ala Leu Ser Cys Phe Leu Ile Pro Val Leu Arg
945                 950             955                 960

Ser Leu Ala Arg Leu Lys Pro Thr Met Thr Leu Glu Glu Gly Leu Pro
                965             970                 975

Leu Ala Val Gln Glu Trp Glu His Thr Ser Asn Phe Asp Arg Met Ile
            980             985                 990

Phe Tyr Glu Met Ala Glu Arg Phe Met Glu Phe Glu Ala Glu Glu Met
        995             1000            1005

Gln Ile Gln Asn Thr Gln Leu Met Asn Gly Ser Gln Gly Leu Ser
    1010            1015            1020

Pro Ala Thr Pro Leu Lys Leu Asp Pro Leu Gly Pro Leu Ala Ser
    1025            1030            1035

Glu Val Cys Gln Gln Pro Val Tyr Ile Pro Lys Lys Ala Ala Ser
    1040            1045            1050

Lys Thr Arg Ala Pro Arg Arg Gln Arg Lys Ala Gln Arg Pro
    1055            1060            1065

Pro Ala Pro Glu Ala Pro Lys Glu Ile Pro Pro Glu Ala Val Lys
    1070            1075            1080

Glu Tyr Val Asp Ile Met Glu Trp Leu Val Gly Thr His Leu Ala
    1085            1090            1095

Thr Gly Glu Ser Asp Gly Lys Gln Glu Glu Gly Gln Gln Gln
    1100            1105            1110

Glu Glu Glu Gly Met Tyr Pro Asp Pro Gly Leu Leu Ser Tyr Ile
    1115            1120            1125

Asn Glu Leu Cys Ser Gln Lys Val Phe Val Ser Lys Val Glu Ala
    1130            1135            1140

Val Ile His Pro Gln Phe Leu Ala Asp Leu Leu Ser Pro Glu Lys
    1145            1150            1155

Gln Arg Asp Pro Leu Ala Leu Ile Glu Glu Leu Glu Gln Glu Glu
    1160            1165            1170

Gly Leu Thr Leu Ala Gln Leu Val Gln Lys Arg Leu Met Ala Leu
    1175            1180            1185

Glu Glu Glu Glu Asp Ala Glu Ala Pro Pro Ser Phe Ser Gly Ala
    1190            1195            1200

Gln Leu Asp Ser Ser Pro Ser Gly Ser Val Glu Asp Glu Asp Gly
    1205            1210            1215

Asp Gly Arg Leu Arg Pro Ser Pro Gly Leu Gln Gly Ala Gly Gly
    1220            1225            1230

Ala Ala Cys Leu Gly Lys Val Ser Ser Ser Gly Lys Arg Ala Arg
    1235            1240            1245

Glu Val His Gly Gly Gln Gln Ala Leu Asp Ser Pro Arg Gly
    1250            1255            1260

Met His Arg Asp Gly Asn Thr Leu Pro Ser Pro Ser Ser Trp Asp
    1265            1270            1275

Leu Gln Pro Glu Leu Ala Ala Pro Gln Gly Thr Pro Gly Pro Leu
    1280            1285            1290

Gly Val Glu Arg Arg Gly Ser Gly Lys Val Ile Asn Gln Val Ser
    1295            1300            1305

Leu His Gln Asp Gly His Leu Gly Gly Ala Gly Pro Pro Gly His
    1310            1315            1320

Cys Leu Val Ala Asp Arg Thr Ser Glu Ala Leu Pro Leu Cys Trp
    1325            1330            1335
```

```
Gln Gly Gly Phe Gln Pro Glu Ser Thr Pro Ser Leu Asp Ala Gly
    1340            1345                1350

Leu Ala Glu Leu Ala Pro Leu Gln Gly Gln Gly Leu Glu Lys Gln
    1355            1360                1365

Val Leu Gly Leu Gln Lys Gly Gln Gln Thr Gly Gly Arg Gly Val
    1370            1375                1380

Leu Pro Gln Gly Lys Glu Pro Leu Ala Val Pro Trp Glu Gly Ser
    1385            1390                1395

Ser Gly Ala Met Trp Gly Asp Asp Arg Gly Thr Pro Met Ala Gln
    1400            1405                1410

Ser Tyr Asp Gln Asn Pro Ser Pro Arg Ala Ala Gly Glu Arg Asp
    1415            1420                1425

Asp Val Cys Leu Ser Pro Gly Val Trp Leu Ser Ser Glu Met Asp
    1430            1435                1440

Ala Val Gly Leu Glu Leu Pro Val Gln Ile Glu Glu Val Ile Glu
    1445            1450                1455

Ser Phe Gln Val Glu Lys Cys Val Thr Glu Tyr Gln Glu Gly Cys
    1460            1465                1470

Gln Gly Leu Gly Ser Arg Gly Asn Ile Ser Leu Gly Pro Gly Glu
    1475            1480                1485

Thr Leu Val Pro Gly Asp Thr Glu Ser Ser Val Ile Pro Cys Gly
    1490            1495                1500

Gly Thr Val Ala Ala Ala Ala Leu Glu Lys Arg Asn Tyr Cys Ser
    1505            1510                1515

Leu Pro Gly Pro Leu Arg Ala Asn Ser Pro Pro Leu Arg Ser Lys
    1520            1525                1530

Glu Asn Gln Glu Gln Ser Cys Glu Thr Val Gly His Pro Ser Asp
    1535            1540                1545

Leu Trp Ala Glu Gly Cys Phe Pro Leu Leu Glu Ser Gly Asp Ser
    1550            1555                1560

Thr Leu Gly Ser Ser Lys Glu Thr Leu Pro Pro Thr Cys Gln Gly
    1565            1570                1575

Asn Leu Leu Ile Met Gly Thr Glu Asp Ala Ser Ser Leu Pro Glu
    1580            1585                1590

Ala Ser Gln Glu Ala Gly Ser Arg Gly Asn Ser Phe Ser Pro Leu
    1595            1600                1605

Leu Glu Thr Ile Glu Pro Val Asn Ile Leu Asp Val Lys Asp Asp
    1610            1615                1620

Cys Gly Leu Gln Leu Arg Val Ser Glu Asp Thr Cys Pro Leu Asn
    1625            1630                1635

Val His Ser Tyr Asp Pro Gln Gly Glu Gly Arg Val Asp Pro Asp
    1640            1645                1650

Leu Ser Lys Pro Lys Asn Leu Ala Pro Leu Gln Glu Ser Gln Glu
    1655            1660                1665

Ser Tyr Thr Thr Gly Thr Pro Lys Ala Thr Ser Ser His Gln Gly
    1670            1675                1680

Leu Gly Ser Thr Leu Pro Arg Arg Gly Thr Arg Asn Ala Ile Val
    1685            1690                1695

Pro Arg Glu Thr Ser Val Ser Lys Thr His Arg Ser Ala Asp Arg
    1700            1705                1710

Ala Lys Gly Lys Glu Lys Lys Lys Glu Ala Glu Glu Asp
    1715            1720                1725
```

| Glu | Glu | Leu | Ser | Asn | Phe | Ala | Tyr | Leu | Leu | Ala | Ser | Lys | Leu | Ser |
| --- | --- | --- | --- | --- | --- | --- | --- | --- | --- | --- | --- | --- | --- | --- |
| 1730 | | | | | 1735 | | | | | 1740 | | | | |
| Leu | Ser | Pro | Arg | Glu | His | Pro | Leu | Ser | Pro | His | His | Ala | Ser | Gly |
| 1745 | | | | | 1750 | | | | | 1755 | | | | |
| Gly | Gln | Gly | Ser | Gln | Arg | Ala | Ser | His | Leu | Leu | Pro | Ala | Gly | Ala |
| 1760 | | | | | 1765 | | | | | 1770 | | | | |
| Lys | Gly | Pro | Ser | Lys | Leu | Pro | Tyr | Pro | Val | Ala | Lys | Ser | Gly | Lys |
| 1775 | | | | | 1780 | | | | | 1785 | | | | |
| Arg | Ala | Leu | Ala | Gly | Gly | Pro | Ala | Pro | Thr | Glu | Lys | Thr | Pro | His |
| 1790 | | | | | 1795 | | | | | 1800 | | | | |
| Ser | Gly | Ala | Gln | Leu | Gly | Val | Pro | Arg | Glu | Lys | Pro | Leu | Ala | Leu |
| 1805 | | | | | 1810 | | | | | 1815 | | | | |
| Gly | Val | Val | Arg | Pro | Ser | Gln | Pro | Arg | Lys | Arg | Arg | Cys | Asp | Ser |
| 1820 | | | | | 1825 | | | | | 1830 | | | | |
| Phe | Val | Thr | Gly | Arg | Arg | Lys | Lys | Arg | Arg | Ser | Gln | | | |
| 1835 | | | | | 1840 | | | | | 1845 | | | | |

<210> SEQ ID NO 25
<211> LENGTH: 6004
<212> TYPE: DNA
<213> ORGANISM: Homo sapiens

<400> SEQUENCE: 25

```
attctttgga atactactgc tagaagtctg acttaagacc cagcttatgg gccacatggc      60
acccagctgc ttctgcagag aaggcaggcc actgatgggt acagcaaagt gtggtgctgc     120
tggccaagcc aaagacccgt gtaggatgac tgggcctctg ccccttgtgg gtgttgccac     180
tgtgcttgag tgcctggtga agaatgtgat gggatcacta gcatgtctgc ggagagcggc     240
cctgggacga gattgagaaa tctgccagta atggggatg gactagaaac ttcccaaatg      300
tctacaacac aggcccaggc caaccccag ccagccaacg cagccagcac caaccccccg      360
cccccagaga cctccaaccc taacaagccc aagaggcaga ccaaccaact gcaatacctg     420
ctcagagtgg tgctcaagac actatggaaa caccagtttg catggccttt ccagcagcct     480
gtggatgccg tcaagctgaa cctccctgat tactataaga tcattaaaac gcctatggat     540
atgggaacaa taagaagcg cttggaaaac aactattact ggaatgctca ggaatgtatc      600
caggacttca acactatgtt tacaaattgt tacatctaca acaagcctgg agatgacata     660
gtcttaatgg cagaagctct ggaaaagctc ttcttgcaaa aaataaatga gctacccaca     720
gaagaaaccg agatcatgat agtccaggca aaaggaagag acgtgggag gaaagaaaca      780
gggacagcaa aacctggcgt tccacggta ccaaacacaa ctcaagcatc gactcctccg      840
cagacccaga cccctcagcc gaatcctcct cctgtgcagg ccacgcctca cccttccct     900
gccgtcaccc cggacctcat cgtccagacc cctgtcatga cagtggtgcc tccccagcca     960
ctgcagacgc cccgccagt gccccccag ccacaacccc cacccgctcc agctccccag      1020
cccgtacaga gccaccacc catcatcgcg gccaccccac agcctgtgaa gacaaagaag     1080
ggagtgaaga ggaaagcaga caccaccacc cccaccacca ttgaccccat tcacgagcca     1140
ccctcgctgc ccccggagcc caagaccacc aagctgggcc agcggcggga gagcagccgg     1200
cctgtgaaac ctccaaagaa ggacgtgccc gactctcagc agcacccagc accagagaag     1260
agcagcaagg tctcggagca gctcaagtgc tgcagcggca tcctcaagga gatgtttgcc     1320
aagaagcacg ccgcctacgc ctggccccttc tacaagcctg tggacgtgga ggcactgggc     1380
ctacacgact actgtgacat catcaagcac cccatggaca tgagcacaat caagtctaaa     1440
```

```
ctggaggccc gtgagtaccg tgatgctcag gagtttggtg ctgacgtccg attgatgttc   1500
tccaactgct ataagtacaa ccctcctgac catgaggtgg tggccatggc ccgcaagctc   1560
caggatgtgt tcgaaatgcg ctttgccaag atgccggacg agcctgagga gccagtggtg   1620
gccgtgtcct ccccggcagt gcccccctcc accaaggttg tggccccgcc ctcatccagc   1680
gacagcagca gcgatagctc ctcggacagt gacagttcga ctgatgactc tgaggaggag   1740
cgagcccagc ggctggctga gctccaggag cagctcaaag ccgtgcacga gcagcttgca   1800
gccctctctc agccccagca gaacaaacca agaaaaagg agaaagacaa gaggaaaag    1860 aaaaaagaaa agcacaaaag aaaagaggaa gtggaagaga ataaaaaaag caaagccaag   1920
gaacctcctc ctaaaaagac gaagaaaaat aatagcagca acagcaatgt gagcaagaag   1980
gagccagcgc ccatgaagag caagccccct cccacgtatg agtcggagga agaggacaag   2040
tgcaagccta tgtcctatga ggagaagcgg cagctcagct tggacatcaa caagctcccc   2100
ggcgagaagc tgggccgcgt ggtgcacatc atccagtcac gggagccctc cctgaagaat   2160
tccaaccccg acgagattga aatcgacttt gagaccctga gccgtccac actgcgtgag    2220 ctggagcgct atgtcacctc ctgtttgcgg aagaaaagga acctcaagc tgagaaagtt    2280 gatgtgattg ccggctcctc caagatgaag ggcttctcgt cctcagagtc ggagagctcc   2340
agtgagtcca gctcctctga cagcgaagac tccgaaacag catctgcatt gccgggaccg   2400
gatatgagca tgaaacctag tgccgccctg tctccatccc ctgcacttcc ctttctccca    2460
ccaacttctg acccaccaga ccacccaccc agggagccac ctccacagcc catcatgcct   2520
tcagtattct ctccagacaa ccctctgatg ctctctgctt tccccagctc actgttggtg   2580 acagggacg ggggcccttg cctcagtggg gctggggctg gcaaggtcat tgtcaaagtc    2640
aagacagaag gggggtcagc tgagccctct caaaactcaga actttatcct tactcagact   2700
gccctcaatt cgactgcccc gggcactccc tgtggaggcc ttgagggtcc tgcacctcca   2760
tttgtgacag catctaatgt gaagaccatt ctgccctcta aggctgttgg tgtcagccag   2820
gagggtcctc caggccttcc gcctcagcct ccaccaccag ttgctcaact ggtccccatt   2880 gtgccctgg aaaaagcttg gcagggcca catgggacaa ccggggaagg aggtcctgtg      2940
gccactctat ccaagccttc cctaggtgac cgctccaaaa tttccaagga cgtttatgag   3000
aacttccgtc agtggcagcg ttacaaagcc ttggcccgga ggcacctatc ccagagtcct   3060
gacacagaag ctctttcctg ttttcttatc ccagtgcttc gttccctggc ccggctgaag   3120
cccactatga ccctggagga gggactgcca ttggctgtgc aggagtggga gcacaccagc   3180
aactttgacc ggatgatctt ttatgagatg gcagaaaggt tcatggagtt tgaggctgag   3240
gagatgcaga ttcagaacac acagctgatg aatgggtctc agggcctgtc tcctgcaacc   3300
cctttgaaac ttgatcctct agggcccctg gcctctgagg tttgccagca gccagtgtac   3360
attccgaaga aggcagcctc caagacacgg gccccccgcc ggcgtcagcg taaagcccag   3420
agacctcctg ctcctgaggc acccaaggag atcccaccag aagctgtgaa ggagtatgtt   3480
gacatcatgg aatggctggt ggggactcac ttggccactg gggagtcaga tggaaaacaa   3540
gaggaagaag gcagcagca ggaggaggaa gggatgtatc cagatccagg tctcctgagc    3600
tacatcaatg agctgtgttc tcagaaggtc tttgtctcca aggtggaggc tgtcattcac   3660
cctcaatttc tggcagatct gctgtcccca gaaaaacaga gagatccctt ggccttaatt   3720
gaggagctag agcaagaaga aggactcact cttgcccagc tggtccagaa gcgactcatg   3780
```

```
gccttggaag aggaggaaga tgcagaggcg cctccaagtt tcagtggcgc tcagttggac    3840
tcaagtcctt ctggttctgt tgaggatgaa gatggggatg ggcggcttcg gccctcacct    3900
gggcttcagg gggctggggg cgccgcttgc cttggaaagg tttcttcttc aggaaaacgg    3960
gcaagagaag tgcatggtgg gcaggagcaa gccctagata gccccagagg gatgcacagg    4020
gatgggaaca ctctgccatc ccccagcagc tgggacctgc agccagaact tgcagctcca    4080
cagggaactc cgggacccct gggtgtggag aggagagggt ctgggaaggt tataaaccag    4140
gtatctctac atcaggatgg ccatctagga ggcgctgggc ctcctgggca ctgcctggtg    4200
gctgatagga cttcagaggc tctgccccct tgttggcagg gaggcttcca gcctgagagc    4260
actcccagtt tggatgctgg acttgcagag ctggctcctc tgcaaggaca agggttagaa    4320
aagcaagtcc tgggattgca gaaaggacaa caaacagggg gtcgtggagt gcttcctcaa    4380
gggaaggagc ctttagcagt gccctgggaa ggctcttcag gagccatgtg gggagatgac    4440
agaggtaccc ccatggctca gagttatgat cagaatcctt ccctagagc agctggggag    4500 agggacgatg tctgtctcag cccaggagtt tggctgagca gtgagatgga tgctgtaggc    4560
ttggagctgc ctgtacaaat agaggaggtc atagagagct ccaagttga gaagtgtgta    4620 actgagtatc aggaaggctg ccagggactg ggctccaggg gcaacatttc ctgggtcct    4680 ggagaaaccc tagtacctgg ggatacggag agcagtgtga ttccctgtgg aggcacagtt    4740
gcggcagctg ccctagaaaa agaaaactat tgcagcttgc caggaccttt gagggccaac    4800
agcccaccct tgaggtccaa agaaaatcaa gaacagagct gtgaaaccgt agggcatccc    4860
agtgatctgt gggcagaagg ttgcttccca ttgctagaaa gtggtgattc cacactgggg    4920
tcttccaaag aaacccttcc acccacatgc caaggcaatc tccttatcat ggggactgag    4980
gatgcctcct ccttgcctga agccagtcaa gaggcaggga gcagaggcaa ttccttttct    5040
cctctgttgg aaaccataga acctgtcaac atactagatg ttaaagatga ctgtggcctc    5100
caactaaggg tcagcgagga cacctgccca ctgaatgttc attcttatga cccccaagga    5160
gaaggcaggg tggatcctga tctgtccaag cctaaaaacc ttgctccttt acaagagagt    5220
caggagtctt acacaactgg gactcccaaa gcaacatctt ctcaccaggg ccttggaagc    5280
actttgccta aaggggaac caggaatgcc atagttccga gagaaacttc tgttagtaaa    5340
acacacaggt cagcagacag ggccaaagga aaggagaaaa agaaaaagga agcagaggaa    5400
gaggatgagg aactctccaa ctttgcttac ctcttggcct ctaaacttag cctctcacca    5460
agggagcatc ccctcagtcc tcaccatgcc tcaggaggtc agggcagcca gagagcatcc    5520
cacctgctcc ctgctggagc aaaaggcccc agcaaacttc catatcctgt tgccaagtct    5580
gggaagcgag ctctagctgg aggtccagcc cctactgaaa agacacccca ctcaggagct    5640
caacttgggg tccccaggga gaaaccccta gctctgggag tagttcgacc ctcacagcct    5700
cgtaaaaggc ggtgtgacag ttttgtcacg ggcagaagga gaaacgacg tcgtagccag    5760 tagggagcag cgggaccatc tgaccccact tgccagtccc taaggtgggg tgccccagag    5820
tagattccac ccctgctgcc caccaatgga gaatcccaat gttgaatctc atcccaatgt    5880
tgttttgttg ttctgcaaaa gtggcaagca tggagagaga ggtcagactg gctaggctgc    5940
agggggaatt acctttggaa ggagctatat agaaaaaaaa tgaataaagt gttttgttgg    6000
aaaa                                                                6004
```